(12) United States Patent
Siva et al.

(10) Patent No.: US 8,399,222 B2
(45) Date of Patent: Mar. 19, 2013

(54) COMPOSITIONS AND METHODS FOR DETECTING SMALL RNAS, AND USES THEREOF

(75) Inventors: Amara Siva, Oceanside, CA (US); Mark Alan Reynolds, Carlsbad, CA (US)

(73) Assignee: Gen-Probe Incorporated, San Diego, CA (US)

( * ) Notice: Subject to any disclaimer, the term of this patent is extended or adjusted under 35 U.S.C. 154(b) by 648 days.

(21) Appl. No.: 12/625,609

(22) Filed: Nov. 25, 2009

(65) Prior Publication Data

US 2010/0129822 A1     May 27, 2010

Related U.S. Application Data

(60) Provisional application No. 61/117,913, filed on Nov. 25, 2008.

(51) Int. Cl.
    *C12P 19/34*        (2006.01)
    *C12Q 1/68*         (2006.01)

(52) U.S. Cl. ..................................... 435/91.2; 435/6.12

(58) Field of Classification Search ........................ None
See application file for complete search history.

(56) References Cited

U.S. PATENT DOCUMENTS

| | | | |
|---|---|---|---|
| 4,174,384 A | 11/1979 | Ullman et al. | |
| 4,486,539 A | 12/1984 | Ranki et al. | |
| 4,556,643 A | 12/1985 | Paau et al. | |
| 4,725,536 A | 2/1988 | Fritsch et al. | |
| 4,752,566 A | 6/1988 | Collins et al. | |
| 4,766,062 A | 8/1988 | Diamond et al. | |
| 4,818,680 A | 4/1989 | Collins et al. | |
| 4,824,776 A | 4/1989 | Heller et al. | |
| 4,894,325 A | 1/1990 | Englehardt et al. | |
| 5,118,801 A | 6/1992 | Lizardi et al. | |
| 5,124,246 A | 6/1992 | Urdea et al. | |
| 5,268,266 A | 12/1993 | Fritsch et al. | |
| 5,283,174 A | 2/1994 | Arnold, Jr. et al. | |
| 5,288,609 A | 2/1994 | Engelhardt et al. | |
| 5,312,728 A | 5/1994 | Lizardi et al. | |
| 5,439,793 A | 8/1995 | Rose et al. | |
| 5,445,933 A | 8/1995 | Eadie et al. | |
| 5,457,025 A | 10/1995 | Collins et al. | |

(Continued)

FOREIGN PATENT DOCUMENTS

| EP | 0 070 685 A2 | 1/1983 |
|---|---|---|
| EP | 0 229 943 A2 | 7/1987 |

(Continued)

OTHER PUBLICATIONS

PCT International Preliminary Report on Patentability, International Application No. PCT/US2009/065835, Jun. 9, 2011.

(Continued)

*Primary Examiner* — Teresa E Strzelecka
*Assistant Examiner* — Suchira Pande
(74) *Attorney, Agent, or Firm* — Jeffrey E. Landes

(57) ABSTRACT

Compositions and methods are provided for the detection of small RNA target nucleic acids, preferably miRNA target nucleic acids, wherein the compositions and methods provide for sensitive and specific detection of the target nucleic acids. The compositions and methods include using one or more of a first amplification oligomer that is preferably an extender primer, a target capture oligomer that is preferably at least partially double stranded, a promoter primer/provider, a reverse primer that is preferably a universal primer and a detection probe. The compositions and methods are useful for diagnostics, prognostics, monitoring the effectiveness of treatment and/or determining a treatment.

45 Claims, 8 Drawing Sheets

U.S. PATENT DOCUMENTS

| | | | |
|---|---|---|---|
| 5,514,546 | A | 5/1996 | Kool |
| 5,607,834 | A | 3/1997 | Bagwell |
| 5,631,148 | A | 5/1997 | Urdea |
| 5,681,697 | A | 10/1997 | Urdea et al. |
| 5,702,893 | A | 12/1997 | Urdea et al. |
| 5,702,896 | A | 12/1997 | Collins et al. |
| 5,714,380 | A | 2/1998 | Neri et al. |
| 5,723,591 | A | 3/1998 | Livak et al. |
| 5,731,148 | A | 3/1998 | Becker et al. |
| 5,759,777 | A | 6/1998 | Kearney et al. |
| 5,780,224 | A | 7/1998 | Collins |
| 5,827,649 | A | 10/1998 | Rose et al. |
| 5,849,481 | A | 12/1998 | Urdea et al. |
| 5,861,273 | A | 1/1999 | Olson et al. |
| 5,914,230 | A | 6/1999 | Liu et al. |
| 5,925,517 | A | 7/1999 | Tyagi et al. |
| 6,025,133 | A | 2/2000 | Stull et al. |
| 6,030,787 | A | 2/2000 | Livak et al. |
| 6,110,678 | A | 8/2000 | Weisburg et al. |
| 6,150,097 | A | 11/2000 | Tyagi et al. |
| 6,156,501 | A | 12/2000 | McGall et al. |
| 6,221,581 | B1 | 4/2001 | Engelhardt et al. |
| 6,268,128 | B1 | 7/2001 | Collins et al. |
| 6,280,952 | B1 | 8/2001 | Weisburg et al. |
| 6,355,421 | B1 | 3/2002 | Coull et al. |
| 6,361,945 | B1 | 3/2002 | Becker et al. |
| 6,451,588 | B1 | 9/2002 | Egholm et al. |
| RE37,891 | E | 10/2002 | Collins et al. |
| 6,472,522 | B1 | 10/2002 | Horn et al. |
| 6,489,464 | B1 | 12/2002 | Agrawal et al. |
| 6,528,267 | B1 | 3/2003 | Coull et al. |
| 6,534,273 | B2 | 3/2003 | Weisburg et al. |
| 6,534,274 | B2 | 3/2003 | Becker et al. |
| 6,566,055 | B1 | 5/2003 | Monforte et al. |
| 6,576,419 | B1 | 6/2003 | Wei et al. |
| 6,835,542 | B2 | 12/2004 | Becker et al. |
| 6,849,412 | B2 | 2/2005 | Becker et al. |
| 6,903,206 | B1 | 6/2005 | Becker et al. |
| 7,217,807 | B2 | 5/2007 | Bentwich |
| 7,220,544 | B2 | 5/2007 | Inose |
| 7,230,092 | B2 | 6/2007 | Bortolin et al. |
| 7,575,863 | B2 | 8/2009 | Chen et al. |
| RE41,365 | E | 6/2010 | Bowdish et al. |
| 7,851,150 | B2 | 12/2010 | Dahlberg et al. |
| 2002/0114784 | A1 | 8/2002 | Li et al. |
| 2003/0049673 | A1 | 3/2003 | Atkinson et al. |
| 2003/0113781 | A1 | 6/2003 | Bortolin et al. |
| 2005/0186591 | A1 | 8/2005 | Bumcrot et al. |
| 2006/0057564 | A1 | 3/2006 | Wang et al. |
| 2006/0057595 | A1 | 3/2006 | Lao et al. |
| 2006/0068417 | A1* | 3/2006 | Becker et al. ............ 435/6 |
| 2006/0099619 | A1* | 5/2006 | Remacle et al. .......... 435/6 |
| 2006/0292616 | A1 | 12/2006 | Neely et al. |
| 2007/0077582 | A1 | 4/2007 | Slepnev |
| 2007/0099196 | A1 | 5/2007 | Kauppinen et al. |
| 2007/0161004 | A1 | 7/2007 | Brown et al. |

FOREIGN PATENT DOCUMENTS

| | | |
|---|---|---|
| EP | 0 601 889 A2 | 12/1993 |
| EP | 1 288 313 A2 | 3/2003 |
| WO | 92/15708 A1 | 9/1992 |
| WO | 97/08183 A2 | 3/1997 |
| WO | 97/23647 A2 | 7/1997 |
| WO | 98/02582 A1 | 1/1998 |
| WO | 99/22018 A2 | 5/1999 |
| WO | 00/01850 A1 | 1/2000 |
| WO | 00/71740 A2 | 11/2000 |
| WO | 01/94625 A2 | 12/2001 |
| WO | 02/06531 A2 | 1/2002 |
| WO | 2004/081520 A2 | 9/2004 |
| WO | 2006/007567 A2 | 1/2006 |
| WO | 2010/068473 A1 | 6/2010 |

OTHER PUBLICATIONS

PCT Written Opinion, International Application No. PCT/US2009/065835, Mar. 23, 2010.

Exiqon, miRCURY LNA Array, Product Literature, Aug. 20, 2007.

Chen et al., "Real-time quantification of microRNAs by stem-loop RT-PCR." Nucleic Acids Research, 2005, vol. 33 (20), Oxford University Press, Oxford, UK.

Neely et al., "A single-molecule method for the quantitation of microRNA gene expression," Nature Methods, Jan. 2006, pp. 41-46, vol. 3 (1), Nature Publishing Group, New York, NY.

Mattie et al., "Optimized high-throughput microRNA expression profiling provides novel biomarker assessment of clinical prostate and breast cancer biopsies," Molecular Cancer, Jun. 19, 2006, 14 pps., vol. 5 (24), BioMed Central. Bethesda MD, USA.

Raymond et al., "Simple, quantitative primer-extension PCR assay for direct monitoring of microRNAs and short-interfering RNAs," RNA Society, 2005, pp. 1737-1744, vol. 11(11), Cold Spring Harbor Laboratory Press, Cold Spring Harbor, NY.

Ozen et al., "Widespread Deregulation of MicroRNA Expression in Human Prostate Cancer," Oncogene, 2007, pp. 1-6, Nature Publishing Group, New York, NY.

Porkka et al., "MicroRNA Expression Profiling in Prostate Cancer," Cancer Research, Jul. 1, 2007, pp. 6130-6135, vol. 67(13), American Association for Cancer Research, Washington, D.C.

Galardi et al., "miR-221 and miR-222 Expression Affects the Proliferation Potential of Human Prostate Carcinoma Cell Lines by Targeting p27 kip1," J. Biological Chemistry, Aug. 10, 2007, pp. 23716-23724, vol. 282(32), American Society for Biochemistry and Molecular Biology, Washington, D.C.

Mitchell et al., "Circulating microRNAs as stable blood-based markers for cancer detection," Proceedings of the National Academy of Sciences of the United States of America (PNAS), Jul. 29, 2008, pp. 10513-10518, vol. 105(30), The National Academy of Sciences of the USA, Washington, D.C.

Ambs et al., "Genomic Profiling of MicroRNA and Messenger RNA Reveals Deregulated MicroRNA Expression in Prostate Cancer," American Association Cancer Research Journals, Aug. 1, 2008, pp. 6162-6170, vol. 68(15), American Association for Cancer Research, Washington, D.C.

Sun et al., "The Role of microRNA-221 and microRNA-222 in Androgen-Independent Prostate Cancer Cell Lines," American Association Cancer Research Journals, Apr. 15, 2009, pp. 3356-3363, vol. 69(8), American Association for Cancer Research, Washington, D.C.

Siva et al., "Molecular assays for the detection of microRNAs in Prostate Cancer," Molecular Cancer, Mar. 6, 2009, 12 pps., vol. 8 (17), BioMed Central. Bethesda MD, USA.

Written Opinion of the International Searching Authority for PCT/US2005/023555 dated Feb. 14, 2006. (6 pages).

International Preliminary Report on Patentability for PCT/US2005/023555 dated Jan. 9, 2007 (8 pages).

Office Action received in U.S. Appl. No. 11/173,915, dated Mar. 23, 2007 (24 pages).

Office Action received in U.S. Appl. No. 11/173,915, dated Oct. 22, 2007 (69 pages).

Office Action received in U.S. Appl. No. 11/173,915, dated May 14, 2008 (24 pages).

Office Action received in U.S. Appl. No. 11/173,915, dated Nov. 14, 2008 (19 pages).

Office Action received in U.S. Appl. 11/173,915, dated Jun. 12, 2009 (20 pages).

EP Notice of Allowance in corresponding EP Patent Application EP 05 767 727 dated Nov. 11, 2009. (47 pages).

Examiner Interview received in U.S. Appl. No. 11/173,915, dated Mar. 4, 2010 (3 pages).

EP Decision to Grant Pursuant to Article 97(1) in corresponding EP Patent Application EP05 767 727 dated Apr. 1, 2010. (1 page).

Office Action received in U.S. Appl. No. 11/173,915, dated Apr. 16, 2010 (27 pages).

EP Office Action Communication in corresponding EP Patent Application EP 05 767 727 dated Jun. 22, 2007. (7 pages).

Office Action received in U.S. Appl. No. 11/173,915, dated Dec. 18, 2009 (19 pages).

EP Office Action Communication in corresponding EP Patent Application EP 05 767 727 dated Oct. 9, 2008. (9 pages).

International Search Report for PCT/US2005/023555 dated Feb. 14, 2006 (7 pages).

Examiner's Report received in AU Patent Application 2005262357 dated Jun. 9, 2009 (2 pages).
AU Notice of Acceptance in corresponding AU Patent Application 2005262357 dated Oct. 19, 2009 (3 pages).
Bonaldo et al., "Normalization and Subtraction: Two Approaches to Facilitate Gene Discovery." Genome Res., 1996, pp. 791-806, vol. 6 (9), Cold Water Spring Laboratory Press, Cold Spring Harbor, NY.
International Search Report and Written Opinion of the International Searching Authority for PCT/US09/65835 dated Mar. 23, 2010. (15 pages).
Lu et al., "MicroRNA expression profiles classify human cancers," Nature, 2005, 435(9): 834-838, Nature Publishing Group, Basingstoke, United Kingdom.
Bloomston et al., "MicroRNA Expression Patterns to Differentiate Pancreatic Adenocarcinoma From Normal Pancreas and Chronic Pancreatitis," JAMA, 2007, 297(17):1901-1908, American Medical Association, Chicago, USA.
Volinia et al., "A microRNA expression signature of human solid tumors defines cancer gene targets," PNAS, 2006, 103(7):2257-2261, National Academy of Sciences, Washington D.C., USA.
Armitage et al., "Hairpin-Forming Peptide Nucleic Acid Oligomers", 1998, Biochem., 37:9417-9425, USA.
Azhayeva et al., "Selective binding of looped oligonucleotides to a single-stranded DNA and its influence on replication in vitro", 1995, Nucl. Acids Res., 23(21):4255-4261, Oxford University Press, GB.
Bagwell et al., "A new homogeneous assay system for specific nucleic acid sequences: poly-dA and poly-A detection", 1994, Nucl. Acids Res., 22(12):2424-2425, Oxford University Press, GB.
Blok et al., "Amplifiable hybridization probes containing a molecular switch", 1997, Mol. Cell. Probes, 11:187-194, Academic Press Limited, USA.
Bonnet et al., "Kinetics of Conformational Fluctuations in DNA Hairpin-Loops", Proc. Natl. Acad. Sci., Jul. 1998, pp. 8602-8606, vol. 95, No. 15, The National Academy of Sciences, USA.
Bonnet et al., "Thermodynamic Basis of the Enhanced Specificity of Structured DNA Probes", 1999, Proc. Natl Acad. Sci., 96:6171-6176, National Academy of Sciences, USA.
Cardullo et al., "Detection of nucleic acid hybridization by nonradiative fluorescence resonance energy transfer", Proc. Natl. Acad. Sci., Dec. 1988, pp. 8790-8794, vol. 85, No. 23, The National Academy of Sciences, USA.
Case et al., "The unusual stability of the IS10 anti-sense RNA is critical for its function and is determined by the structure of its stem-domain", 1989, EMBO J, 8(13):4297-4305, IRL Press, Germany.
Giesendorf et al., "Molecular Beacons: A New Approach for Semiautomated Mutation Analysis", Clinical Chemistry, Mar. 1998, pp. 482-486, vol. 44, No. 3, American Association for Clinical Chemistry, Inc., USA.
Kostrikis et al., "Spectral Genotyping of Human Alleles", Science, Feb. 1998, pp. 1228-1229, vol. 279, No. 5354, American Association for the Advancement of Science, USA.
Kramer et al., "Replicatable RNA Reporter", Nature, Jun. 1989, pp. 401-402, vol. 339, No. 6223, Macmillan Magazines Ltd., GB.

Lee et al., "Allelic discrimination by nick-translation PCR with fluorogenic probes", Nucleic Acids Research, Aug. 1993, pp. 3761-3766, vol. 21, No. 16, Oxford University Press, GB.
Leone et al., "Molecular beacon probes combined with amplification by NASBA enable homogeneous, real-time detection of RNA", Nucleic Acids Research, May 1998, pp. 2150-2155, vol. 26 No. 9, Oxford University Press, GB.
Livak et al., "Oligonucleotides with Fluorescent Dyes at Opposite Ends Provide a Quenched Probe System Useful for Detecting PCR Product and Nucleic Acid Hybridization", PCR Methods and Applications, Jun. 1995, pp. 357-362, vol. 4, No. 6, Cold Spring Harbor Laboratory Press, USA.
Lubini et al., "Stabilizing effects of the RNA 2'-substituent: crystal structure of an oligodeoxynucleotide duplex containing 2'-O-methylated adenosines", 1994, Chem. & Biol., 1:39-45, Cell Press, USA.
Marras et al., "Multiplex Detection of Single-Nucleotide Variations Using Molecular Beacons", 1999, Genetic Analysis Biomolecular Engineering, 14:151-156, Elsevier Trends Journal, Cambridge, GB.
Mergny et al., "Fluorescence energy transfer as a probe for nucleic acid structures and sequences", Nucleic Acids Research, Mar. 1994, pp. 920-928, vol. 22, No. 6, Oxford University Press, GB.
Morrison et al., "Solution-Phase Detection of Polynucleotides Using Interacting Fluorescent Labels and Competitive Hybridization", Analytical Biochemistry, Dec. 1989, pp. 231-244, vol. 183, No. 2, Academic Press, Inc., USA.
Morrison et al., "Sensitive Fluorescence-Based Thermodynamic and Kinetic Measurements of DNA Hybridization in Solution", Biochemistry, Mar. 1993, pp. 3095-3104, vol. 32, No. 12, American Chemical Society, USA.
Ortiz et al., "PNA molecular beacons for rapid detection of PCR amplicons", Molecular and Cellular Probes, Aug. 1998, pp. 219-226, vol. 12, No. 4, Academic Press, GB.
Piatek et al., "Molecular beacon sequence analysis for detecting drug resistance in *Mycobacterium tuberculosis*", Nature Biotechnology, Apr. 1998, pp. 359-363, vol. 16, No. 4, Nature Publishing Co., USA.
Refregiers et al., "Fluorescence Resonance Energy Transfer Analysis of the Degradation of an Oligonucleotide Protected by a Very Stable Hairpin", 1996, J. Biom. Struc. Dyn., 14(3):365-371, Adenine Press, USA.
Tang et al., "Self-stabilized antisense oligodeoxynucleotide phosphorothioates: properties and anti-HIV activity", 1993, Nucl. Acids Res., 21(11):2729-2735, Oxford University Press, GB.
Tyagi et al., "Molecular Beacons: Probes that Fluoresce upon Hybridization" Nature Biotechnology, Mar. 1, 1996, pp. 303-308, vol. 14(3), Nature Publishing Company, USA.
Varani, "Exceptionally Stable Nucleic Acid Hairpins", Annu. Rev. Biophys. Biomol. Struct., 1995, pp. 379-404, vol. 24, Annual Reviews Inc., USA.
Examinees First Report, Australia Patent Application No. 2009324884, mailed Jun. 21, 2012.

* cited by examiner

```
    a  b  c  d  e            ← Target Nucleic Acid

MIXED WITH

Double-stranded Capture Probe
                ↓
T-T-T-T-T-T-T-T-T   a'  b'  c'    ← Target-complementary Region
A-A-A-A-A-A-A-A     a   b   c

⇓  FORM CAPTURE HYBRID

Capture Support
   ↓        Immobilized Probe       Target-complementary Region
  ○                ↓                          ↓
   A-A-A-A-A-A-A-A-A-A
   T-T-T-T-T-T-T-T-T-T   a'  b'  c'
                    ↗    a   b   c   d   e    ← Target Nucleic Acid
Capture Probe Strand T-T-T-T-T-T-T-T-T   a'  b'  c'    ← Excess Capture Probe strands washed away
A-A-A-A-A-A-A-A     a   b   c   ↙

⇓  RELEASE TARGET & FORM DETECTION HYBRID

Detection Probe
                   ↓
   ★   a'  b'  c'  d'  e'         ← Detection Hybrid
       a   b   c   d   e
       ↑
       Target Nucleic Acid T-T-T-T-T-T-T-T   a'  b'  c'      ← Released Capture Probe Strand
```

FIG. 2

FIG. 6
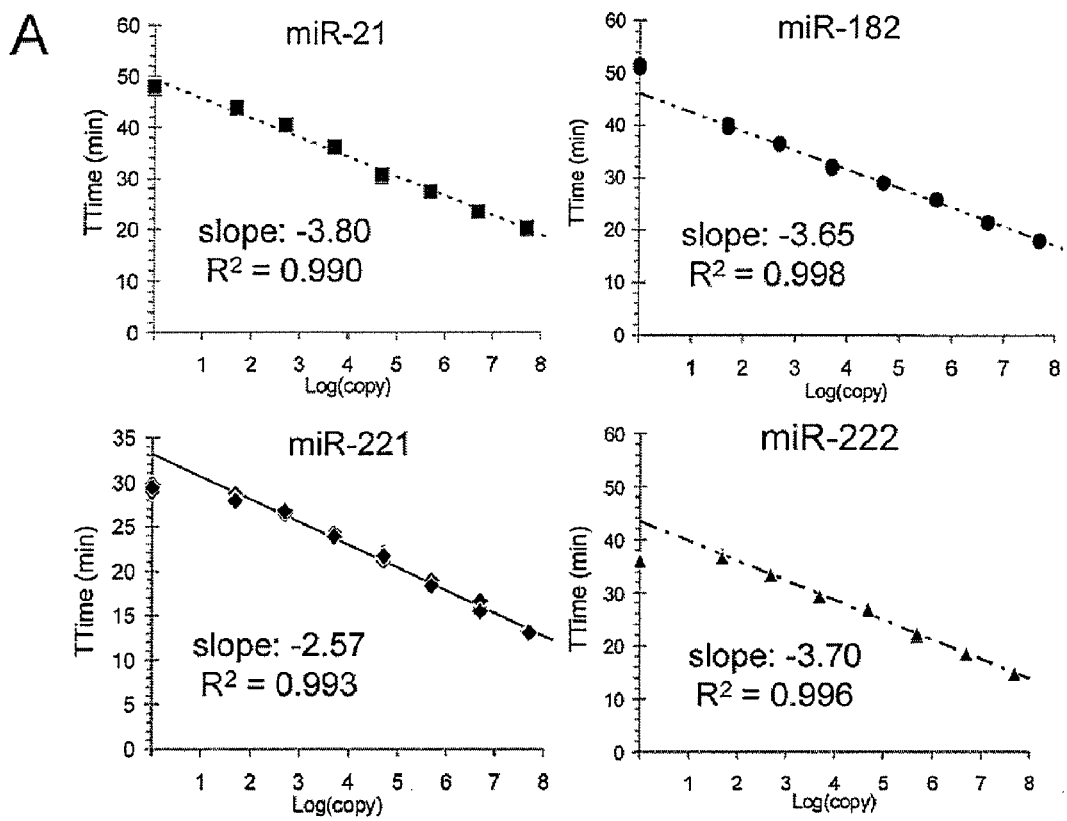
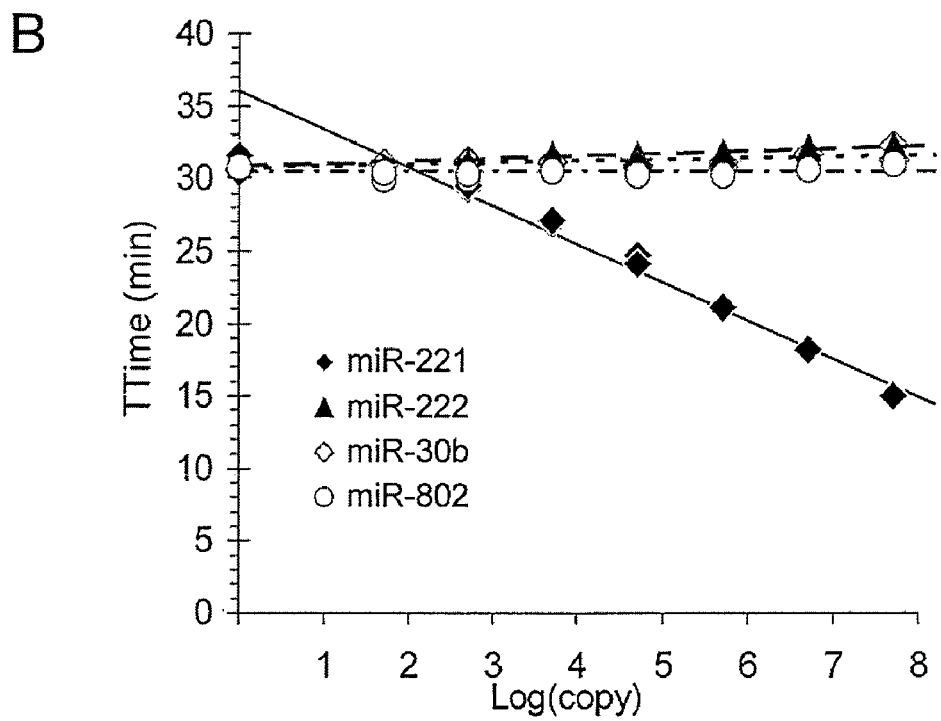

SEQUENCE LISTING

<160> NUMBER OF SEQ ID NOS: 50

<210> SEQ ID NO 1
<211> LENGTH: 47
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (13)..(35)
<223> OTHER INFORMATION: model target hybridizing sequence. Forms the loop portion of a hairpin capture probe. Is coufigured to hybridize to a target nucleic acid.

<400> SEQUENCE: 1
tttttttttt ttnnnnnnnn nnnnnnnnn nnnnnaaaaa aaaaaaa                47

<210> SEQ ID NO 2
<211> LENGTH: 47
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (13)..(35)
<223> OTHER INFORMATION: Model target hybridizing sequence. Forms the loop portion of a hairpin oligomer. Is configured to hybridize with a target nucleic acid.

<400> SEQUENCE: 2
tttttatttt ttnnnnnnnn nnnnnnnnn nnnnnaaaaa aaaaaaa                47

<210> SEQ ID NO 3
<211> LENGTH: 39

```
<212> TYPE: DNA
<213> ORGANISM: Artificial Sequence
<220> FEATURE:
<223> OTHER INFORMATION: Synthetic Oligomer
<220> FEATURE:
<221> NAME/KEY: misc_feature
<222> LOCATION: (1)..(24)
<223> OTHER INFORMATION: Model target hybridizing sequence.  Is
      configured to hybridize to a target nucleic acid.

<400> SEQUENCE: 3
nnnnnnnnnn nnnnnnnnnn nnnntttaaa aaaaaaaa                              39

<210> SEQ ID NO 4
<211> LENGTH: 36
<212> TYPE: DNA
<213> ORGANISM: Artificial Sequence
<220> FEATURE:
<223> OTHER INFORMATION: Synthetic Oligomer

<400> SEQUENCE: 4
tttttttttt ttttagagg atgggttttc tagggg                                 36

<210> SEQ ID NO 5
<211> LENGTH: 35
<212> TYPE: DNA
<213> ORGANISM: Artificial Sequence
<220> FEATURE:
<223> OTHER INFORMATION: Synthetic Oligomer

<400> SEQUENCE: 5
ctctctctct ctctctctct aaaaaaaaaa aaaaa                                 35

<210> SEQ ID NO 6
<211> LENGTH: 36
<212> TYPE: DNA
<213> ORGANISM: Artificial Sequence
<220> FEATURE:
<223> OTHER INFORMATION: Synthetic Oligomer

<400> SEQUENCE: 6
cccctagaaa acccatcctc taaaaaaaaa aaaaaa                                36

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 7
gtcagataac tgtccatgac                                                  20

<210> SEQ ID NO 8
<211> LENGTH: 39
<212> TYPE: DNA
<213> ORGANISM: Artificial Sequence
<220> FEATURE:
<223> OTHER INFORMATION: Synthetic Oligomer

<400> SEQUENCE: 8
aatttaatac gactcactat agggagauag cuuaucaga                             39

<210> SEQ ID NO 9
<211> LENGTH: 39
<212> TYPE: DNA
<213> ORGANISM: Artificial Sequence
<220> FEATURE:
```

<223> OTHER INFORMATION: Synthetic Oligomer

<400> SEQUENCE: 9
aatttaatac gactcactat agggagatag gcagtgtca                                      39

<210> SEQ ID NO 10
<211> LENGTH: 39
<212> TYPE: DNA
<213> ORGANISM: Artificial Sequence
<220> FEATURE:
<223> OTHER INFORMATION: Synthetic Oligomer

<400> SEQUENCE: 10
aatttaatac gactcactat agggagattt ggcaatggt                                      39

<210> SEQ ID NO 11
<211> LENGTH: 53
<212> TYPE: DNA
<213> ORGANISM: Artificial Sequence
<220> FEATURE:
<223> OTHER INFORMATION: Synthetic Oligomer

<400> SEQUENCE: 11
aatttaatac gactcactat agggagacca caacggttta gcuacauugu cug                      53

<210> SEQ ID NO 12
<211> LENGTH: 39
<212> TYPE: DNA
<213> ORGANISM: Artificial Sequence
<220> FEATURE:
<223> OTHER INFORMATION: Synthetic Oligomer

<400> SEQUENCE: 12
aatttaatac gactcactat agggagaagc uacaucugg                                      39

<210> SEQ ID NO 13
<211> LENGTH: 39
<212> TYPE: DNA
<213> ORGANISM: Artificial Sequence
<220> FEATURE:
<223> OTHER INFORMATION: Synthetic Oligomer

<400> SEQUENCE: 13
aatttaatac gactcactat agggagacag taacaaaga                                      39

<210> SEQ ID NO 14
<211> LENGTH: 55
<212> TYPE: DNA
<213> ORGANISM: Artificial Sequence
<220> FEATURE:
<223> OTHER INFORMATION: Synthetic Oligomer

<400> SEQUENCE: 14
cggtcgcaga gattaactgg tacagggtta agcgtggtcg accgtcaaca tcagt                    55

<210> SEQ ID NO 15
<211> LENGTH: 56
<212> TYPE: DNA
<213> ORGANISM: Artificial Sequence
<220> FEATURE:
<223> OTHER INFORMATION: Synthetic Oligomer

<400> SEQUENCE: 15
cggtcgcaga gattaactgg tacagggtta agcgtggtcg accgcaatca gctaat                   56

<210> SEQ ID NO 16

```
<211> LENGTH: 56
<212> TYPE: DNA
<213> ORGANISM: Artificial Sequence
<220> FEATURE:
<223> OTHER INFORMATION: Synthetic Oligomer

<400> SEQUENCE: 16
cggtcgcaga gattaactgg tacagggtta agcgtggtcg accgagtgtg agttct        56

<210> SEQ ID NO 17
<211> LENGTH: 56
<212> TYPE: DNA
<213> ORGANISM: Artificial Sequence
<220> FEATURE:
<223> OTHER INFORMATION: Synthetic Oligomer

<400> SEQUENCE: 17
cggtcgcaga gattaactgg tacagggtta agcgtggtcg accggaaacc cagcag        56

<210> SEQ ID NO 18
<211> LENGTH: 56
<212> TYPE: DNA
<213> ORGANISM: Artificial Sequence
<220> FEATURE:
<223> OTHER INFORMATION: Synthetic Oligomer

<400> SEQUENCE: 18
cggtcgcaga gattaactgg tacagggtta agcgtggtcg accggagacc cagtag        56

<210> SEQ ID NO 19
<211> LENGTH: 56
<212> TYPE: DNA
<213> ORGANISM: Artificial Sequence
<220> FEATURE:
<223> OTHER INFORMATION: Synthetic Oligomer

<400> SEQUENCE: 19
cggtcgcaga gattaactgg tacagggtta agcgtggtcg accgacaagg atgaat        56

<210> SEQ ID NO 20
<211> LENGTH: 18
<212> TYPE: DNA
<213> ORGANISM: Artificial Sequence
<220> FEATURE:
<223> OTHER INFORMATION: Synthetic Oligomer

<400> SEQUENCE: 20
cggucgcaga gattaact                                                  18

<210> SEQ ID NO 21
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 21
ccgacaagcg uggucgacgu cgg                                            23

<210> SEQ ID NO 22
<211> LENGTH: 46
<212> TYPE: DNA
<213> ORGANISM: Artificial Sequence
<220> FEATURE:
<223> OTHER INFORMATION: Synthetic Oligomer

<400> SEQUENCE: 22
```

```
tttttttttt ttcaacauc agucugauaa gcuaaaaaaa aaaaaa                46
```

<210> SEQ ID NO 23
<211> LENGTH: 48
<212> TYPE: DNA
<213> ORGANISM: Artificial Sequence
<220> FEATURE:
<223> OTHER INFORMATION: Synthetic Oligomer

<400> SEQUENCE: 23

```
tttttttttt ttagugugag uucuaccauu gccaaaaaaa aaaaaaaa             48
```

<210> SEQ ID NO 24
<211> LENGTH: 47
<212> TYPE: DNA
<213> ORGANISM: Artificial Sequence
<220> FEATURE:
<223> OTHER INFORMATION: Synthetic Oligomer

<400> SEQUENCE: 24

```
tttttttttt ttgaaaccca gcagacaaug uagcuaaaaa aaaaaaa              47
```

<210> SEQ ID NO 25
<211> LENGTH: 45
<212> TYPE: DNA
<213> ORGANISM: Artificial Sequence
<220> FEATURE:
<223> OTHER INFORMATION: Synthetic Oligomer

<400> SEQUENCE: 25

```
tttttttttt ttacccagua gccagaugua gcuaaaaaaa aaaaa                45
```

<210> SEQ ID NO 26
<211> LENGTH: 47
<212> TYPE: DNA
<213> ORGANISM: Artificial Sequence
<220> FEATURE:
<223> OTHER INFORMATION: Synthetic Oligomer

<400> SEQUENCE: 26

```
tttttttttt ttacaaggau gaaucuuugu uacugaaaaa aaaaaaa              47
```

<210> SEQ ID NO 27
<211> LENGTH: 22
<212> TYPE: RNA
<213> ORGANISM: Homo sapiens

<400> SEQUENCE: 27

```
agagguagua gguugcauag uu                                         22
```

<210> SEQ ID NO 28
<211> LENGTH: 84
<212> TYPE: RNA
<213> ORGANISM: Homo sapiens

<400> SEQUENCE: 28

```
gugcucgguu uguaggcagu gucauuagcu gauuguacug uggugguuac aaucacuaac    60
uccacugcca ucaaaacaag gcac                                           84
```

<210> SEQ ID NO 29
<211> LENGTH: 22
<212> TYPE: RNA
<213> ORGANISM: Homo sapiens

<400> SEQUENCE: 29

| | |
|---|---|
| caaucacuaa cuccacugcc au | 22 |

<210> SEQ ID NO 30
<211> LENGTH: 23
<212> TYPE: RNA
<213> ORGANISM: Homo sapiens

<400> SEQUENCE: 30

| | |
|---|---|
| uaggcagugu cauuagcuga uug | 23 |

<210> SEQ ID NO 31
<211> LENGTH: 22
<212> TYPE: RNA
<213> ORGANISM: Homo sapiens

<400> SEQUENCE: 31

| | |
|---|---|
| aaaaguaauu gugguuuuug cc | 22 |

<210> SEQ ID NO 32
<211> LENGTH: 22
<212> TYPE: RNA
<213> ORGANISM: Homo sapiens

<400> SEQUENCE: 32

| | |
|---|---|
| caaaaaccac aguuucuuuu gc | 22 |

<210> SEQ ID NO 33
<211> LENGTH: 94
<212> TYPE: RNA
<213> ORGANISM: Homo sapiens

<400> SEQUENCE: 33

| | |
|---|---|
| guucuguuau uugcagucag uaacaaagau ucauccuugu guccaucaug caacaaggag | 60 |
| aaucuuuguc acuuagugua auuaauagcu ggac | 94 |

<210> SEQ ID NO 34
<211> LENGTH: 23
<212> TYPE: RNA
<213> ORGANISM: Homo sapiens

<400> SEQUENCE: 34

| | |
|---|---|
| caguaacaaa gauucauccu ugu | 23 |

<210> SEQ ID NO 35
<211> LENGTH: 22
<212> TYPE: RNA
<213> ORGANISM: Homo sapiens

<400> SEQUENCE: 35

| | |
|---|---|
| uggcaguguc uuagcugguu gu | 22 |

<210> SEQ ID NO 36
<211> LENGTH: 23
<212> TYPE: RNA
<213> ORGANISM: Homo sapiens

<400> SEQUENCE: 36

| | |
|---|---|
| aggcagugua guuagcugau ugc | 23 |

<210> SEQ ID NO 37
<211> LENGTH: 72
<212> TYPE: RNA
<213> ORGANISM: Homo sapiens

```
<400> SEQUENCE: 37
ugucggguag cuuaucagac ugauguugac uguugaaucu cauggcaaca ccagucgaug      60
ggcugucuga ca                                                          72

<210> SEQ ID NO 38
<211> LENGTH: 22
<212> TYPE: RNA
<213> ORGANISM: Homo sapiens

<400> SEQUENCE: 38
uagcuuauca gacugauguu ga                                               22

<210> SEQ ID NO 39
<211> LENGTH: 21
<212> TYPE: RNA
<213> ORGANISM: Homo sapiens

<400> SEQUENCE: 39
caacaccagu cgaugggcug u                                                21

<210> SEQ ID NO 40
<211> LENGTH: 110
<212> TYPE: RNA
<213> ORGANISM: Homo sapiens

<400> SEQUENCE: 40
gagcugcuug ccucccccg uuuuggcaa ugguagaacu cacacuggug agguaacagg        60
auccgguggu ucuagacuug ccaacuaugg ggcgaggacu cagccggcac                110

<210> SEQ ID NO 41
<211> LENGTH: 24
<212> TYPE: RNA
<213> ORGANISM: Homo sapiens

<400> SEQUENCE: 41
uuuggcaaug guagaacuca cacu                                             24

<210> SEQ ID NO 42
<211> LENGTH: 21
<212> TYPE: RNA
<213> ORGANISM: Homo sapiens

<400> SEQUENCE: 42
ugguucuaga cuugccaacu a                                                21

<210> SEQ ID NO 43
<211> LENGTH: 110
<212> TYPE: RNA
<213> ORGANISM: Homo sapiens

<400> SEQUENCE: 43
ugaacaucca ggucggggc augaaccugg cauacaaugu agauuucugu guucguuagg       60
caacagcuac auugucugcu ggguuucagg cuaccuggaa acauguucuc                110

<210> SEQ ID NO 44
<211> LENGTH: 23
<212> TYPE: RNA
<213> ORGANISM: Homo sapiens

<400> SEQUENCE: 44
agcuacauug ucugcuggu uuc                                               23
```

```
<210> SEQ ID NO 45
<211> LENGTH: 22
<212> TYPE: RNA
<213> ORGANISM: Homo sapiens

<400> SEQUENCE: 45
accuggcaua caauguagau uu                                              22

<210> SEQ ID NO 46
<211> LENGTH: 110
<212> TYPE: RNA
<213> ORGANISM: Homo sapiens

<400> SEQUENCE: 46
gcugcuggaa gguguaggua cccucaaugg cucaguagcc aguguagauc cugucuuucg     60
uaaucagcag cuacaucugg cuacuggguc ucgauggca ucuucuagcu                110

<210> SEQ ID NO 47
<211> LENGTH: 21
<212> TYPE: RNA
<213> ORGANISM: Homo sapiens

<400> SEQUENCE: 47
agcuacaucu ggcuacuggg u                                               21

<210> SEQ ID NO 48
<211> LENGTH: 22
<212> TYPE: RNA
<213> ORGANISM: Homo sapiens

<400> SEQUENCE: 48
cucaguagcc aguguagauc cu                                              22

<210> SEQ ID NO 49
<211> LENGTH: 43
<212> TYPE: DNA
<213> ORGANISM: Artificial Sequence
<220> FEATURE:
<223> OTHER INFORMATION: Synthetic Oligomer

<400> SEQUENCE: 49
cggtcgcaga gattaactgg tacagggtta agcgtggtcg acc                       43

<210> SEQ ID NO 50
<211> LENGTH: 22
<212> TYPE: RNA
<213> ORGANISM: Homo sapiens

<400> SEQUENCE: 50
uguaaacauc cuacacucag cu                                              22
```

COMPOSITIONS AND METHODS FOR DETECTING SMALL RNAS, AND USES THEREOF

RELATED APPLICATION

This application claims the benefit under 35 U.S.C. 119(e) of provisional application No. 61/117,913, filed Nov. 25, 2008, which is incorporated by reference herein.

FIELD OF THE INVENTION

The invention is related to the field of nucleic acid assays, and particularly to detection of specific target small nucleic acid present in a sample, such a small RNA or DNA sequence present in a biological sample.

BACKGROUND

Detection of nucleic acids in a sample is useful in diagnostic, therapeutic, forensic, agricultural, food science applications and other areas. Methods of nucleic acid detection generally include those that use physical separation of a nucleic acid, such as by capturing the nucleic acid in or on a matrix or support followed by detecting the presence of captured nucleic acids and/or amplification products made therefrom. Detection can take place by a number of methods known in the art, such as mass spectrometry, sequencing, a dye or intercalating agent, or by hybridizing a detectable probe to the nucleic acid. Some methods indirectly detect nucleic acids by producing a product made from using a target nucleic acid as a template and detecting the product, e.g., detecting an RNA transcript made from a DNA, or a translated protein made from an RNA transcript. Other indirect methods detect a product made by an enzymatic reaction associated with the nucleic acid to be detected, e.g., an enzyme-linked probe hybridized to the target nucleic acid which produces a detectable response when the enzyme's substrate is provided. Some methods of nucleic acid detection rely on amplifying a nucleic acid sequence to produce a larger quantity of nucleic acid that is detected. Examples of amplification methods include producing many copies of a cloned sequence and in vitro amplification procedures that use enzymatic synthesis of multiple copies of a nucleic acid sequence.

Many of the techniques for detecting nucleic acids require the presence of a relatively large amount or proportion of the target nucleic acid in the sample, while other techniques use nucleic acid amplification to increase the amount or proportion of the nucleic acid to be detected from a smaller amount of the target nucleic acid in a sample. Enrichment of some or all of the nucleic acid present in a sample may facilitate detection of the nucleic acid of interest. Many known procedures for nucleic acid enrichment and detection are laborious, time-consuming, or require use of equipment or hazardous chemicals (e.g., chaotropes, mutagens, or radioactive compounds) that make such procedures undesirable for many applications, such as for rapid screening of many samples, point-of-care diagnostics, or detection at a site outside of a laboratory. Thus, there remains a need for a method that provides relatively simple procedures and sufficient sensitivity and/or specificity to detect a nucleic acid of interest.

The physical nature or relative abundance of some nucleic acids may impede their detection in a sample. For example, small RNA (about 17-27 nt), such as microRNA (miRNA), small or short interfering RNA (siRNA), short hairpin RNA (shRNA), and small nuclear RNA (snRNA) are difficult to separate from other sample components and/or to detect by using known methods. Small RNA are often relatively rare in a biological sample, which contributes to the difficulty of their detection. Further complicating the detection of these small RNA molecules is that these short template RNA species often share high sequence homology between closely related family members. Most small RNA detection methods in the art use general RNA isolation techniques, like Invitrogen Trizol reagent, Stratagene Total RNA, ABI mirVana and ABI Total RNA, (Invitrogen, Carlsbad, Calif.; Stratagene, La Jolla, Calif.; ABI, Foster City Calif.), all of which provide an indiscriminant abundance of RNA species that may include the target small RNA molecule(s) and include many other non-target nucleic acids. These non-target nucleic acids often interfere with analysis of target sequence. These one size fits all approaches introduce bias and experimental error into small RNA expression profiling experiments. Because small RNA are regulatory molecules that modulate or silence gene expression via RNA interference (RNAi), they are important molecules for understanding biological processes and disease states and as disease preventive or therapeutic agents. Studies have shown that differential small RNA expression occurs in cancerous and non-cancerous cells. Thus, there is a need for compositions and methods that rapidly and accurately isolate small RNA from a sample for downstream analysis. There is a need to rapidly and accurately isolate and detect the presence of one or more small RNA in biological samples to determine their abundance, relative abundance, expression level, stability, therapeutic efficacy, or other characteristics in a biological sample. There is a further need to rapidly and accurately detect relative amounts of differentially expressed small RNA in a variety of biological samples as an indicator of a cancerous condition and/or as a part of a cancer prognosis by determining metastatic potential of a tumor and in developing a suitable treatment thereof.

Current methods for detecting small RNA in biological samples are time consuming and imprecise. Common techniques include PCR (RT and qRT), in situ hybridization, nuclease protection assays, Northern blots to detect RNA, Western blots, immunoassays, and fluorescence detection assays (PCT App. Nos. WO 00/44914, Li et al., WO 05/04794, Bumcrot et al.). Detection methods also exist wherein an additional sequences is added to the small RNA to facilitate priming and detection, such as adding a single universal extension primer or adapter to every miRNA in a sample (Chen et al. U.S. Pat. No. 7,601,495; Raymond et al. RNA, 11:1737-44 (2005)). These added nucleic acid sequences are then used as primer binding sites for amplification of the small RNA and/or as capture probe-binding sites, (Mullinax et al., US Pat. Pub. No. 2008-0182235; Jacobsen et al. WO 05/098029). In addition, these added nucleic acid sequences can be used as primers for a first amplification (Chen et al. Nuc. Acid. Res., 33(20):e179 (2005)). Another method for amplifying and detecting a small RNA includes using a bridging oligo that is complementary to both a small RNA molecules and a unique nucleic acid molecule followed by a ligating step to join the small RNA and the unique nucleic acid (Yeakley, US Pat. Pub. No. 2006-0019258). These methods, unfortunately, are inaccurate; particularly as throughput increases so too does the variability in result data (e.g., Mestdagh, Chen et al. Nuc. Acid. Res. 36(21):e143 (2008) and Nelson et al., Biochim. Biophys Acta, 1179(11):758-65 (2008)). Thus, the methods in the art are not fully sufficient for providing reliable small RNA expression data for use in diagnosing disorders in which one or more of these small RNAs play a role. Moreover, sample-processing methods in the art are crude and inadequate for sample-to-answer automation, for identifying high throughput processing of a large number of specimens, particularly for biomarker validation and diagnostic applications. There is a need for a method for accurately detecting the presence and relative abundance of one or more small RNAs in a sample for diagnosing and monitoring a disorder, as well as for prognosing the disorder and/or monitoring the efficacy of a treatment of the disorder. There is also a need for methods and reagents useful with high throughput analysis of and diagnostics using biomarkers, such as small RNA.

This application responds to the need for rapid, accurate and efficient nucleic acid detection assays by disclosing methods and compositions useful for the isolation and detection of one or more nucleic acids in samples, including one or more small RNA in biological samples, and that are amenable with fully automated platforms.

SUMMARY OF THE INVENTION

An aspect of the invention is a method of detecting the presence of a nucleic acid present in a sample which includes the steps of: providing a sample containing a small RNA target nucleic acid that is a micro RNA, miR-21, miR-34b, miR-182, miR-221, miR-222 or miR-802, mixing the sample with a nucleic acid capture probe that forms under hybridizing conditions a partially double-stranded hairpin structure made up of an internal target hybridizing sequence, flanked by a capture region, and a terminal region that binds to the capture region to form a double-stranded stem portion of the hairpin structure in which the target hybridizing region forms a substantially single-stranded loop portion, specifically hybridizing the target hybridizing sequence of the capture probe to a target sequence in the target nucleic acid, binding the capture region to an immobilized probe attached to a capture support by binding together members of a specific binding pair, thereby forming a capture hybrid made up of the target nucleic acid, the capture probe, and the immobilized probe attached to the capture support, separating the capture hybrid attached to the capture support from sample components, releasing the target nucleic acid from the capture hybrid, then specifically hybridizing a detection probe to the target nucleic to form a detection hybrid, and detecting a signal produced from the detection hybrid to indicate the presence of the target nucleic acid in the sample. In one embodiment, the capture region is located near the 3' end of the capture probe and the terminal region is located near the 5' end of the capture probe. In another embodiment, the capture region is located near the 5' end of the capture probe and the terminal region is located near the 3' end of the capture probe. In one embodiment, the step of binding the capture region to the immobilized probe hybridizes complementary sequences of the capture region and the immobilized probe. In another embodiment, binding the capture region to the immobilized probe binds together non-nucleic acid members of a specific binding pair, such as a ligand and its receptor. In one embodiment, releasing the target nucleic acid from the capture hybrid further releases the capture probe from the immobilized probe. In one embodiment, an amplification step uses a first amplification oligomer that specifically hybridizes to all or a portion of the same target sequence that the target capture probe hybridizes. In one embodiment, an amplification step uses a promoter based amplification oligomer that specifically hybridizes to a target sequence that is complementary to all or a portion of the target sequence that the target capture probe hybridizes. In one embodiment, the detecting step uses a detection probe that hybridizes specifically to a target sequence that is the same target sequence that hybridizes to the target hybridizing sequence of the capture probe. In another embodiment, the detection probe hybridizes specifically to a target sequence that differs from or overlaps the target sequence that hybridizes to the target hybridizing sequence of the capture probe. In a preferred embodiment, the detecting step detects a signal is produced in a homogeneous reaction.

Another aspect of the invention is a method of detecting the presence of a target nucleic acid present in a sample that includes the steps of: providing a sample containing a small RNA target nucleic acid that is a micro RNA, miR-21, miR-34b, miR-182, miR-221, miR-222 or miR-802, mixing the sample with a capture probe that is at least a partially double-stranded structure made up of a first strand and a second strand of nucleic acid, wherein the first strand includes a target hybridizing region and a capture region, and the second strand contains a sequence complementary to a sequence of the first strand, specifically hybridizing the target hybridizing region of the capture probe to a target sequence in the target nucleic acid, binding the capture region to an immobilized probe attached to a capture support, thereby forming a capture hybrid made up of the target nucleic acid, the first strand of the capture probe, and the immobilized probe attached to the capture support, separating the capture hybrid attached to the capture support from other sample components, releasing the target nucleic acid from the capture hybrid, then specifically hybridizing a detection probe to the target nucleic acid to form a detection hybrid, and detecting a signal produced from the detection hybrid, thereby indicating the presence of the target nucleic acid in the sample. In one embodiment, the first strand Contains a 5' capture region covalently linked to a 3' target hybridizing region, and the second strand contains a 3' sequence complementary to the capture region of the first strand, thereby forming a partially double-stranded structure when the capture region of the first strand hybridizes to the complementary 3' sequence of the second strand. In another embodiment, the first strand contains a 5' target hybridizing region covalently linked to a 3' capture region, and the second strand contains a 5' sequence complementary to the 3' capture region of the first strand, thereby forming a partially double-stranded structure when the capture region of the first strand hybridizes to the complementary 5' sequence of the second strand. In one embodiment, an amplification step uses a first amplification oligomer that specifically hybridizes to all or a portion of the same target sequence that the target capture probe hybridizes. In one embodiment, an amplification step uses a promoter based amplification oligomer that specifically hybridizes to a target sequence that is complementary to all or a portion of the target sequence that the target capture probe hybridizes.

Another aspect of the invention is a nucleic acid capture probe that forms at least a partially double-stranded structure under hybridizing conditions and includes a target hybridizing sequence and a capture region that binds to an immobilized probe by using members of a specific binding pair. In one embodiment, the partially double-stranded structure is a hairpin structure made up of a contiguous linear sequence that includes an internal target hybridizing sequence, flanked by the capture region and a terminal region that binds to the capture region to form a double-stranded stem portion of the hairpin structure and the target hybridizing region forms a substantially single-stranded loop portion of the hairpin structure. It will be appreciated that the capture region may be a 5' region and the terminal region is a 3' region of the contiguous linear sequence, or alternatively, the capture region may be a 5' region and the terminal region is a 3' region of the contiguous linear sequence that forms a hairpin structure. In another capture probe embodiment, the structure is made of up of a first strand that includes the target hybridizing region and the capture region, and a separate second strand that includes a sequence complementary to a sequence of the first strand such that hybridization of the complementary sequences of the first strand and second strand produce at least a partially double-stranded structure. It will be appreciated that the first strand may have a 5' target hybridizing region and a 3' capture region, or alternatively, a 3' target hybridizing region and a 5' capture region, and that the complementary sequence of the separate second strand may be complementary to either the target hybridizing region or the capture region of the first strand. In a preferred embodiment, the complementary sequence of the second strand is complementary to the capture region of the first strand.

One embodiment is a method of detecting the presence of a target nucleic acid in a sample comprising the steps of: providing a target capture probe that forms under hybridizing conditions a partially double-stranded hairpin structure made up of an internal target hybridizing sequence flanked by a capture region and a terminal region, wherein the terminal region binds to the capture region to form a double-stranded stem portion of the hairpin structure, and wherein the target hybridizing region forms a single-stranded loop portion of the hairpin structure; mixing a sample suspected of containing a small RNA, miR21, miR-34b, miR-182, miR-221, miR-222 or miR-802 target nucleic acid with the capture probe; specifically hybridizing the target hybridizing sequence of the capture probe to a target sequence in the small RNA, miR21, miR-34b, miR-182, miR-221, miR-222 or miR-802 target nucleic acid; binding the capture region to an immobilized probe attached to a capture support by binding together members of a specific binding pair, thereby forming a capture hybrid made up of the small RNA, miR21, miR-34b, miR-182, miR-221, miR-222 or miR-802 target nucleic acid, the capture probe, and the immobilized probe attached to the capture support; separating the capture hybrid attached to the capture support from other components in the sample; releasing the small RNA, miR21, miR-34b, miR-182, miR-221, miR-222 or miR-802 target nucleic acid from the capture hybrid; providing to the mixture comprising the released small RNA, miR21, miR-34b, miR-182, miR-221, miR-222 or miR-802 target nucleic acid and the target capture probe at least a first amplification oligomer comprising a target hybridizing sequence, a portion of which is substantially identical to a portion of the target hybridizing region of the target capture probe; providing a set of conditions wherein the first amplification oligomer hybridizes to the small RNA, miR21, miR-34b, miR-182, miR-221, miR-222 or miR-802 target nucleic acid and an amplification reaction takes place, and wherein the target capture probe is in a partially double stranded hairpin formation; generating a detectable amplification product in an amplification reaction wherein the first amplification oligomer generates a cDNA strand from the small RNA, miR21, miR-34b, miR-182, miR-221, miR-222 or miR-802 target nucleic acid; and detecting the amplification product to indicate presence of small RNA, miR21, miR-34b, miR-182, miR-221, miR-222 or miR-802 target nucleic acid in the sample.

Another embodiment is a method of detecting the presence of a target nucleic acid in a sample comprising the steps of: providing a target capture probe that forms under hybridizing conditions a partially double-stranded hairpin structure made up of an internal target hybridizing sequence flanked by a capture region and a terminal region, wherein the terminal region binds to the capture region to form a double-stranded stem portion of the hairpin structure, and wherein the target hybridizing region forms a single-stranded loop portion of the hairpin structure; mixing a sample suspected of containing a small RNA, miR21, miR-34b, miR-182, miR-221, miR-222 or miR-802 target nucleic acid with the capture probe; specifically hybridizing the target hybridizing sequence of the capture probe to a target sequence in the miR-221 target nucleic acid; binding the capture region to an immobilized probe attached to a capture support by binding together members of a specific binding pair, thereby forming a capture hybrid made up of the small RNA, miR21, miR-34b, miR-182, miR-221, miR-222 or miR-802 target nucleic acid, the capture probe, and the immobilized probe attached to the capture support; separating the capture hybrid attached to the capture support from other components in the sample; releasing the small RNA, miR21, miR-34b, miR-182, miR-221, miR-222 or miR-802 target nucleic acid from the capture hybrid and providing a set of conditions wherein the target capture probe is a partially double-stranded hairpin structure; providing to the mixture comprising the released small RNA, miR21, miR-34b, miR-182, miR-221, miR-222 or miR-802 target nucleic acid and the target capture probe a plurality of amplification oligomers, the plurality comprising at least a first amplification oligomer and a promoter-based oligomer, wherein the first amplification oligomer comprises a target hybridizing sequence, a portion of which is substantially identical to a portion of the target hybridizing region of the target capture probe, and wherein the promoter-based oligomer comprises a target hybridizing sequence, a portion of which is substantially complementary to a portion of the target hybridizing region of the target capture probe; providing a set of conditions wherein the first amplification oligomer hybridizes to the small RNA, miR21, miR-34b, miR-182, miR-221, miR-222 or miR-802 target nucleic acid in the presence of the hairpin capture probe; performing an amplification reaction using the plurality of amplification oligomers to generate amplification product from the small RNA, miR21, miR-34b, miR-182, miR-221, miR-222 or miR-802 target nucleic acid; and detecting the amplification product to indicate presence of small RNA, miR21, miR-34b, miR-182, miR-221, miR-222 or miR-802 target nucleic acid in the sample.

Another embodiment is a multiplex amplification method for specifically detecting the presence of target nucleic acids in a sample comprising the steps of: providing a first target capture probe for capturing a small RNA, miR21, miR-34b, miR-182, miR-221, miR-222 or miR-802 target nucleic acid and a second target capture probe for capturing a small RNA, miR21, miR-34b, miR-182, miR-221, miR-222 or miR-802 target nucleic acid, wherein the target capture probes are configured to target different target nucleic acids, wherein the target capture probes are each made up of an internal target hybridizing sequence flanked by a capture region and a terminal region, wherein the terminal region binds to the capture region to form a double-stranded stem portion of the hairpin structure, wherein the target hybridizing sequence forms a single-stranded loop portion of the hairpin structure, and wherein the target hybridizing sequence of the capture probe is substantially complementary to all or a portion of a small RNA, miR21, miR-34b, miR-182, miR-221, miR-222 or miR-802 sequence and target hybridizing sequence of the miR-182 target capture probe is substantially complementary to all or a portion of a small RNA, miR21, miR-34b, miR-182, miR-221, miR-222 or miR-802; mixing a sample suspected of containing two or more of a small RNA, miR21, miR-34b, miR-182, miR-221, miR-222 or miR-802 target nucleic acid with the capture probes; specifically hybridizing the target hybridizing sequence of the capture probes to a target sequence in their respective target nucleic acids; binding the capture regions to an immobilized probe attached to a capture support by binding together members of a specific binding pair, thereby forming capture hybrids made up of the small RNA, miR21, miR-34b, miR-182, miR-221, miR-222 or miR-802 target nucleic acid, the first capture probe and the immobilized probe attached to the capture support, and another capture hybrid made up of small RNA, miR21, miR-34b, miR-182, miR-221, miR-222 or miR-802 target nucleic acid, the second capture probe, and the immobilized probe attached to the capture support; separating the capture hybrids from other components in the sample; releasing the target nucleic acids from their capture hybrids and providing a set of conditions wherein the first and second target capture probes are partially double-stranded hairpin structures; providing to the mixture comprising the released target nucleic acids and the target capture probes a plurality of amplification oligomers, the plurality comprising, (i) at least a first amplification oligomer and a promoter-based oligomer for specifically hybridizing to small RNA, miR21, miR-34b, miR-182, miR-221, miR-222 or miR-802 target nucleic acid captured by the first target capture probe or cDNA strand thereof, wherein the first amplification oligomer comprises a target hybridizing sequence, a portion of which is substantially identical to a portion of the target hybridizing region of the first target capture probe, and wherein the promoter-based oligomer comprises a target hybridizing sequence, a portion of which is substantially complementary to a portion of the target hybridizing region of the first target capture probe, and (ii) at least a first amplification oligomer and a promoter-based oligomer for hybridizing to a small RNA, miR21, miR-34b, miR-182, miR-221, miR-222 or miR-802 target nucleic acid captured by the second target capture probe or cDNA strand thereof, wherein the first amplification oligomer comprises a target hybridizing sequence, a portion of which is substantially identical to a portion of the target hybridizing region of the second target capture probe, and wherein the promoter-based oligomer comprises a target hybridizing sequence, a portion of which is substantially complementary to a portion of the target hybridizing region of the second target capture probe; providing a set of conditions wherein the first amplification oligomers hybridize to their respective target nucleic acids; performing an amplification reaction using the plurality of amplification oligomers to generate amplification products from the small RNA, miR21, miR-34b, miR-182, miR-221, miR-222 or miR-802 and miR-182 target nucleic acids captured by the first and second target capture probes; and detecting the amplification products to indicate presence of a small RNA, miR21, miR-34b, miR-182, miR-221, miR-222 or miR-802 target nucleic acid captured by the first target capture probe, and small RNA, miR21, miR-34b, miR-182, miR-221, miR-222 or miR-802 target nucleic acid captured by the first target capture probe or both in the sample. The multiplex methods can similarly include more than two target nucleic acids, and the oligomers used will increase accordingly.

Another embodiment is a method of detecting the presence of a target nucleic acid in a sample comprising the steps of: providing a target capture probe that forms under hybridizing conditions a partially double-stranded hairpin structure made up of an internal target hybridizing sequence flanked by a capture region and a terminal region, wherein the terminal region binds to the capture region to form a double-stranded stem portion of the hairpin structure, and wherein the target hybridizing region forms a single-stranded loop portion of the hairpin structure; mixing a sample suspected of containing a miR-221 target nucleic acid with the capture probe; specifically hybridizing the target hybridizing sequence of the capture probe to a target sequence in the miR-221 target nucleic acid; binding the capture region to an immobilized probe attached to a capture support by binding together members of a specific binding pair, thereby forming a capture hybrid made up of the miR-221 target nucleic acid, the capture probe, and the immobilized probe attached to the capture support; separating the capture hybrid attached to the capture support from other components in the sample; releasing the miR-221 target nucleic acid from the capture hybrid; providing to the mixture comprising the released miR-221 target nucleic acid and the target capture probe at least a first amplification oligomer comprising a target hybridizing sequence, a portion of which is substantially identical to a portion of the target hybridizing region of the target capture probe; providing a set of conditions wherein the first amplification oligomer hybridizes to the miR-221 target nucleic acid and an amplification reaction takes place, and wherein the target capture probe is in a partially double stranded hairpin formation; generating a detectable amplification product in an amplification reaction wherein the first amplification oligomer generates a cDNA strand from the miR-221 target nucleic acid; and detecting the amplification product to indicate presence of miR-221 target nucleic acid in the sample.

Another embodiment is a method of detecting the presence of a target nucleic acid in a sample comprising the steps of: providing a target capture probe that forms under hybridizing conditions a partially double-stranded hairpin structure made up of an internal target hybridizing sequence flanked by a capture region and a terminal region, wherein the terminal region binds to the capture region to form a double-stranded stem portion of the hairpin structure, and wherein the target hybridizing region forms a single-stranded loop portion of the hairpin structure; mixing a sample suspected of containing a miR-221 target nucleic acid with the capture probe; specifically hybridizing the target hybridizing sequence of the capture probe to a target sequence in the miR-221 target nucleic acid; binding the capture region to an immobilized probe attached to a capture support by binding together members of a specific binding pair, thereby forming a capture hybrid made up of the miR-221 target nucleic acid, the capture probe, and the immobilized probe attached to the capture support; separating the capture hybrid attached to the capture support from other components in the sample; releasing the miR-221 target nucleic acid from the capture hybrid and providing a set of conditions wherein the target capture probe is a partially double-stranded hairpin structure; providing to the mixture comprising the released miR-221 target nucleic acid and the target capture probe a plurality of amplification oligomers, the plurality comprising at least a first amplification oligomer and a promoter-based oligomer, wherein the first amplification oligomer comprises a target hybridizing sequence, a portion of which is substantially identical to a portion of the target hybridizing region of the target capture probe, and wherein the promoter-based oligomer comprises a target hybridizing sequence, a portion of which is substantially complementary to a portion of the target hybridizing region of the target capture probe; providing a set of conditions wherein the first amplification oligomer hybridizes to the miR-221 target nucleic acid in the presence of the hairpin capture probe; performing an amplification reaction using the plurality of amplification oligomers to generate amplification product from the miR-221 target nucleic acid; and detecting the amplification product to indicate presence of miR-221 target nucleic acid in the sample.

Another embodiment is a multiplex amplification method for specifically detecting the presence of target nucleic acids in a sample comprising the steps of: providing a target capture probe for capturing a miR-221 target nucleic acid and a target capture probe for capturing a miR-182 target nucleic acid, wherein the target capture probes are each made up of an internal target hybridizing sequence flanked by a capture region and a terminal region, wherein the terminal region binds to the capture region to form a double-stranded stem portion of the hairpin structure, wherein the target hybridizing region forms a single-stranded loop portion of the hairpin structure, and wherein the target capture region of the miR-221 target capture probe is substantially complementary to all or a portion of a miR-221 sequence and the target capture region of the miR-182 target capture probe is substantially complementary to all or a portion of a miR-182 sequence; mixing a sample suspected of containing a miR-221 target nucleic acid and a miR-182 target nucleic acid with the capture probes; specifically hybridizing the target hybridizing sequence of the capture probes to a target sequence in their respective target nucleic acids; binding the capture regions to an immobilized probe attached to a capture support by binding together members of a specific binding pair, thereby forming a capture hybrid made up of the miR-221 target nucleic acid, the capture probe and the immobilized probe attached to the capture support, and a capture hybrid made up of the miR-182 target nucleic acid, the capture probe, and the immobilized probe attached to the capture support; separating the capture hybrids from other components in the sample; releasing the miR-221 and miR-182 target nucleic acids from the capture hybrids and providing a set of conditions wherein the target capture probes are partially double-stranded hairpin structures; providing to the mixture comprising the released miR-221 and miR-182 target nucleic acids and the target capture probes a plurality of amplification oligomers, the plurality comprising, (i) at least a first amplification oligomer and a promoter-based oligomer for specifically hybridizing to a miR-221 target nucleic acid or cDNA strand thereof, wherein the first amplification oligomer comprises a target hybridizing sequence, a portion of which is substantially identical to a portion of the target hybridizing region of the miR-221 target capture probe, and wherein the promoter-based oligomer comprises a target hybridizing sequence, a portion of which is substantially complementary to a portion of the target hybridizing region of the miR-221 target capture probe, and (ii) at least a first amplification oligomer and a promoter-based oligomer for hybridizing to a miR-182 target nucleic acid or cDNA strand thereof, wherein the first amplification oligomer comprises a target hybridizing sequence, a portion of which is substantially identical to a portion of the target hybridizing region of the miR-182 target capture probe, and wherein the promoter-based oligomer comprises a target hybridizing sequence, a portion of which is substantially complementary to a portion of the target hybridizing region of the miR-182 target capture probe; providing a set of conditions wherein the first amplification oligomers hybridizes to their respective target nucleic acids; performing an amplification reaction using the plurality of amplification oligomers to generate amplification products from the miR-221 and miR-182 target nucleic acids; and detecting the amplification products to indicate presence of miR-221 target nucleic acid, miR-182 target nucleic acid or both in the sample.

In some aspects of the methods the capture region is joined to the 3' end of the target capture probe target hybridizing sequence. In some aspects, the capture region is joined to the 5' end of the target capture probe target hybridizing sequence. In some aspects, binding the capture region to the immobilized probe results from hybridizing complementary sequences of the capture region and the immobilized probe. In some aspects, the capture region is a nucleotide sequence selected from the group consisting of: dT.sub.0-3 A.sub.10-30, which means that the polyT portion of the capture region is from 0 to 3 nucleotides in length and the polyA portion of the capture region is from 10 to 30 nucleotide in length. In some aspects, the capture region is dA.sub.12. In some aspects, the step of releasing the target nucleic acid from the capture hybrid further releases the capture probe from the immobilized probe.

In some aspects of the methods, the target capture probe specifically hybridizes to a small RNA target nucleic acid. In some aspects, the target capture probe specifically hybridizes to a miR-21, miR-34b, miR-182, miR-221, miR-222 or miR-802 target nucleic acid. In some aspects, target capture probe specifically hybridizes to a target nucleic acid and has a target hybridizing sequence that is at least 95% complementary to SEQ ID NO:44, 41, 47, 38, 29 or 34. In some aspects, the target capture probe specifically hybridizes to a miR-221 target nucleic acid and has a target hybridizing sequence that is at least 95% identical to SEQ ID NO:24. In some aspects, target capture probe specifically hybridizes to a miR-221 target nucleic acid and has a nucleotide sequence that is at least 95% complementary to SEQ ID NO:44. In some aspects, the target capture probe that specifically hybridizes to a miR-221 target nucleic acid is SEQ ID NO:24. In some aspects, the target capture probe that specifically hybridizes to a miR-21 target nucleic acid is SEQ ID NO:22. In some aspects, the target capture probe that specifically hybridizes to a miR-182 target nucleic acid is SEQ ID NO:23. In some aspects, the target capture probe that specifically hybridizes to a miR-222 target nucleic acid is SEQ ID NO:25. In some aspects, the target capture probe that specifically hybridizes to a miR-802 target nucleic acid is SEQ ID NO:26.

In some aspects of the methods the first amplification oligomer is an extender primer comprising a 3' target hybridizing sequence and a 5' extension nucleic acid sequence, wherein the 3' target hybridizing sequence is substantially complementary to about 9, 10, 11, 12, 13, 14, 15, 16, 17, 18, 19, 20, 21, 22, 23, 24, 25, 26, 27 or more contiguous nucleic acids at the 3' end of its respective target nucleic acid. In some aspects of the methods the first amplification oligomer is an extender primer comprising a 3' target hybridizing sequence and a 5' extension nucleic acid sequence, wherein the 3' target hybridizing sequence is substantially complementary to about 9, 10, 11, 12, 13, 14, 15, 16, 17, 18, 19, 20, 21, 22, 23, 24, 25, 26, 27 or more contiguous nucleic acids at the 3' end of its respective small RNA target nucleic acid. In some aspects of the methods the first amplification oligomer is an extender primer comprising a 3' target hybridizing sequence and a 5' extension nucleic acid sequence, wherein the 3' target hybridizing sequence is substantially complementary to about 9, 10, 11, 12, 13, 14, 15, 16, 17, 18, 19, 20, 21, 22, 23, 24, 25, 26, 27 or more contiguous nucleic acids at the 3' end a target nucleic acid that is a miR-21, miR-34b, miR-182, miR-221, miR-222 or miR-802. In some aspects, the first amplification oligomer has an extension nucleic acid sequence that is at least 95% identical to SEQ ID NO:49. In some aspects, the first amplification oligomer targets miR-221 and has an extension nucleic acid sequence that is at least 95% identical to SEQ ID NO:49. In some aspects, the first amplification oligomer targets miR-182 and has an extension nucleic acid sequence that is at least 95% identical to SEQ ID NO:49. In some aspects, the first amplification oligomer is an extender primer targeting a miR21, miR-34b, miR-182, miR-221, miR-222 or miR-802 target nucleic acid and comprises a 3' target hybridizing sequence and a 5' extension nucleic acid sequence, wherein the 3' target hybridizing sequence is substantially identical to about 9 or more contiguous nucleic acids at the 5' end of the target hybridizing sequence of a target capture probe targeting miR21, miR-34b, miR-182, miR-221, miR-222 or miR-802. In some aspects, the first amplification oligomer is an extender primer targeting miR-221 and comprising a 3' target hybridizing sequence and a 5' extension nucleic acid sequence, wherein the 3' target hybridizing sequence is substantially identical to about 9 or more contiguous nucleic acids at the 5' end of the target hybridizing sequence of the miR-221 target capture probe. In some aspects, the first amplification oligomer is an extender primer targeting miR-182 and comprising a 3' target hybridizing sequence and a 5' extension nucleic acid sequence, wherein the 3' target hybridizing sequence is substantially identical to about 9 or more contiguous nucleic acids at the 5' end of the target hybridizing sequence of the miR-182 target capture probe. In some aspects, the extension nucleic acid sequence is at least 95% identical to SEQ ID NO:49. In some aspects, the target capture oligomer is SEQ ID NO:24 and the first amplification oligomer is SEQ ID NO:17.

In some aspects of the methods, a promoter based oligomer and a reverse primer oligomer are provided to the mixture and participate in the amplification reaction. In some aspects, the promoter based oligomer comprises a target hybridizing sequence that is substantially complementary all or a portion of the nucleic acids on 3' end of the target capture probe target hybridizing region. In some aspects, the promoter based oligomer comprises a target hybridizing sequence that is substantially complementary to about 5, 6, 7, 8, 9, 10, 11, 12, 13, 14, 15, 16, 17, 18, 19, 20, 21, 22, 23, 24, 25, 26, 27 or more contiguous nucleic acids on 3' end of the target capture probe target hybridizing region. In some aspects, the promoter based oligomer comprises a target hybridizing sequence that is substantially complementary to about 5, 6, 7, 8, 9, 10, 11, 12, 13, 14, 15, 16, 17, 18, 19, 20, 21, 22, 23, 24, 25, 26, 27 or more contiguous nucleic acids on 3' end of the miR-21, miR-34b, miR-182, miR-221, miR-222 or miR-802 target capture probe target hybridizing region. In some aspects, the promoter based oligomer comprises a target hybridizing sequence that is substantially complementary to about 12 or more contiguous nucleic acids on 3' end of the miR-221 target capture probe target hybridizing region. In some aspects, the promoter based oligomer comprises a target hybridizing sequence that is substantially complementary to about 5, 6, 7, 8, 9, 10, 11, 12, 13, 14, 15, 16, 17, 18, 19, 20, 21, 22, 23, 24, 25, 26, 27 or more contiguous nucleic acids on 3' end of the target capture probe target hybridizing region and the first amplification oligomer has a nucleotide sequence that is at least 95% identical to SEQ ID NO:49. In some aspects, the promoter based oligomer comprises a target hybridizing sequence that is substantially complementary to about 5, 6, 7, 8, 9, 10, 11, 12, 13, 14, 15, 16, 17, 18, 19, 20, 21, 22, 23, 24, 25, 26, 27 or more contiguous nucleic acids on 3' end of the miR-21, miR-34b, miR-182, miR-221, miR-222 or miR-802 target capture probe target hybridizing region and the first amplification oligomer has a nucleotide sequence that is at least 95% identical to SEQ ID NO:49. In some aspects, the promoter based oligomer comprises a target hybridizing sequence that is substantially complementary to about 12 or more contiguous nucleic acids on 3' end of the miR-221 target capture probe target hybridizing region and the first amplification oligomer has a nucleotide sequence that is at least 95% identical to SEQ ID NO:49. In some aspects, the promoter based oligomer comprises a target hybridizing sequence that is substantially complementary all or a portion of the nucleic acids on 3' end of the target capture probe target hybridizing region and the target capture oligomer is SEQ ID NO:24. In some aspects, the promoter based oligomer comprises a target hybridizing sequence that is substantially complementary to about 5, 6, 7, 8, 9, 10, 11, 12, 13, 14, 15, 16, 17, 18, 19, 20, 21, 22, 23, 24, 25, 26, 27 or more contiguous nucleic acids on 3' end of the target capture probe target hybridizing region and the target capture oligomer is SEQ ID NO:24. In some aspects, the promoter based oligomer comprises a target hybridizing sequence that is substantially complementary to about 12 or more contiguous nucleic acids on 3' end of the a target capture oligomer that is SEQ ID NO:24. In some aspects the promoter based amplification oligomer is SEQ ID NO:11. In some aspects, the reverse primer targets a portion of a nucleic acid amplification product that is complementary to the extension nucleic acid sequence of the first amplification oligomer.

In some aspects of the method, the amplification reaction comprises a first amplification oligomer configured to specifically hybridize a target nucleic acid, and a reverse primer targets a complement of the extension nucleic acid sequence of the first amplification oligomer. In some aspects, the amplification reaction comprises a first amplification oligomer configured to specifically hybridize a target nucleic acid, and a universal reverse primer targets a complement of the extension nucleic acid sequence of the first amplification oligomer. In some aspects, the amplification reaction comprises a first amplification oligomer configured to specifically hybridize a target nucleic acid and which comprises an extension nucleic acid sequence that is substantially identical to SEQ ID NO:49, and a reverse primer targets a complement of the extension nucleic acid sequence of the first amplification oligomer. In some aspects, the amplification reaction comprises a first amplification oligomer configured to specifically hybridize a target nucleic acid and which comprise an extension nucleic acid sequence that is substantially identical to SEQ ID NO:49, and the reverse primer is SEQ ID NO:20. In some aspects, the amplification reaction comprises a first amplification oligomer configured to specifically hybridize miR-221, and a universal reverse primer targets a complement of the extension nucleic acid sequence of the first amplification oligomer. In some aspects, the amplification reaction comprises a first amplification oligomer configured to specifically hybridize miR-221 and which comprises an extension nucleic acid sequence that is substantially identical to SEQ ID NO:49, and a reverse primer targets a complement of the extension nucleic acid sequence of the first amplification oligomer. In some aspects, the amplification reaction comprises a first amplification oligomer configured to specifically hybridize miR-221 and which comprise an extension nucleic acid sequence that is substantially identical to SEQ ID NO:49, and the reverse primer is SEQ ID NO:20. In some aspects, the amplification reaction comprises a first amplification oligomer configured to specifically hybridize miR-182, and a universal reverse primer targets a complement of the extension nucleic acid sequence of the first amplification oligomer. In some aspects, the amplification reaction comprises a first amplification oligomer configured to specifically hybridize miR-182 and which comprises an extension nucleic acid sequence that is substantially identical to SEQ ID NO:49, and a reverse primer targets a complement of the extension nucleic acid sequence of the first amplification oligomer. In some aspects, the amplification reaction comprises a first amplification oligomer configured to specifically hybridize miR-182 and which comprise an extension nucleic acid sequence that is substantially identical to SEQ ID NO:49, and the reverse primer is SEQ ID NO:20. In some aspects, the amplification reaction is a multiplex amplification comprising at least two first amplification oligomers, each configured to specifically hybridize a different target nucleic acid. In some aspects, the amplification reaction is a multiplex amplification comprising at least two first amplification oligomers, each configured to specifically hybridize a different target nucleic acid, and a reverse primer targets a complement of the extension nucleic acid sequence of each first amplification oligomer. In some aspects, the amplification reaction is a multiplex amplification comprising at least two first amplification oligomers, each configured to specifically hybridize a different target nucleic acid, and a universal reverse primer targets a complement of the extension nucleic acid sequence of each first amplification oligomer. In some aspects, the amplification reaction is a multiplex amplification comprising at least two first amplification oligomers, each configured to specifically hybridize a different target nucleic acid and comprise an extension nucleic acid sequence that is substantially identical to SEQ ID NO:49, and a reverse primer targets a complement of the extension nucleic acid sequence of each first amplification oligomer. In some aspects, the amplification reaction is a multiplex amplification comprising at least two first amplification oligomers, each configured to specifically hybridize a different target nucleic acid and comprise an extension nucleic acid sequence that is substantially identical to SEQ ID NO:49, and the reverse primer is SEQ ID NO:20. In some aspects, the amplification reaction is a multiplex amplification comprising at least two first amplification oligomers, one of which is configured to specifically hybridize miR-221, wherein the reverse primer targets a complement of the extension nucleic acid sequence of a first amplification oligomer or the reverse primer is a universal reverse primer that targets a complement of the extension nucleic acid sequence of each first amplification oligomer. The extension nucleic acid sequence can be substantially identical to SEQ ID NO:49. The reverse primer can be substantially identical to SEQ ID NO:20. In some aspects, the amplification reaction is a multiplex amplification comprising at least two first amplification oligomers, one of which is configured to specifically hybridize miR-182, wherein the reverse primer targets a complement of the extension nucleic acid sequence of a first amplification oligomer or the reverse primer is a universal reverse primer that targets a complement of the extension nucleic acid sequence of each first amplification oligomer. The extension nucleic acid sequence can be substantially identical to SEQ ID NO:49. The reverse primer can be substantially identical to SEQ ID NO:20. In some aspects, the amplification reaction is a multiplex amplification comprising at least two first amplification oligomers, one of which is configured to specifically hybridize miR-221 and one of which is configured to hybridize to miR-182, wherein a reverse primer targets a complement of the extension nucleic acid sequence of one of the first amplification oligomer and another reverse primer targets a complement of the extension nucleic acid sequence of the other first amplification oligomer, or wherein the reverse primer is a universal reverse primer that targets a complement of the extension nucleic acid sequence of each first amplification oligomer. The extension nucleic acid sequence can be substantially identical to SEQ ID NO:49. The reverse primer can be substantially identical to SEQ ID NO:20.

In some aspects of the methods, an amplification reaction comprises a first amplification oligomer that is an extender primer comprising a 3' target hybridizing sequence and a 5' extension nucleic acid sequence, wherein the 3' target hybridizing sequence is substantially complementary to about 9 or more contiguous nucleic acids at the 3' end of the miR-221 target nucleic acid, and further comprises providing a promoter based amplification oligomer comprising a 3' target hybridizing sequence and a 5' promoter sequence, wherein the target hybridizing sequence is substantially identical to 17 or more contiguous nucleic acids on 5' end of the miR-221 target nucleic acid. In some aspects, an amplification reaction comprises a first amplification oligomer for specifically hybridizing to a miR-221 target nucleic acid that is an extender primer comprising a 3' target hybridizing sequence and a 5' extension nucleic acid sequence, wherein the 3' target hybridizing sequence is substantially complementary to about 9 or more contiguous nucleic acids at the 3' end of the miR-221 target nucleic acid, and a first amplification oligomer for specifically hybridizing to a miR-182 target nucleic acid that is an extender primer comprising a 3' target hybridizing sequence and a 5' extension nucleic acid sequence, wherein the 3' target hybridizing sequence is substantially complementary to about 9 or more contiguous nucleic acids at the 3' end of the miR-182 target nucleic acid, and further comprises providing a promoter based amplification oligomer for hybridizing to a cDNA strand of a miR-221 target nucleic acid, the promoter based amplification oligomer comprising a 3' target hybridizing sequence and a 5' promoter sequence, wherein the target hybridizing sequence is substantially identical to 12 or more contiguous nucleic acids on 5' end of the miR-221 target nucleic acid, and a promoter based amplification oligomer for hybridizing to a cDNA strand of a miR-182 target nucleic acid, the promoter based amplification oligomer comprising a 3' target hybridizing sequence and a 5' promoter sequence, wherein the target hybridizing sequence is substantially identical to 12 or more contiguous nucleic acids on 5' end of the miR-182 target nucleic acid. In some aspects the amplification reaction comprises one or more target capture probes. In some aspects, the amplification reaction comprises a target capture probe configured to capture a miR-221 target nucleic acid. In some aspects the amplification reaction comprises one or more target capture probes. In some aspects, the amplification reaction comprises a target capture probe configured to capture a miR-221 target nucleic acid comprising a target hybridizing sequence that is substantially complementary to SEQ ID NO:44. In some aspects, the amplification reaction comprises a target capture probe that is substantially identical to SEQ ID NO:24. In some aspects, the amplification reaction comprises a target capture probe configured to capture a miR-182 target nucleic acid. In some aspects the amplification reaction comprises one or more target capture probes. In some aspects, the amplification reaction comprises a target capture probe configured to capture a miR-182 target nucleic acid comprising a target hybridizing sequence that is substantially complementary to SEQ ID NO:41. In some aspects, the amplification reaction comprises a target capture probe that is substantially identical to SEQ ID NO:23. In some aspects, the amplification reaction is performed in the presence of target capture probe and wherein the amplification reaction conditions are configured to maintain the target capture probe in a hairpin formation. In some aspects, the amplification reaction is an isothermal amplification reaction.

In some aspects of the methods, amplification products are detected using a detection probe oligomer. In some aspects of the methods, amplification products are detected using a detection probe oligomer that target a portion of an amplification product corresponding to the target nucleic acid. In some aspects of the methods, amplification products are detected using a detection probe oligomer that target a portion of an amplification product corresponding to the extension nucleic acid sequence. In some aspects, the detection probe oligomer is a linear detection probe. In some aspects, the detection probe oligomer is a hairpin detection probe. In some aspects, the detection probe oligomer is labeled. In some aspects, the detection probe oligomer is dual labeled. In some aspects, the detection of the target nucleic acid is a real-time detection. In some aspects, the detection probe oligomer is a linear detection probe. In some aspects, the detection probe oligomer is a hairpin detection probe. In some aspects, the detection probe oligomer is labeled. In some aspects, the detection probe oligomer is dual labeled. In some aspects, the detection of the target nucleic acid is a real-time detection.

In some aspects, the method are useful for diagnosing cancer, providing a prognosis relating to a cancer, monitoring the effectiveness of a cancer treatment, or a combination thereof. In some aspects, the cancer is prostrate cancer.

One embodiment is a composition comprising any one or more of the oligomers described herein. Some aspects provide a target capture probe that forms under hybridizing conditions at least a partially double-stranded structure that is a hairpin structure made up of a contiguous linear sequence that includes an internal target hybridizing sequence that is substantially complementary to all or a portion of SEQ ID NOS: 44, 41, 47, 38, 29 or 34 and that forms a single-stranded loop portion of the hairpin structure, wherein the internal target hybridizing sequence is flanked by a capture region and by a terminal region that binds to the capture region to form a double-stranded stem portion of the hairpin structure and wherein the capture region further comprises a substantially homopolymeric nucleic acid sequence and the terminal region further comprises a substantially homopolymeric nucleic acid sequence that is complementary to the capture region sequence. In some aspects, the capture region sequence is selected from the group consisting of dT.sub.0-3 A.sub.10-30. In some aspects, the capture probe is at least 95% identical to SEQ ID NOS:22, 23, 24, 25 or 26.

One embodiment provides an amplification reaction mixture comprising any one or more of the oligomers described herein. In one aspect, the amplification reaction mix comprises any one or more of, the target capture oligomers described herein. In one aspect, the amplification reaction mix comprises any one or more of the first amplification oligomers described herein. In one aspect, the amplification reaction mix comprises any one or more of the promoter-based amplification oligomers described herein. In one aspect, the amplification reaction mix comprises any one or more of the reverse primer oligomers described herein. In one aspect, the amplification reaction mix comprises any one or more of the detection probe oligomers described herein. In one aspect, the amplification reaction mix comprises any one or more of the target capture oligomers described herein, first amplification oligomers described herein, promoter based oligomers described herein, reverse primer oligomers described herein and detection probe oligomers described herein. In one aspect there is provided an amplification reaction mixture comprising a small RNA, miR21, miR-34b, miR-182, miR-221, miR-222 or miR-802 target capture probe that forms under hybridizing conditions at least a partially double-stranded structure that is a hairpin structure made up of a contiguous linear sequence that includes an internal target hybridizing sequence that is substantially complementary to all or a portion of small RNA, miR21, miR-34b, miR-182, miR-221, miR-222 or miR-802 and that forms a single-stranded loop portion of the hairpin structure, wherein the internal target hybridizing sequence is flanked by a capture region and by a terminal region that binds to the capture region to form a double-stranded stem portion of the hairpin structure and wherein the capture region further comprises a substantially homopolymeric nucleic acid sequence and the terminal region further comprises a substantially homopolymeric nucleic acid sequence that is complementary to the capture region sequence; and a first amplification oligomer configured to hybridize to a small RNA, miR21, miR-34b, miR-182, miR-221, miR-222 or miR-802 target nucleic acid that is an extender primer comprising a 3' target hybridizing sequence and a 5' extension nucleic acid sequence, wherein the 3' target hybridizing sequence is substantially identical to about 9 or more contiguous nucleic acids at the 5' end of the target hybridizing sequence of the target capture probe. In one aspect there is provided an amplification reaction mixture comprising a miR21, miR-34b, miR-182, miR-221, miR-222 or miR-802 target capture probe that forms under hybridizing conditions at least a partially double-stranded structure that is a hairpin structure made up of a contiguous linear sequence that includes an internal target hybridizing sequence that is substantially complementary to all or a portion of SEQ ID NOS:38, 29, 41, 44, 47 or 34 and that forms a single-stranded loop portion of the hairpin structure, wherein the internal target hybridizing sequence is flanked by a capture region and by a terminal region that binds to the capture region to form a double-stranded stem portion of the hairpin structure and wherein the capture region further comprises a substantially homopolymeric nucleic acid sequence and the terminal region further comprises a substantially homopolymeric nucleic acid sequence that is complementary to the capture region sequence; and a first amplification oligomer configured to hybridize to a small RNA, miR21, miR-34b, miR-182, miR-221, miR-222 or miR-802 target nucleic acid that is an extender primer comprising a 3' target hybridizing sequence and a 5' extension nucleic acid sequence, wherein the 3' target hybridizing sequence is substantially identical to about 9 or more contiguous nucleic acids at the 5' end of the target hybridizing sequence of the target capture probe. In one aspect there is provided an amplification reaction mixture comprising a miR-221 target capture probe that forms under hybridizing conditions at least a partially double-stranded structure that is a hairpin structure made up of a contiguous linear sequence that includes an internal target hybridizing sequence that is substantially complementary to all or a portion of SEQ ID NO:44 and that forms a single-stranded loop portion of the hairpin structure, wherein the internal target hybridizing sequence is flanked by a capture region and by a terminal region that binds to the capture region to form a double-stranded stem portion of the hairpin structure and wherein the capture region further comprises a substantially homopolymeric nucleic acid sequence and the terminal region further comprises a substantially homopolymeric nucleic acid sequence that is complementary to the capture region sequence; and a first amplification oligomer configured to hybridize to a miR-221 target nucleic acid that is an extender primer comprising a 3' target hybridizing sequence and a 5' extension nucleic acid sequence, wherein the 3' target hybridizing sequence is substantially identical to about 9 or more contiguous nucleic acids at the 5' end of the target hybridizing sequence of the miR-221 target capture probe. In one aspect there is provided an amplification reaction mixture for multiplex amplifications comprising (a) a miR-221 target capture probe that forms under hybridizing conditions at least a partially double-stranded structure that is a hairpin structure made up of a contiguous linear sequence that includes an internal target hybridizing sequence that is substantially complementary to all or a portion of SEQ ID NO:44 and that forms a single-stranded loop portion of the hairpin structure, wherein the internal target hybridizing sequence is flanked by a capture region and by a terminal region that binds to the capture region to form a double-stranded stem portion of the hairpin structure and wherein the capture region further comprises a substantially homopolymeric nucleic acid sequence and the terminal region further comprises a substantially homopolymeric nucleic acid sequence that is complementary to the capture region sequence and further comprising a miR-182 target capture probe that forms under hybridizing conditions at least a partially double-stranded structure that is a hairpin structure made up of a contiguous linear sequence that includes an internal target hybridizing sequence that is substantially complementary to all or a portion of SEQ ID NO:41 and that forms a single-stranded loop portion of the hairpin structure, wherein the internal target hybridizing sequence is flanked by a capture region and by a terminal region that binds to the capture region to form a double-stranded stem portion of the hairpin structure and wherein the capture region further comprises a substantially homopolymeric nucleic acid sequence and the terminal region further comprises a substantially homopolymeric nucleic acid sequence that is complementary to the capture region sequence; and (b) a first amplification oligomer configured to hybridize to a miR-221 target nucleic acid that is an extender primer comprising a 3' target hybridizing sequence and a 5' extension nucleic acid sequence, wherein the 3' target hybridizing sequence is substantially identical to about 9 or more contiguous nucleic acids at the 5' end of the target hybridizing sequence of the miR-221 target capture probe, and further comprising a first amplification oligomer configured to hybridize to a miR-182 target nucleic acid that is an extender primer comprising a 3' target hybridizing sequence and a 5' extension nucleic acid sequence, wherein the 3' target hybridizing sequence is substantially identical to about 9 or more contiguous nucleic acids at the 5' end of the target hybridizing sequence of the miR-182 target capture probe. In one aspect there is provided an amplification reaction mixture for multiplex amplifications comprising (a) two or more target capture probes configured to specifically hybridize to two or more of a small RNA, miR21, miR-34b, miR-182, miR-221, miR-222 or miR-802 target nucleic acid, wherein the target capture oligomers form under hybridizing conditions at least a partially double-stranded structure that is a hairpin structure made up of a contiguous linear sequence that includes an internal target hybridizing sequence that is substantially complementary to all or a portion of each of their target nucleic acids and that form a single-stranded loop portion of the hairpin structure, wherein the internal target hybridizing sequences are flanked by capture regions and by terminal regions that binds to the capture regions to form double-stranded stem portion of the hairpin structure and wherein the capture regions further comprises a substantially homopolymeric nucleic acid sequence and the terminal regions further comprise substantially homopolymeric nucleic acid sequence that is complementary to the capture region sequences; and (b) two or more first amplification oligomers configured to hybridize two or more of a small RNA, miR21, miR-34b, miR-182, miR-221, miR-222 or miR-802 target nucleic acids, wherein the first amplification oligomers are extender primers comprising 3' target hybridizing sequences and 5' extension nucleic acid sequences, wherein the 3' target hybridizing sequences are substantially identical to about 9 or more contiguous nucleic acids at the 5' end of the target hybridizing sequence of the corresponding target capture probes.

In some aspects the amplification reaction mixture further comprises a promoter based oligomer that comprises a target hybridizing sequence that is substantially complementary to 12 or more contiguous nucleic acids on 3' end of the miR-221 target capture probe. In some aspects, the promoter-based oligomer is at least 95% identical to SEQ ID NO:11. In some aspects, the promoter-based oligomer is SEQ ID NO:11. In some aspects the amplification reaction mixture further comprises a promoter based oligomer that comprises a target hybridizing sequence that is substantially complementary to 12 or more contiguous nucleic acids on 3' end of the miR-182 target capture probe. In some aspects, the promoter-based oligomer is at least 95% identical to SEQ ID NO:10. In some aspects, the promoter-based oligomer is SEQ ID NO:10. In some aspects, the miR-221 target capture probe is at least 95% identical to SEQ ID NO:24. In some aspects, the miR-221 target capture probe is SEQ ID NO:24. In some aspects, the miR-182 target capture probe is at least 95% identical to SEQ ID NO:23. In some aspects the miR-182 target capture probe is SEQ ID NO:23. In some aspects, the miR-221 extender primer is at least 95% identical to SEQ ID NO:17. In some aspects, the miR-221 extender primer is SEQ ID NO:17. In some aspects the miR-182 extender primer is at least 95% identical to SEQ ID NO:16. In some aspects the miR-182 extender primer is SEQ ID NO:16. In some aspects, the amplification reaction mixture further comprises a reverse primer. In some aspects, the reverse primer targets a portion of a sequence that is complementary to the extension nucleic acid sequence of an extender primer. In some aspects, the reverse primer is SEQ ID NO:20. in some aspects, the target capture probe comprises at least one 2'-OMe residue in the target hybridizing sequence.

BRIEF DESCRIPTION OF THE FIGURES

FIG. 2 illustrates an embodiment showing capture and detection of a target nucleic acid that mixes the target nucleic acid (shown as the sequence a b c d e) with a completely or partially double-stranded capture probe that contains complementary sequences on the two strands (shown as poly-A and poly-T sequences) and one target-complementary region (shown as the sequence a' b' c' on the poly-T containing strand and also referred to as a target hybridizing sequence), to form a capture hybrid made up of the target nucleic acid hybridized to the target hybridizing region of the capture probe strand, and another portion of the capture probe strand (poly-T) hybridized to a complementary immobilized probe (shown as poly-A attached to a capture support), followed by releasing the target nucleic acid into solution to form a detection hybrid made up of a detection probe (shown by the sequence a' b' c' d' e') hybridized to the target nucleic acid to produce a detectable signal (shown by a star-shaped character) to indicate the presence of the target. An amplification step is not shown in this Figure. Detection can be performed directly on isolated target nucleic acids or an amplification step can be included and detection performed in real-time or endpoint.

FIGS. 6a-b shows the specificity of the miR TMA assay. A) Template-dependent amplification of prostate cancer candidate miRNAs. Amplification reactions were run in triplicate (without target capture). The slope and R.sup.2 values were determined from log copy points 1.7 to 7.7 (5 to $5 \times 10^7$ copies per reaction). B) Specificity test of the miR-221 assay for miR-221 target nucleic acid as compared to miR-222, miR-30b, and miR-802 related and unrelated non-target nucleic acids.

DETAILED DESCRIPTION

Figure 1:
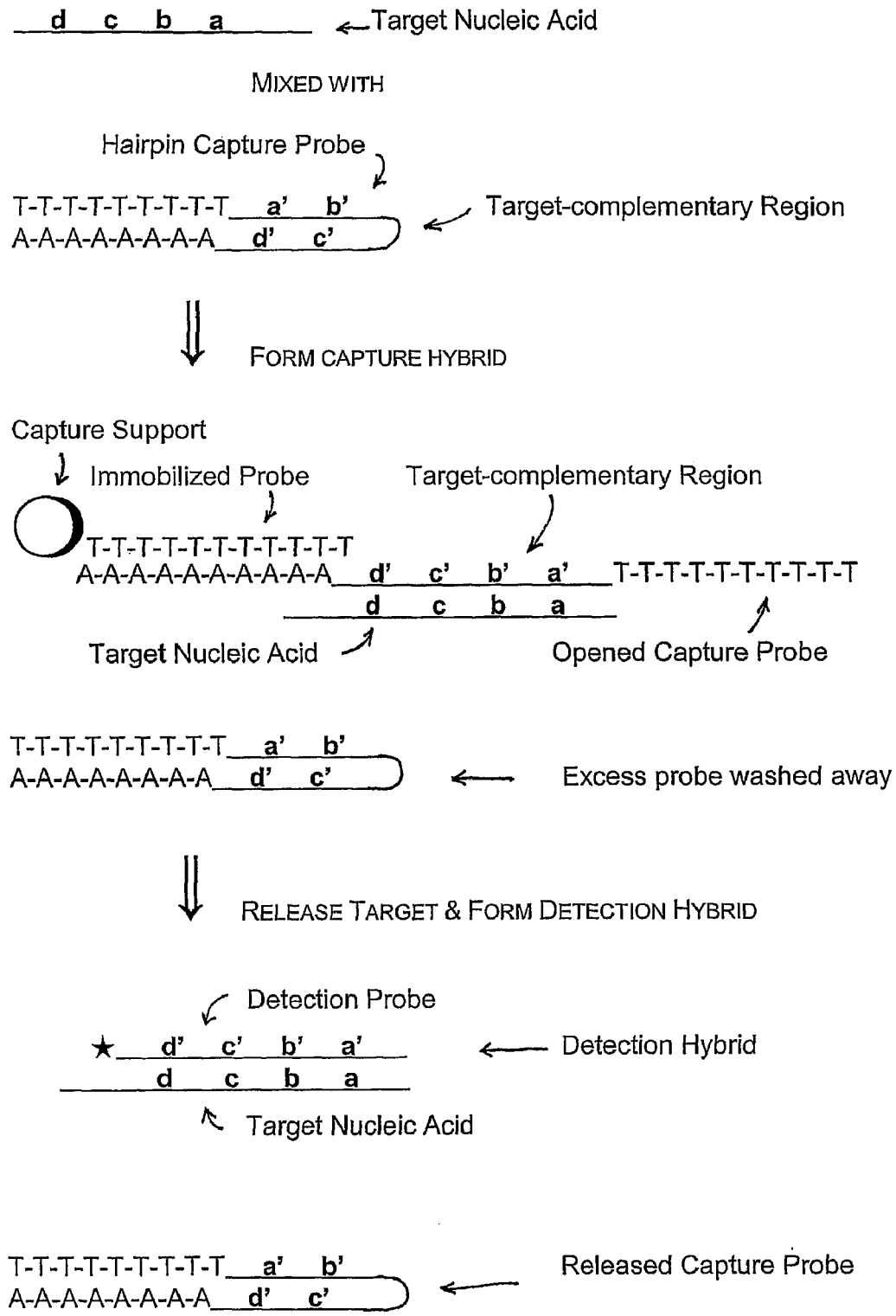
FIG. 1 illustrates an embodiment showing capture and detection of a target nucleic acid by mixing target nucleic acid (shown as the sequence d c b a) with a hairpin capture probe which has complementary sequences at its 5' and 3' ends (shown as poly-T and poly-A regions) flanking a target complementary region (shown as the sequence a' b' c' d' and also referred to as a target hybridizing sequence) to form a capture hybrid made up of the target nucleic acid hybridized to target hybridizing region of the opened capture probe, and a portion of a capture probe (poly-A region) hybridized to a complementary immobilized probe (shown as poly-T attached to a capture support), followed by releasing the target into solution where it forms a detection hybrid made up of a detection probe (shown by the sequence d' c' b' a') hybridized to the target nucleic acid to produce a detectable signal (shown by a star-shaped character) to indicate the presence of the target. An amplification step is not shown in this Figure. Detection can be performed directly on isolated target nucleic acids or an amplification step can be included and detection performed in real-time or endpoint.
Figure 3:
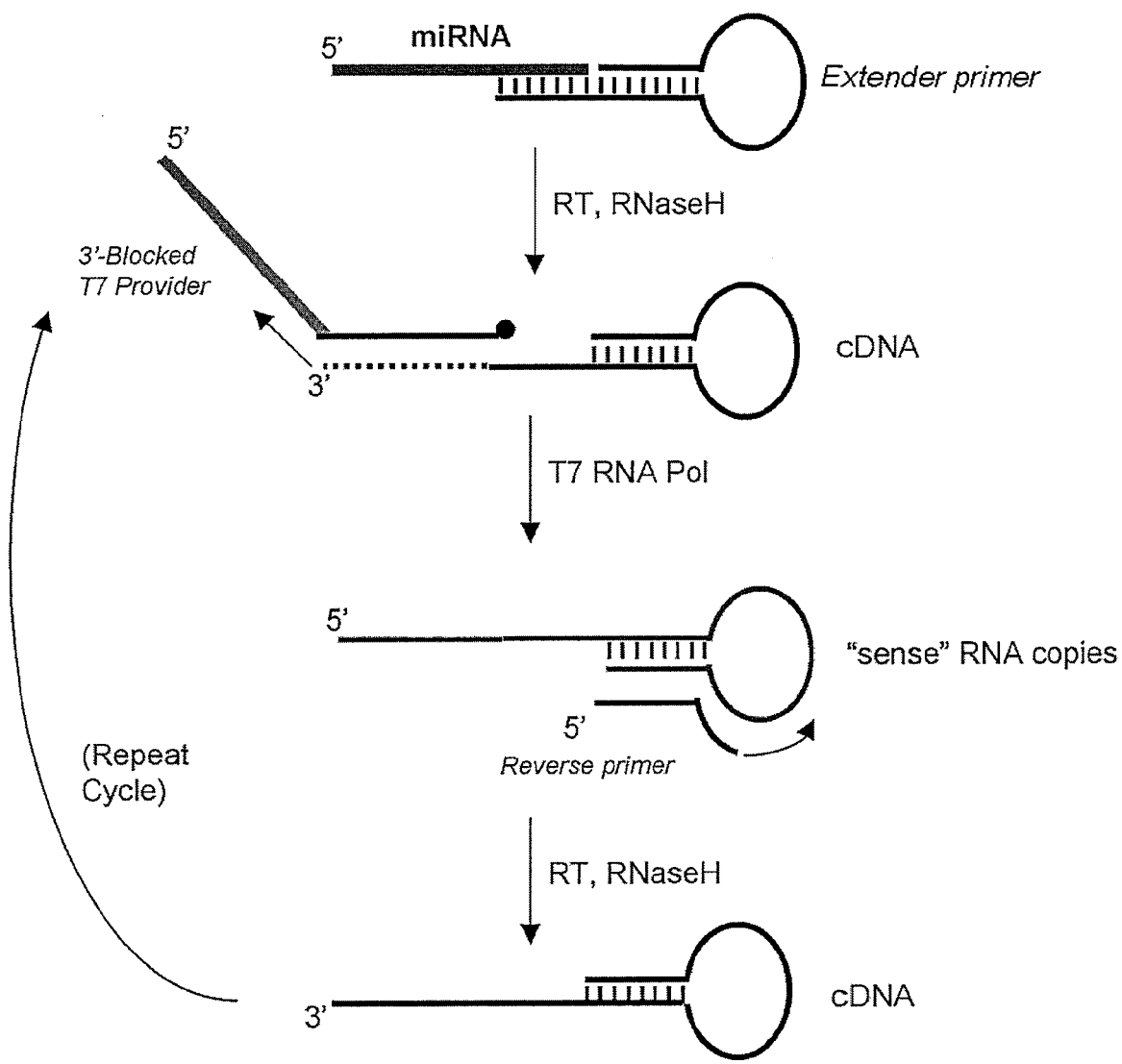
FIG. 3 illustrates a general schematic of miRNA TMA amplification reaction using an extender primer oligomer, a promoter based oligomer and a reverse primer oligomer.

This invention is useful for detecting a target nucleic acid of interest present in a sample. The small RNA target nucleic acid is preferably a micro RNA, miR-21, miR-34b, miR-182, miR-221, miR-222 or miR-802. The methods use relatively few and easily performed steps to isolate and/or concentrate the target nucleic acid from other sample components and to detect the target nucleic acid. Samples are typically one or more cells obtained as a specimen that can be used to determine the presence or abundance of a target nucleic acid that is a biomarker for a disorder. For example, the sample can be one or more blood cells that can be used for determining a disorder wherein a biomarker is present in blood cells. Another example, the sample can be one or more biopsied cells that can be used for determining the presence of a disorder wherein a biomarker is present in the tissue or organ from which the biopsy was taken. The methods include isolating the target nucleic acid from the sample. In some instances the target nucleic acid is released from a cell by lysing the cell in which the target nucleic acid is suspected of being present. In some instances, the released target nucleic acid is then isolated away from other components of the sample, which may include cellular debris is the target nucleic acid was released by cell lysis. Isolation can include general nucleic acid isolation, which can be done using kits like the mirVana kits (ABI, Foster City, Calif.); Trizol LS (Invitrogen, Carlsbad, Calif.); Micro RNA Isolation kits (Stratagene, La Jolla, Calif.) and High-Pure miRNA Isolation kits (Roche, Indianapolis, Ind.). Preferably, isolation of the target nucleic acid(s) include a capture step in which a target nucleic acid is captured by using one or more target capture probes to form a capture hybrid that is linked to a capture support. The capture hybrid is then separated from other sample components including non-target nucleic acids. Captured target nucleic acids are then released from the capture support and assayed by one or more downstream methodologies, such as an amplification reaction and/or a detection reaction. The target nucleic acids can be captured directly from sample cell lysates or can be captured from isolated nucleic acids, such as a total RNA isolation or a fractionated population of RNA such as a population of small RNA.

Removal of non-target nucleic acids is beneficial in that non-target nucleic acids potentially negatively impact the detection of small RNA through non-specifically hybridizing to assay system oligomers, crowding the reaction to make scarce target nucleic acid species undetectable or unreliably detectable and otherwise interfering with the assay. When a detection reaction is performed in the presence of a generalized population of nucleic acids, e.g., total RNA or size fractionated RNA, the non-target sequences in the reaction can non-specifically hybridize with the assay oligonucleotides, thereby removing needed reagents from the assay. A non-specifically hybridized reagent is not available for its intended target, and furthermore, may be used by the non-specific target for generating false positive signals. The target capture step can be performed in place of a general nucleic acid isolation procedure, or can be performed on the nucleic acid recovered from such a general isolation. Preferably, in a downstream assay the target nucleic acid is detected. Preferably, the detection step is a nucleic acid probe based detection step. The detection step is sometime preceded by an amplification step; though this is not a requirement.

Target nucleic acids are typically from about 17-27 nucleotides in length. When a target nucleic acid is captured and then detected, the target capture oligomer and the detection probe oligomer comprise target hybridizing sequences that are substantially similar to one another. Thus, these two oligomers have target hybridizing sequences that compete for the target nucleic acid. In one embodiment, the target capture oligomer is configured so that under a first set of conditions the target capture oligomer is not in a hairpin form, and thus the target hybridizing sequence is available to hybridize to a target nucleic acid. However, under a second set of conditions, the target capture oligomer is in a hairpin form. The detection probe, on the other hand, is configured to hybridize to the target nucleic acid under this second set of conditions. The target capture probe is therefore configured to be unavailable to hybridize the small target nucleic acid under the conditions wherein the detection probe is present for hybridizing the target. In a method, one or more target nucleic acids are captured from a sample or from a general nucleic acid isolate under a first set of conditions and isolated away from the remaining debris and/or non-target nucleic acids. The one or more target nucleic acids along with their respective target capture oligomers are released into solution and combined with one or more detection probe oligomers specific for each of the target nucleic acids. The solution at this point contains target nucleic acid(s), target capture oligomer(s) and detection probe oligomer(s), wherein the target hybridizing sequences of a target capture oligomer and a detection probe oligomer configured to hybridize a target nucleic acid are substantially identical. A set of conditions is then applied to the solution so that the detection probe oligomer preferentially hybridizes to the target nucleic acid, not the target capture oligomer. When a target nucleic acid is captured, amplified and then detected, the target capture oligomer and the amplification oligomers comprise target hybridizing sequences that are substantially similar or substantially identical to one another. Thus, these oligomers have target hybridizing sequences that compete for the target nucleic acid or that can hybridize together. In one embodiment, the target capture oligomer is configured so that under a first set of conditions the target capture oligomer is not in a hairpin form, and thus the target hybridizing sequence is available to hybridize to a target nucleic acid. However, under a second set of conditions, the target capture oligomer is in a hairpin form. The amplification oligomers, on the other hand, are configured to hybridize to the target nucleic acid, or complement thereof under this second set of conditions. The target capture probe is therefore configured to be unavailable to hybridize the small target nucleic acid under the conditions wherein the amplification oligomers are present for hybridizing the target or its complement. In a method, one or more target nucleic acids are captured from a sample or from a general nucleic acid isolate under a first set of conditions and isolated away from the remaining debris and/or non-target nucleic acids. The one or more target nucleic acids along with their respective target capture oligomers are released into solution and combined with amplification oligomers specific for each of the target nucleic acids. The solution at this point contains target nucleic acid(s), target capture oligomer(s) and amplification oligomers(s), wherein the target hybridizing sequences of a target capture oligomer and a first amplification oligomer are configured to hybridize all or a portion of the same target sequence on a target nucleic acid, and wherein all or a portion of the second amplification oligomer target hybridizing sequence is substantially identical to all or a portion of the target capture oligomer target hybridizing sequence. A set of conditions is then applied to the solution so that the amplification oligomers preferentially hybridize to the target nucleic acid, not the target capture oligomer, and amplification products are generated.

These methods are useful for detecting the presence or absence of one or more target nucleic acids in a sample. These methods are useful for detecting the abundance (including expression level) of one or more target nucleic acids in a sample. These methods are useful particularly for detecting small target nucleic acids that may be present at dilute concentrations in a sample, e.g., a small nucleic acids excreted in urine or present in a cellular or tissue extract. These methods are also useful for assaying many samples, preferably simultaneously or in rapid succession, such as in an automated high through-put system because the capture and detection steps can be performed in a single reaction chamber per sample. In addition to directly detecting one or more target nucleic acids present in a sample, the methods herein further include a nucleic acid amplification wherein the target nucleic acid(s) are amplified and the amplification product(s) are detected. Preferably the target nucleic acids are isolated away from cellular debris and/or non-target nucleic acids. Isolated target nucleic acids are more accurately amplified and detected because interference by a non-target nucleic acid is reduced. Capture and amplification of one or more target nucleic acids uses a target capture oligomer and at least a first amplification oligomer. The target capture oligomer and the first amplification oligomer, therefore, are competing for hybridization to a small target sequence. Additional amplification oligomers include a promoter based amplification oligomer, a reverse primer oligomer or both. The target capture oligomer and the promoter-based oligomer can hybridize together. Thus, it is preferably that the target capture oligomer is subjected to chemical and/or physical conditions that are configured to make the target capture oligomer unavailable to interfere with the amplification reaction. Preferably, the unavailable target capture oligomer is in a double stranded or partially double stranded structure. Preferably, the unavailable target capture oligomer is a hairpin structure.

Amplification methods include PCR (RT or qRT), transcription mediated amplification, or other amplification methods. Preferably, the amplification method is a transcription mediated amplification method and the amplification oligomers include a first primer oligomer configured to hybridize to at least a portion of a target nucleic acid and to further add an extension nucleic acid sequence to the target nucleic acid, a promoter based amplification oligomer configured to hybridize to a cDNA strand section complementary to the target nucleic acid and a reverse primer oligomer configured to hybridize to a portion of the extension sequence. In a multiplex reaction for detecting two or more target nucleic acids, the first primer oligomer preferably adds the same extension nucleic acid sequence to each target nucleic acid, in which case the reverse primer oligomer is a universal primer oligomer. Preferably, the methods for detecting the presence or abundance of a target nucleic acid include an amplification reaction that takes place in the presence of a target capture oligomer. Preferably the amplification reaction is configured to amplify one or more target nucleic acids in the presence of one or more target capture oligomers without interference from the target capture oligomer. Preferably the one or more target capture oligomers are configured to form a hairpin structure under conditions wherein the target nucleic acid is released and to remain in a hairpin configuration during an amplification reaction. Preferably the one or more target capture oligomers are configured to form a hairpin structure under conditions wherein the target nucleic acid is released and to remain in a hairpin configuration during transcription mediated amplification reaction.

The presence and amount of one or more target nucleic acids in a sample are accurately determined using the oligomers and methods of this current disclosure. Target nucleic acids can be biomarkers for determining a disease state, determining a prognosis, developing a drug compound or monitoring the efficacy of a treatment. The presence of or the relative abundance of biomarkers is useful in such efforts. However, the value of information received from a biomarker detection assay diminishes if the results are negatively impacted by contaminations, including non-target nucleic acids. Some problems with non-target nucleic acids include non-specific hybridization of the oligomer reagents to the non-target nucleic acids, thereby depleting reagents and/or providing non-target amplification products as false positive signals. Additionally, the presence of cellular debris and non-target nucleic acids can bury small and less abundant target nucleic acids so that the oligomer reagents cannot hybridize with their targets, leading to false positives. Thus, it is preferred that the detection methods for determining the presence or abundance of a target nucleic acid include a step for isolating the target nucleic acids away from interfering contamination.

To better understand the various embodiments of the invention, some of the terms used in the description of the invention are more fully described below.

A "Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see PCT No. WO 95/32305), phosphorothioate linkages, methylphosphonate linkages, or combinations thereof. Sugar moieties of the nucleic acid may be either ribose or deoxyribose, or similar compounds having known substitutions, e.g., 2' methoxy substitutions and 2' halide substitutions (e.g., 2'-F). Nitrogenous bases may be conventional bases (A, G, C, T, U), analogs thereof (e.g., inosine, 5-methylisocytosine, isoguanine; The Biochemistry of the Nucleic Acids 5-36, Adams et al., ed., 11th ed., 1992, Abraham et al., 2007, BioTechniques 43: 617-24), which include derivatives of purine or pyrimidine bases (e.g., N4-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, O.sup.6-methylguanine, 4-thio-pyrimidines, 4-amino-pyrimidines, 4-dimethylhydrazine-pyrimidines, and O.sup.4-alkyl-pyrimidines, and pyrazolo-compounds, such as unsubstituted or 3-substituted pyrazolo[3,4-d]pyrimidine; U.S. Pat. Nos. 5,378,825, 6,949,367 and PCT No. WO 93/13121). Nucleic acids may include "abasic" residues in which the backbone does not include a nitrogenous base for one or more residues (U.S. Pat. No. 5,585,481). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., 2004, Biochemistry 43(42):13233-41). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well known in the art although nucleic acids may be purified from natural sources using routine techniques.

A nucleic acid "backbone" refers to groups or linkages known in the art (Eschenmoser, 1999, Science 284:2118-2124), such as, e.g., sugar-phosphodiester linkages, 2'-O-methyl linkages, guanidine linkers in DNA ("DNG"), S-methylthiourea linkers, methylphosphonate linkages, phosphoramidite linkages, amide backbone modifications as in polyamide or peptide nucleic acids (PNA), phosphorothioate linkages, phosphonic ester nucleic acid linkages, pyranosyl oligonucleotide linkages, bicyclo- and tricyclo-nucleic acid linkages, formacetal and 3'-thioformacetal linkages, morpholino linkages, or other modifications of the natural phosphodiester internucleoside bond, or combinations of such linkages in a single backbone (Majlessi et al., 1998, Nucl. Acids Res. 26(9):2224-2229; Dempcy et al., 1995, Proc. Natl. Acad. Sci. USA 92:6097-6101; Browne et al., 1995, Proc. Natl. Acad. Sci. USA 92:7051-7055; Arya & Bruice, 1998, J. Am. Chem. Soc. 120:6619-6620; Reynolds et al., 1996, Nucl. Acids Res. 24(22):4584-4591; Gryaznov & Chen, 1994, Am. Chem. Soc. 116:3143-3144; Chaturvedi et al., 1996, Nucl. Acids Res. 24(12):2318-2323; Hyrup & Nielsen, 1996, Bioorg. & Med. Chem. 4:5-23; Hydig-Hielsen et al., PCT App. No. WO 95/32305; Mesmaeker et al., Syn. Lett., November 1997:1287-1290; Peyman et al., 1996, Angew. Chem. Int. Ed. Engl. 35(22):2636-2638; Aerschot et al., 1995, Angew. Chem. Int. Ed. Engl. 34(12):1338-1339; Koshkin et al. 1998, J. Am. Chem. Soc. 120:13252-13253; Steffens & Leumann, 1997, J. Am. Chem. Soc. 119:11548-11549; Jones et al., 1993, J. Org. Chem. 58:2983-2991; Summerton & Weller, 1997, Antisense & Nucl. Acid Drug Dev. 7:187-195; Stirchak et al., 1989, Nucl. Acids Res. 17(15): 6129-6141). A nucleic acid backbone may include a mixture of linkages in the same nucleic acid (e.g., sugar-phosphodiester and phosphorothioate) or may have all of one type of linkages (e.g., all amide modification linkages in an oligomer).

The interchangeable terms "oligomer," "oligo" and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources, but or may be synthesized using any of a variety of well known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase, it may provide a promoter if it contains a sequence recognized by an RNA polymerase and allows for transcription (e.g., a promoter-based oligomer), and it may function to prevent hybridization or impede primer extension if appropriately situated and/or modified.

A "target" or "target sequence" or "target nucleic acid" refers to a sequence of nucleotide bases present in a nucleic acid, or portion of a nucleic acid, to which another sequence binds, e.g., by using standard complementary base pairing. Preferably, herein, a target nucleic acid is a small RNA having a length of from about 17 to about 27 contiguous nucleotides. Small RNA target nucleic acids include, miRNA, siRNA, shRNA, antisense RNA, snRNA or the like. Those skilled in the art will appreciate that a target nucleic acid may exist in different forms, i.e., single-stranded, double-stranded, triple-stranded, or mixtures thereof, such as in a partially double-stranded hairpin structure or partially double-stranded duplex structure, and will further appreciate that a target sequence may be present on any strand (+ or −) of the structure. It is well known in the art that a multi-stranded nucleic acid is readily converted to its single-strand components by using standard methods, such as by heating a nucleic acid above its melting temperature (Tm) and/or by using chemical denaturants.

By "complementary" or "complementarity of" nucleic acids is meant that a nucleotide sequence in one strand of nucleic acid, due to orientation of the functional groups, will hydrogen bond to another sequence on an opposing nucleic acid strand. The complementary bases typically are, in DNA, A with T and C with G, and, in RNA, C with G, and U with A. "Substantially complementary" means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations known to those skilled in the art to predict the Tm of hybridized strands, or by empirical determination of Tm by using routine methods. Tm refers to the temperature at which a population of hybridization complexes formed between two nucleic acid strands are 50% denatured. At a temperature below the Tm, formation of a hybridization complex is favored, whereas at a temperature above the Tin, melting or separation of the strands in the hybridization complex is favored. Tm may be estimated for a nucleic acid having a known G+C content in an aqueous 1 M NaCl solution by using, e.g., Tm=81.5+0.41(% G+C), although other Tm computations are known in the art which take into account nucleic acid structural characteristics. Nucleic acid sequences are identical when their contiguous nucleotide arrangements are the same. Identical sequences includes those that have a modified residue in one sequence, but not the other, so long as the residue is basically the same (e.g., a 2'-OMe residue in one sequence is still identical to a strand lacking the 2'OMe modification). Substantially identical sequences are those that contain sequence differences between the two strands, but the strands retain similar hybridization properties. Identity and substantial identity between sequences are understood and easily determined by ordinarily skilled artisans. Sequences herein that are at least a certain percent identical or complementary to another sequence, means that the sequences includes all rational numbers from the referenced percent identity to 100%. For example, at least 80% means all natural number percentages 80, 81, 82, 82, 84, 85, 86, 87, 88, 89, 90, 91, 92, 93, 94, 95, 96, 97, 98, 99 and 100, as well as any fraction in between (e.g., 82.6, 91.1, 97.9, etc). Ordinarily skilled artisans can determine percent complementarity and percent identity.

"Hybridization condition" refers to the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other well known factors, such as the length of incubation time or reaction chamber dimensions may contribute to the environment (e.g., Sambrook et al., Molecular Cloning, A Laboratory Manual, 2nd ed., pp. 1.90-1.91, 9.47-9.51, 11.47-11.57 (Cold Spring Harbor Laboratory Press, Cold Spring Harbor, N.Y., 1989)).

A "label" refers to a molecular moiety that is detectable or produces a detectable response or signal directly or indirectly, e.g., by catalyzing a reaction that produces a detectable signal. Labels include luminescent moieties (such as fluorescent, bioluminescent, or chemiluminescent compounds), radioisotopes, members of specific binding pairs (e.g., biotin and avidin), enzyme or enzyme substrate, reactive groups, or chromophores, such as a dye or particle that results in detectable color.

A "detection probe" is a oligomer or polymer that binds specifically to a target sequence and which binding results, directly or indirectly, in a detectable signal to indicate the presence of the target sequence. A detection probe need not be labeled to produce a detectable signal, e.g., an electrical impulse resulting from binding the probe to its target sequence may be the detectable signal. A "labeled probe" is a probe that contains or is linked, directly or indirectly, to a label. Methods of making and/or using labeled probes are well known in the art (e.g., Sambrook et al., Molecular Cloning, A Laboratory Manual, 2nd ed., Chapt. 10; U.S. Pat. No. 6,361,945, Becker et al.; U.S. Pat. No. 5,658,737, Nelson et al.; U.S. Pat. No. 5,656,207, Woodhead et al.; U.S. Pat. No. 5,547,842, Hogan et al.; U.S. Pat. No. 5,283,174, Arnold et al.; U.S. Pat. No. 4,581,333, Kourilsky et al.; U.S. Pat. No. 5,731,148, Becker et al.). For example, detection probes may include a non-nucleotide linker and a chemiluminescent label attached to the linker (U.S. Pat. Nos. 5,185,439, 5,585,481 and 5,639,604, Arnold et al.).

Examples of detection probes include linear or hairpin oligonucleotides of about 5 to 50 nucleotides in length having an attached label. Linear probes include taqman probes and AE probes. Hairpin probes include molecular torches and molecular beacons. A molecular torch probe comprises a target binding domain and a closing domain, which allow the molecular torch to exist in open and closed conformations, depending on whether the torch is bound to a target. (See also, U.S. Pat. Nos. 6,849,412; 6,835,542; 6,534,274; and 6,361,945). Molecular beacons are generally described in Tyagi et al., 1998, Nature Biotechnol. 16:49-53, and in U.S. Pat. Nos. 5,118,801; and 5,312,728. Methods for using such hairpin probes to detect the presence of a target sequence are well known in the art. In some instances, detection probes have a nucleotide sequence that is of the same sense as and comprises a target hybridizing sequence that is substantially identical to the target hybridizing sequence of the capture probe used in the assay. In other instances, the detection probes are configured to have a target hybridizing sequence that is substantially complementary to an amplification product, which, if using an extender primer, could comprise all or part of the extender primer's target hybridizing sequence or all or part of the extender primer's extension sequence.

Labeled detection probes can have an attached chemiluminescent marker, e.g., an acridinium ester (AE) compound (U.S. Pat. Nos. 5,185,439, 5,639,604, 5,585,481, and 5,656,744). The acridinium ester label is typically, attached to a central region of the probe near a region of A and T base pairs by using a non-nucleotide linker which restricts the amines of the nucleotide bases on both sides of the AE and provides a site for intercalation. Alternatively, an AE label may be attached to the 3' or 5' terminus of the detection probe, which is then used in conjunction with a second oligomer that hybridizes adjacent to the detection probe on the target nucleic acid to restrict the effects of nearby amine contributed by the target nucleic acid. Another embodiment attaches an AE label at or near the site of a mismatch with a related non-target polynucleotide sequence, to permit discrimination between the related sequence and the target sequence that may differ by only one nucleotide because the area of the duplex around the mismatch site is sufficiently destabilized to render the AE on the probe hybridized to the related non-target sequence susceptible to hydrolysis degradation. Also, labeled probes can be labeled at one end with a fluorescent label ("F") that absorbs light of a particular wavelength or range and emits light another emission wavelength or range and at the other end with a quencher ("Q") that dampens, partially or completely, signal emitted from the excited F when Q is in proximity with the fluorophore. Such a probe may be referred to as labeled with a fluorescent/quencher (F/Q) pair. Further, labeled probes can comprise an AE and an F or an AE and a Q for amplified or quenched signal.

"Homogeneous detectable label" refers to a label whose presence can be detected in a homogeneous manner depending on whether the label is bound or unbound to a target. A homogeneous detectable label can be detected in a "homogeneous reaction" without physically separating unbound forms of the label from the mixture before the detection step. It will be appreciated that a homogeneous reaction may occur in solution or on a support such as a microarray, biochip, or gene chip. Preferred homogeneous detectable labels and conditions for their detection are known (U.S. Pat. No. 5,283,174, Arnold et al.; U.S. Pat. No. 5,656,207, Woodhead et al.; U.S. Pat. No. 5,658,737, Nelson et al.).

An "immobilized probe" provides a means for joining a capture hybrid containing a target nucleic acid to a capture support. A preferred immobilized probe is a nucleic acid oligomer or polymer joined to a support, and which binds, directly or indirectly to a target nucleic acid to facilitate separation of the bound target nucleic acid from unbound material, such as other sample components. In a preferred embodiment, the target nucleic acid is indirectly bound to the immobilized probe via a target capture probe. Any of a variety of materials may be used as a capture support, e.g., matrices or particles made of nitrocellulose, nylon, glass, polyacrylate, mixed polymers, polystyrene, silane polypropylene, and magnetically attractable materials. Monodisperse magnetic spheres are a preferred embodiment of a capture support because they are relatively uniform in size and readily retrieved from solution by applying a magnetic force to the reaction container, preferably in an automated system. An immobilized probe may be linked directly to the capture support, e.g., by using any of a variety of covalent linkages, chelation, or ionic interaction, or may be linked indirectly via one or more linkers joined to the support.

A "capture probe," "target capture probe" or "target capture oligomer" provides a means for joining a target nucleic acid and an immobilized probe, preferably by hybridization of complementary sequences. A capture probe comprises a target hybridizing sequence and a binding member for attaching the capture probe, or a hybridization complex that includes the capture probe, to an immobilized probe. Such binding member may be a homopolymeric or substantially homopolymeric nucleotide sequence that is complementary to a sequence of an immobilized probe, or may be a first binding member of specific binding pair, wherein the second binding member is attached to a solid support (e.g., biotin and avidin or streptavidin). In a preferred embodiment, the first binding member is a substantially homopolymeric nucleotide sequence; more preferably, the substantially homopolymeric nucleotide sequence is poly-$T_{0-3}A_{5-30}$, and the second binding member is a sequence substantially complementary to the first such that the first and second binding members hybridize under appropriate conditions. (See e.g., U.S. Pat. No. 6,110,678 and PCT Pub. No. WO 06/07567, both of which are incorporated herein by reference).

Examples of capture probes are oligomers of DNA, RNA and/or analogs thereof that are comprised of target hybridizing sequences of at least 10 nucleotides complementary to a target nucleic acid. Target capture oligomers typically comprise a target hybridizing sequence of about 20 nucleotides. Target hybridizing regions can include at least one 2'-O-methyl residue structure to enhance binding to target nucleic acids. Embodiments of capture probes include oligomers that have a target hybridizing sequences of about 15 to 25 nucleotides covalently attached to a substantially homopolymeric sequence at the 3' and/or 5' end of the target hybridizing sequence. Some preferred capture probe embodiments include an oligomer that comprises a target hybridizing sequence flanked on both its 3' end and 5' end by substantially homopolymeric nucleic acid sequences of 10 to 30 nucleotides in length. Such preferred target capture oligomers can be diagrammed as: 5' $X_n$ a' b' c' $Y_n$ 3', in which $X_n$ indicates substantially homopolymeric sequence X that comprises n residues, a' b' c' indicates the target hybridizing sequence, and $Y_n$ indicates substantially homopolymeric sequence Y that comprises n residues. Preferably, n=about 10 to about 30 contiguous nucleotides in length. The $X_n$ and $Y_n$ sequences are configured to form a double-stranded stem structure so that the entire capture probe forms a hairpin structure with the target hybridizing sequence as the loop. Examples of hairpin capture probes include a 5' poly-dT region adjacent to the target hybridizing region and a 3' poly-dA region so that the target hybridizing region forms the loop of the hairpin structure when the poly-dT and poly-dA regions are bound to each other, as illustrated in FIG. 1. In this embodiment, the target hybridizing region remains substantially single-stranded in the hairpin structure. Those skilled in the art will understand that any complementary sequences located in the 5' and 3' regions may be used to flank the target hybridizing region in an oligomer that forms a hairpin capture probe structure.

Other capture probe embodiments include partially or completely double-stranded structures made up of two oligomer strands in which at least a portion of each of the individual single strands is complementary to a portion of the opposing single strand. Such embodiments can be diagramed as:

(first strand) 5' $X_n$ a' b' c' 3'
(second strand) 3' $Y_n$ a b c 5' in which a' b' c' indicates the target hybridizing sequence and a b c indicates an optional sequence complementary to the target hybridizing sequence, and in which the first and second strands can form a double-stranded structure. Such a capture probe is illustrated in FIG. 2. Other embodiments of capture probes are single-stranded oligomers made up of a 3' or 5' target hybridizing region and a contiguous region that binds to an immobilized probe, which can be diagramed as: 5' $X_n$ a' b' c' 3'; or 5' a' b' c' $X_n$ 3', in which $X_n$ indicates sequence X that comprises n residues, and a' b' c' indicates the target hybridizing sequence.

A "sample" or "biological sample" refers to any composition or mixture in which a target nucleic acid of interest may be present, including but not limited to plant or animal materials, waste materials, materials for forensic analysis, any tissue, cell, or extract derived from a living or dead organism which may contain a target nucleic acid, e.g., peripheral blood, bone marrow, plasma, serum, biopsy tissue including prostate, respiratory tissue or exudates, gastrointestinal tissue, urine, feces, semen, or other body fluids, and the like.

"Separating" or "isolating" or "purifying" refers to removing one or more components from a complex mixture, such as a sample. Sample components may include target and non-target nucleic acids, and other materials such as salts, acids, bases, detergents, proteins, carbohydrates, lipids and other organic or inorganic materials. Preferably, a separating, isolating or purifying step removes at least 70%, preferably at least 90%, and more preferably about 95% of the target nucleic acids away from other sample components. A separating, isolating or purifying step may optionally include additional washing steps to remove non-target sample components.

"Release" of a capture hybrid refers to separating one or more components of a capture hybrid from each other, such as separating a target nucleic acid from a target capture probe, and/or a target capture probe from an immobilized probe. Release of the target nucleic acid strand separates the target from other components of a capture hybrid and makes the target available for binding to a detection probe or amplification oligomer. Other components of the capture hybrid may remain bound, e.g., the capture probe strand to the immobilized probe on a capture support, without affecting target detection. Release of one or more capture hybrid components may be accomplished by changing one or more conditions to promote dissociation of components (e.g., heating to a certain Tm, changing salt concentrations, adding denaturants or competitive binding moieties to the mixture), or by using other well known methods such as strand displacement.

"Consisting essentially of" is used to mean that additional component(s), composition(s) or method step(s) that do not materially change the basic and novel characteristics of the present invention may be included in the compositions, kits or methods of the present invention. Such characteristics include the ability of a target hybridizing sequence of an oligomer to bind or hybridize specifically to a target nucleic acid in a sample, the ability of a capture hybrid to be separated from other sample components, or the ability of a detection probe to hybridize to the target nucleic acid and provide a detectable signal to indicate the presence of the target in a sample.

The term "configured to" denotes an actual arrangement of a reagent. For example, when used to discuss an oligonucleotide, configured to denotes an actual arrangement of the polynucleotide sequence configuration of the referenced oligonucleotide. An oligonucleotide configured to form a hairpin structure means that the nucleotide sequence of the oligonucleotide is arranged to form a stem portion and a loop portion under a set of conditions. Similarly, if two different oligonucleotides are configured to hybridize to a target sequence under a first or a second set of conditions it means that the nucleotide sequences of the two oligonucleotides are arranged to each hybridize to the target sequences under its defined set of conditions. When the term is used to discuss a set of conditions, then it denotes an actual arrangement of chemical and/or physical properties. For example, a set of conditions configured to cause a nucleic acid sequence to hybridize to another nucleic acid sequence, can mean an actual range of temperatures under which the hybridizations occurs.

An "amplification oligomer" is an oligomer, at least the 3'-end of which is complementary to a target nucleic acid ("target hybridizing sequence"), and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is a "promoter-based amplification oligomer," which comprises a target hybridizing sequence, and a promoter sequence for initiating transcription by an appropriate polymerase. Promoter-based amplification oligomers may or may not be extendable by a polymerase in a primer-based extension depending upon whether or not the 3' end of the target hybridizing sequence is modified to prevent primer-based extension (e.g., a 3' blocked end). A promoter-based amplification oligomer comprising a target hybridizing sequence that is not modified to prevent primer-based extension is referred to as a "promoter-primer." A promoter-based amplification oligonucleotide comprising a target hybridizing sequence that is modified to prevent primer-based extension is referred to as a "promoter-provider." Another example of an amplification oligomer is an extender primer comprising a 3' target hybridizing sequence and a 5' extension sequence. Preferably, but not necessarily, the extension sequence is configured to form a stem and a loop. Size ranges for amplification oligonucleotides include those comprising target hybridizing sequences that are about 8 to about 70 nt long. Included in this range are all whole numbers of the range, as is understood by a skilled artisan (e.g., 8, 9, 10, 11, 12, 13 . . . 67, 68, 69 and 70).

Oligomers not intended for primer-based extension by a nucleic acid polymerase may include a blocker group that replaces the 3'OH to prevent the enzyme-mediated extension of the oligomer in an amplification reaction. In some embodiments a blocking group near the 3' end and may be within five residues of the 3' end and is sufficiently large to limit binding of a polymerase to the oligomer. In other embodiments a blocking group is covalently attached to the 3' terminus. Many different chemical groups may be used to block the 3' end, e.g., alkyl groups, non-nucleotide linkers, alkane-diol dideoxynucleotide residues, and cordycepin.

As used herein, a "promoter" is a specific nucleic acid sequence that is recognized by a DNA-dependent RNA polymerase ("transcriptase") as a signal to bind to the nucleic acid and begin the transcription of RNA at a specific site.

As used herein, a "promoter-provider" or "provider" refers to an oligonucleotide comprising first and second regions, and which is modified to prevent the initiation of DNA synthesis from its 3'-terminus. The "first region" of a promoter-provider oligonucleotide comprises a base sequence which hybridizes to a DNA template, where the hybridizing sequence is situated 3', but not necessarily adjacent to, a promoter region. The target-hybridizing portion of a promoter oligonucleotide is typically at least 10 nucleotides in length, and may extend up to 50 or more nucleotides in length. The "second region" comprises a promoter sequence for an RNA polymerase. A promoter-provider oligonucleotide is configured so that it is incapable of being extended by an RNA- or DNA-dependent DNA polymerase, (e.g., reverse transcriptase), preferably by comprising a blocking moiety at its 3'-terminus as described above. This modification differentiates promoter providers from promoter primers. Preferably, the promoter portion of a promoter primer or provider is a promoter for a DNA-dependent RNA polymerase from *E. coli* and bacteriophages T7, T3, and SP6, though other promoters or modified version thereof can be used as well.

By "preferentially hybridize" is meant that under stringent hybridization assay conditions, an oligonucleotide hybridizes to its target sequences, or replicates thereof, to form stable oligonucleotide: target sequence hybrid, while at the same time formation of stable oligonucleotide: non-target sequence hybrid is minimized. For example, a probe oligonucleotide preferentially hybridizes to a target sequence or replicate thereof to a sufficiently greater extent than to a non-target sequence, to enable one having ordinary skill in the art to accurately detect the RNA replicates or complementary DNA (cDNA) of the target sequence formed during the amplification. Appropriate hybridization conditions are well known in the art for probe, amplification, target capture, blocker and other oligonucleotides, may be predicted based on sequence composition, or can be determined by using routine testing methods (e.g., Sambrook et al., Molecular Cloning, A Laboratory Manual, 2nd ed. (Cold Spring Harbor Laboratory Press, Cold Spring Harbor, N.Y., 1989) at §§1.90-1.91, 7.37-7.57, 9.47-9.51 and 11.47-11.57, particularly §§9.50-9.51, 11.12-11.13, 11.45-11.47 and 11.55-11.57).

FIG. 1 illustrates a method embodiment that uses a capture probe configured to form a hairpin structure that is partially double-stranded and contains a single-stranded loop region that includes the target hybridizing sequence. The capture probe comprises complementary 5' and 3' sequences (shown as poly-T and poly-A), which are configured to form the double-stranded stem portion of the hairpin. These homopolymeric sequences flank the target hybridizing sequence (shown as a' b' c' d', wherein a, b, c & d are merely indicators that a sequence is present, but alone do not denote and nucleotide arrangement, and wherein the presence or absence of ' indicates polarity such that a' b' c' d' is a nucleic acid sequence that is substantially complementary to a b c d), which is configured to form the loop. In this embodiment, the 5' and 3' ends of the hairpin capture probe are separated under a set of conditions (e.g., heating above the Tm to dissociate the hydrogen bonds) to make a linear single-stranded capture probe. The now linear capture probe hybridizes with a target nucleic acid (shown as sequence d c b a) under a set of conditions. If the target nucleic acid is a double-stranded molecule, then it first can be dissociated into single stranded molecules using standard chemical or physical methods. For example, the double strands of the target nucleic acid can be melted in a single melting step that linearizes the capture probe and dissociates double stranded target nucleic acid strands before hybridization of the capture probe and the target strand. Following capture of the target nucleic acid by the capture probe, excess capture probe, e.g., those not hybridized to target nucleic acids, reform the hairpin structure under a set of conditions to effectively prevent non-specific binding of these excess capture probes to other components in the mixture, or to the immobilized probe.

In this embodiment, the capture hybrid is made up of the target nucleic acid hybridized to the target hybridizing sequence of the capture probe and one of the substantially heteropolymeric sequences of the capture probe (here illustrated as a 3' poly-A) hybridized to a complementary immobilized probe (here illustrated as a poly-T) attached to the capture support. One or more of these hybridization steps can be performed sequentially or simultaneously depending on the conditions used and/or the configuration of these oligonucleotides. Following formation of the capture hybrid, the capture hybrid is isolated from other sample components, including excess hairpin capture probes, non-target nucleic acids and cellular debris, by physically separating the capture support from these components using any of a variety of known methods, e.g., centrifugation, filtration, magnetic attraction of a magnetic capture support. To further facilitate isolation of the target nucleic acid from other sample components that adhere non-specifically to any portion of the capture hybrid, the capture hybrid may be washed one or more times to dilute and remove other sample components. Washing may be accomplished by dissociating the capture hybrid into its individual components in an appropriate aqueous solution (e.g., 10 mM Tris, 1 mM EDTA) and appropriate conditions (e.g., temperature above the Tm of the components) and then readjusting the conditions to permit reformation of the capture hybrid. For ease of handling and minimization of steps, washing preferably rinses the intact capture hybrid attached to the capture support in a solution by using conditions that maintain the capture hybrid.

The method next proceeds by releasing the target from the capture hybrid. For example, the capture hybrid is released into its individual components to free the target nucleic acid into solution, making it available to hybridize with a detection probe or a first primer oligomer, depending on whether or not an amplification step is to be performed before detection. In FIG. 1 the capture probe and target nucleic acid are illustrated as being released into a solution for detection of the target nucleic acid. The capture probe and the detection probe are illustrated as comprising the same target hybridizing sequence, and thus can compete for hybridization to the target nucleic acid. To prevent competition by the capture probe for hybridizing to the target nucleic acid, a set of conditions are provided for forming a hairpin structured capture probe. The detection probe is then hybridized to the target under a set of conditions and the presence or absence or abundance of the target nucleic acid is determined. An intervening amplification step could have followed the step releasing the capture probe and target nucleic acid into solution. An amplification step requires that a first amplification oligomer hybridize the target nucleic acid. Here, the amplification oligomer and the capture probe both comprise target hybridizing sequences that compete for hybridizing the small target nucleic acid, thus these oligonucleotides comprise substantially identical target hybridizing sequences, or at least target hybridizing sequences configured to hybridize to overlapping target sequences on the small target nucleic acid. To prevent competition by the capture probe for hybridizing to the target nucleic acid, a set of conditions are provided for forming a hairpin structured capture probe. The amplification oligomer is then hybridized to the target nucleic acid under a set of conditions and the target nucleic acid is amplified. The second amplification oligomer may comprise a target hybridizing sequence that is complementary to all or a portion of the target capture oligomer target hybridizing sequence. Thus, the target capture oligomer can interfere with the second amplification oligomer hybridizing to its intended target sequence.

FIG. 2 illustrates a method embodiment in which the target nucleic acid is captured by using a completely or partially double-stranded capture probe that contains complementary sequences on two strands (shown as a 3' poly-A region on one strand and a 5' poly-T region on the other strand) and at least one target hybridizing sequence (shown as a' b' c' on the poly-T containing strand). In this embodiment, only one strand of the capture probe hybridizes to the target nucleic acid (shown as sequence a b c d e). It is important that the capture probe strand that binds to the target sequence also contains a specific binding partner member that binds to the immobilized probe (shown as a poly-A strand on the capture support). The partially double-stranded capture probe is usually dissociated before forming the capture hybrid although strand displacement caused by the target binding to the target hybridizing sequence of the capture probe may separate the capture probe strands. FIG. 2 illustrates a completely double-stranded embodiment in which the two strands contain portions that are complementary to each other (shown as poly-A on one strand, and poly-T on the other strand), and one strand contains a target hybridizing sequence whereas the other strand contain a sequence complementary to the target hybridizing sequence. Those skilled in the art will appreciate that the capture probe may be partially double-stranded (e.g., substituting a polyA strand for the polyA-a b c strand shown in FIG. 2). For completely and partially double-stranded capture probes, the same assay steps are used, optionally starting with separation of the capture probe strands using standard methods to allow hybridization of the target hybridizing portion of one capture probe strand to the target nucleic acid. Because the two capture probe strands can rehybridize (e.g., via poly-A binding to polyT) and interfere with the target hybridizing sequence of the capture probe strand binding to the target nucleic acid, those skilled in the art will appreciate that the capture probe may be synthesized with modifications to optimize hybridization to the target nucleic acid.

In this embodiment, the capture hybrid is made up of the target nucleic acid hybridized to the target hybridizing sequence of one capture probe strand, and another portion of the same capture probe strand (shown as poly-T) is bound to an immobilized probe (shown as poly-A) attached to a capture support. As described above, the capture hybrid attached to the support is separated from other sample components and, optionally, washed to remove sample components and capture probe strands unbound to the capture hybrid. Capture probe strands that do not bind to the target sequence can reform the partially or completely double-stranded structure and be washed away, along with unbound single strands. Then, the target nucleic acid is released from the capture hybrid or the capture hybrid is separated into its components, and the released target is bound in solution by a detection probe (shown as sequence a' b' c' d' e') to form a detection hybrid that produces a signal (shown as a star structure) which is detected to indicate the presence of the target nucleic acid in the sample. The released capture probe strand from the capture hybrid remains in solution as illustrated in FIG. 2, but does not bind the detection probe because it is the same sense strand as the detection probe. Similarly, if an amplification step is to be performed before the detection step, then the amplification oligomer comprises all or part of the a'b'c'd'e' target hybridizing sequence and competes with the capture probe for hybridizing the target nucleic acid. Those skilled in the art will appreciate that the detection probe or amplification oligomer are configured to include structure that favors its binding to the target nucleic acid (e.g., increased sequence length and/or backbone modifications) to minimize competition between with the released capture probe strand. In an embodiment, the released capture probe can be used as a primer member in an amplification reaction. In one aspect, the released capture probe sequence can comprise a promoter sequence and can be used as a promoter-based amplification oligomer.

A typical assay that uses a method described herein involves providing a sample suspected of containing one or more small RNAs of interest. Such a sample may be used directly in the assay or prepared by using any of a variety of methods, from simple dilution of a biological fluid with a lysing solution to more complex methods that are well known in the art (e.g., Su et al., J. Mol. Diagn. 2004, 6:101-107; Sambrook, J. et al., 1989, Molecular Cloning, A Laboratory Manual, 2nd ed., pp. 7.37-7.57; and U.S. Pat. Nos. 5,374,522, 5,386,024, 5,786,208, 5,837,452, and 6,551,778). Typically, a sample is heated to inactivate enzymes in the sample and to make the nucleic acids in the sample single-stranded (e.g., 90-100.deg.C. for 2-10 min, then rapidly cooling to 0-5.deg.C.). To form a capture hybrid, the sample is incubated in appropriate hybridization conditions in the presence of a capture probe (preferably of a configuration described above) and an immobilized probe attached to a capture support. An efficient method mixes these components together in a hybridization reaction mixture and uses first conditions to promote hybridization between the target hybridizing sequence of a capture probe and the target nucleic acid, followed by second conditions to promote binding of the capture probe:target nucleic acid complex to the immobilized probe. For example, the first conditions may incubate the reaction mixture at a temperature below the Tm for the target hybridizing sequence of the capture probe and the target nucleic acid but above the Tm for hybridization of sequences that bind the capture probe and the immobilized probe, followed by incubating at a second temperature below the Tm for the capture probe binding to immobilized probe sequences (U.S. Pat. No. 6,110,678). In embodiments in which the capture hybrid is attached to the capture support by using members of a specific binding pair that do not require nucleic acid hybridization (e.g., biotin and avidin or streptavidin), appropriate conditions for the selected binding pair members are used. An alternate approach incubates the target capture oligomer and the target nucleic acid under conditions configured to open the hairpin capture probe, hybridize the capture probe and the target nucleic acid, and then reform a hairpin structure for any unhybridized capture probe. Then, an immobilized probe and support are mixed into the reaction mixture in conditions configured to hybridize the target capture oligomer:target nucleic acid complex and the immobilized probe to obtain a capture hybrid. Following formation of the capture hybrids, the capture hybrids attached to the capture support are separated physically from other sample components by using well known methods appropriate for the support, e.g., removing a filter, membrane, or particle from the solution phase by using filtration, centrifugation, gravity, magnetic force, and the like. When the capture support with attached capture hybrids have been separated from other sample components, optional washing steps may be included to further purify the captured target nucleic acid, preferably performed while maintaining the capture hybrid attached to the capture support. Then the target nucleic acid or all components of the capture hybrid are released into solution to free the target for the detection step. Release of the target or capture hybrid components may be performed by any known method, such as, e.g., changing the temperature or chemical composition of the mixture to promote dissociation of the capture hybrid into one or more of its nucleic acid components. Typically, a simple heating step is performed to melt the target and capture probe strands, e.g., in an aqueous solution of low ionic strength, at 90-100.deg.C. for 5 min, followed by rapid cooling to 0-5.deg.C. As illustrated in FIG. 1, the capture probe is reformed via intramolecular hybridization to a hairpin form. The subsequent amplification and/or detection step may be performed in soluble phase by adding a detection probe/amplification oligomer directly to the soluble phase containing the released target nucleic acid and incubating the mixture in hybridization conditions configured for binding the detection probe/ amplification oligomer and target sequences (e.g., adding salts to the soluble phase to make a solution of suitable ionic strength and incubating at 25-60.deg.C.). After the detection probe binds to the target nucleic acid to form the detection hybrid, a signal from the hybrid is detected to indicate the presence of the target in the tested sample.

The invention includes compositions useful for performing the methods of detecting target nucleic acids described herein. Some compositions herein include one or more target capture oligomers for hybridizing to a target nucleic acid. In some methods for detecting the presence or abundance of two or more target nucleic acids, composition includes two or more target capture oligomers each configured to selectively hybridize each of their respective target nucleic acids. Some target capture oligomers are configured in a 5' $X_n$ a' b' c' $Y_n$ 3' format, wherein a'b'c' is substantially complementary to all or a portion of a micro RNA and wherein X and Y are substantially homopolymeric nucleic acid sequences that are complementary one to the other. Some target capture oligomers are configured in a 5' $X_n$ a' b' c' $Y_n$ 3' format, wherein a'b'c' is substantially complementary to all or a portion of miR-21 and wherein X and Y are substantially homopolymeric nucleic acid sequences that are complementary one to the other. Some target capture oligomers are configured in a 5' $X_n$ a' b' c' $Y_n$ 3' format, wherein a'b'c' is substantially complementary to all or a portion of miR-34b and wherein X and Y are substantially homopolymeric nucleic acid sequences that are complementary one to the other. Some target capture oligomers are configured in a 5' X.sub.n a' b' c' Y.sub.n 3' format, wherein a'b'c' is substantially complementary to all or a portion of miR-182 and wherein X and Y are substantially homopolymeric nucleic acid sequences that are complementary one to the other. Some target capture oligomers are configured in a 5' X.sub.n a' b' c' Y.sub.n 3' format, wherein a'b'c' is substantially complementary to all or a portion of miR-221 and wherein X and Y are substantially homopolymeric nucleic acid sequences that are complementary one to the other. Some target capture oligomers are configured in a 5' X.sub.n a' b' c' Y.sub.n 3' format, wherein a'b'c' is substantially complementary to all or a portion of miR-222 and wherein X and Y are substantially homopolymeric nucleic acid sequences that are complementary one to the other. Some target capture oligomers are configured in a 5' X.sub.n a' b' c' Y.sub.n 3' format, wherein a'b'c' is substantially complementary to all or a portion of miR-802 and wherein X and Y are substantially homopolymeric nucleic acid sequences that are complementary one to the other.

Some compositions herein include one or more first amplification oligomers for hybridizing to a target nucleic acid. In some methods for detecting the presence or abundance of two or more target nucleic acids, composition includes two or more first amplification oligomers each configured to selectively hybridize each of their respective target nucleic acids. Some first amplification oligomers are configured in a 5' Z.sub.n a' b' c' 3' format, wherein a' b' c' is substantially complementary to all or a portion of a micro RNA sequence and wherein Z is an extension nucleic acid sequence. The a' b' c' region of the first amplification oligomer can be substantially complementary to is the entire micro RNA sequence. The a'b'c' region of the first amplification oligomer can be substantially complementary to a portion of a micro RNA, wherein the portion is up to 20 contiguous nucleotides of the micro RNA sequence. The a'b'c' region of the first amplification oligomer can be substantially complementary to a portion of a micro RNA, wherein the portion is up to 20 contiguous nucleotides of the micro RNA sequence. The a'b'c' region of the first amplification oligomer can be substantially complementary to a portion of a micro RNA, wherein the portion is up to 15 contiguous nucleotides of the micro RNA sequence. The a'b'c' region of the first amplification oligomer can be substantially complementary to a portion of a micro RNA, wherein the portion is up to 10 contiguous nucleotides of the micro RNA sequence. The a'b'c' region of the first amplification oligomer can be substantially complementary to a portion of a micro RNA, wherein the portion is 5, 6, 7, 8, 9, 10, 11, 12, 13, 14, 15, 16, 17, 18, 19, 20, 21, 22, 23, 24, 25, 26 or 27 contiguous nucleotides of the micro RNA sequence. The a'b'c' region of the first amplification oligomer can be substantially complementary to a portion of a micro RNA, wherein the portion is the 5, 6, 7, 8, 9, 10, 11, 12, 13, 14, 15, 16, 17, 18, 19, 20, 21, 22, 23, 24, 25, 26 or 27 contiguous nucleotides at the 3' end of the micro RNA sequence. Preferably, the 5' Z.sub.n region of the first amplification primer is configured to form a hairpin structure. The 5' Z.sub.n region of the first amplifications primer can be configured to contain a target sequence or complement thereof for hybridizing a reverse primer oligomer or a detection probe oligomer or both. Some first amplification oligomers are configured in a 5' Z.sub.n a' b' c' 3' format, wherein a'b'c' is substantially complementary to all or a portion of a miR-21 sequence and wherein Z is an extension nucleic acid sequence. Some first amplification oligomers are configured in a 5' Z.sub.n a' b' c' 3' format, wherein a'b'c' is substantially complementary to all or a portion of a miR-34b sequence and wherein Z is an extension nucleic acid sequence. Some first amplification oligomers are configured in a 5' Z.sub.n a' b' c' 3' format, wherein a'b'c' is substantially complementary to all or a portion of a miR-182 sequence and wherein Z is an extension nucleic acid sequence. Some first amplification oligomers are configured in a 5' Z.sub.n a' b' c' 3' format, wherein a'b'c' is substantially complementary to all or a portion of a miR-221 sequence and wherein Z is an extension nucleic acid sequence. Some first amplification oligomers are configured in a 5' Z.sub.n a' b' c' 3' format, wherein a'b'c' is substantially complementary to all or a portion of a miR-222 sequence and wherein Z is an extension nucleic acid sequence. Some first amplification oligomers are configured in a 5' Z.sub.n a' b' c' 3' format, wherein a'b'c' is substantially complementary to all or a portion of a miR-802 sequence and wherein Z is an extension nucleic acid sequence.

Some compositions herein include at least one promoter-based oligomer for hybridizing to a cDNA containing the substantial complement of a target nucleic acid sequence. In some methods for detecting the presence or abundance of two or more target nucleic acids the composition includes two or more promoter-based oligomers each configured to selectively hybridize a cDNA containing the substantial complement their respective target nucleic acid. Some promoter-based oligomers are configured in a 5' promoter a b c 3' format, wherein a b c is substantially identical to all or a portion of a micro RNA sequence and wherein the promoter is an RNA polymerase promoter sequence. The a b c region of the promoter-based oligomer can be substantially identical to the entire micro RNA sequence. The a b c region of the promoter-based oligomer can be substantially identical to a portion of a micro RNA, wherein the portion is up to 20 contiguous nucleotides of the micro RNA sequence. The a b c region of the promoter-based oligomer can be substantially identical to a portion of a micro RNA, wherein the portion is up to 20 contiguous nucleotides of the micro RNA sequence. The a b c region of the promoter-based oligomer can be substantially identical to a portion of a micro RNA, wherein the portion is up to 15 contiguous nucleotides of the micro RNA sequence. The a b c region of the promoter-based oligomer can be substantially identical to a portion of a micro RNA, wherein the portion is up to 10 contiguous nucleotides of the micro RNA sequence. The a b c region of the promoter-based oligomer can be substantially identical to a portion of a micro RNA, wherein the portion is 5, 6, 7, 8, 9, 10, 11, 12, 13, 14, 15, 16, 17, 18, 19, 20, 21, 22, 23, 24, 25, 26 or 27 contiguous nucleotides of the micro RNA sequence. The a b c region of the promoter-based oligomer can be substantially identical to a portion of a micro RNA, wherein the portion is the 5, 6, 7, 8, 9, 10, 11, 12, 13, 14, 15, 16, 17, 18, 19, 20, 21, 22, 23, 24, 25, 26 or 27 contiguous nucleotides at the 5' end of the micro RNA sequence. Some promoter-based oligomers are configured in a 5' promoter a b c 3' format, wherein a b c is substantially identical to all or a portion of a miR-21 sequence. Some promoter-based oligomers are configured in a 5' promoter a b c 3' format, wherein a b c is substantially identical to all or a portion of a miR-34b sequence. Some promoter-based oligomers are configured in a 5' promoter a b c 3' format, wherein a b c is substantially identical to all or a portion of a miR-182 sequence. Some promoter-based oligomers are configured in a 5' promoter a b c 3' format, wherein a b c is substantially identical to all or a portion of a miR-221 sequence. Some promoter-based oligomers are configured in a 5' promoter a b c 3' format, wherein a b c is substantially identical to all or a portion of a miR-222 sequence. Some promoter-based oligomers are configured in a 5' promoter a b c 3' format, wherein a b c is substantially identical to all or a portion of a miR-802 sequence. Some promoter-based oligomers can optionally comprise a tag sequence between the 5' promoter region and the 3' a b c region. In some methods for amplification using a universal amplification oligomer, a first promoter-based oligomer comprises a tag sequence between the 5' promoter region and the 3' a b c region and a second promoter-based oligomer is configured to hybridize to the complement of that tag sequence. In some methods for detecting the presence or abundance of two or more target nucleic acids, the composition includes two or more promoter-based oligomers each configured to selectively hybridize a cDNA containing the substantial complement their respective target nucleic acids, wherein each of the two or more promoter based oligomers comprise a tag sequence between their 5' promoter regions and their 3' a b c regions. In some methods for detecting the presence or abundance of two or more target nucleic acids, the composition includes two or more promoter-based oligomers each configured to selectively hybridize a cDNA containing the substantial complement their respective target nucleic acids, wherein each of the two or more promoter based oligomers comprise a tag sequence between their 5' promoter regions and their 3' a b c regions and wherein each of the tag sequences in each of these two or more promoter-based oligomers are substantially identical. In some methods for detecting the presence or abundance of two or more target nucleic acids, the composition includes two or more promoter-based oligomers each configured to selectively hybridize a cDNA containing the substantial complement their respective target nucleic acids, wherein each of the two or more promoter based oligomers comprise a tag sequence between their 5' promoter regions and their 3' a b c regions and wherein each of the tag sequences in each of these two or more promoter-based oligomers are substantially identical and wherein the composition further includes an additional promoter based oligomer comprising a target hybridizing sequence that is also substantially identical to the tag sequences. Some compositions include at least one promoter-based oligomer that is a promoter primer. Some compositions include at least one promoter-based oligomer that is a promoter provider.

Some compositions include at least one detection probe oligomer for hybridizing to a target nucleic acid sequence. In some methods for detecting the presence or abundance of two or more target nucleic acids, the composition includes contain two or more detection probe oligomers each configured to selectively hybridize each of their respective target nucleic acids. Some detection probe oligomers for hybridizing to a target nucleic acid sequence are linear probes. Some detection probe oligomers are labeled linear probes. Some detection probe oligomers are dual labeled linear probes. Some detection probe oligomers are hairpin probes. Some detection probe oligomers are labeled hairpin probe. Some detection probe oligomers are dual labeled hairpin probe. Some detection probe oligomers are molecular beacons. Some detection probe oligomers are molecular torches. Some detection probe oligomers comprise a target hybridizing region that is substantially complementary to all or a portion of a micro RNA. Some detection probe oligomers comprise a target hybridizing region that is substantially complementary to a portion of a micro RNA, wherein the portion is 5, 6, 7, 8, 9, 10, 11, 12, 13, 14, 15, 16, 17, 18, 19, 20, 21, 22, 23, 24, 25, 26 or 27 contiguous nucleotides of the micro RNA. Some detection probe oligomers comprise a target hybridizing region that is substantially complementary to a portion of a micro RNA, wherein the portion is 5, 6, 7, 8, 9, 10, 11, 12, 13, 14, 15, 16, 17, 18, 19, 20, 21, 22, 23, 24, 25, 26 or 27 contiguous nucleotides at the 3' end of the micro RNA. Some detection probe oligomers comprise a target hybridizing region that is substantially complementary to a portion of a micro RNA, wherein the portion is 5, 6, 7, 8, 9, 10, 11, 12, 13, 14, 15, 16, 17, 18, 19, 20, 21, 22, 23, 24, 25, 26 or 27 contiguous nucleotides at the 5' end of the micro RNA. Some detection probe oligomers comprise a target hybridizing region that is substantially complementary to all or a portion of miR-21. Some detection probe oligomers comprise a target hybridizing region that is substantially complementary to all or a portion of miR-34b. Some detection probe oligomers comprise a target hybridizing region that is substantially complementary to all or a portion of miR-182. Some detection probe oligomers comprise a target hybridizing region that is substantially complementary to all or a portion of miR-221. Some detection probe oligomers comprise a target hybridizing region that is substantially complementary to all or a portion of miR-222. Some detection probe oligomers comprise a target hybridizing region that is substantially complementary to all or a portion of miR-802. Some detection probe oligomers are configured to hybridize to an amplification product generated from a micro RNA template. Some detection probe oligomers are configured to hybridize to an amplification product generated from a micro RNA template using an amplification oligomer described herein. Some detection probe oligomers are configured to hybridize to an amplification product generated from a micro RNA template using an amplification oligomer selected from a first amplification oligomer as described herein, a promoter-based oligomer as described herein, a reverse primer oligomer as described herein or combinations thereof. Some detection probe oligomers are configured to hybridize to an amplification product generated from a micro RNA template using a first amplification oligomer in a 5' $Z_n$ a' b' c' 3' format as described herein, wherein the detection probe oligomer comprises a target hybridizing sequence that is substantially complementary to a portion of the extension nucleic acid sequence. Some detection probe oligomers are configured to hybridize to an amplification product generated from a micro RNA template using a first amplification oligomer in a 5' $Z_n$ a' b' c' 3' format as described herein, wherein the detection probe oligomer comprises a target hybridizing region that is substantially identical to all or a portion of the micro RNA template. Some detection probe oligomers are configured to hybridize to an amplification product generated from a micro RNA template using a first amplification oligomer in a 5' $Z_n$ a' b' c' 3' format as described herein, wherein the detection probe oligomer comprises a target hybridizing region that is substantially complementary to a portion of the extension nucleic acid sequence and to all or a portion of the amplification product sequence that is itself complementary to the micro RNA template. Some detection probe oligomers are configured to hybridize to an amplification product generated from a micro RNA template using a promoter-based oligomer as described herein, wherein the detection probe oligomer comprises a target hybridizing sequence that is substantially identical to all or a portion of the target hybridizing sequence of the promoter-based oligomer. Some detection probe oligomers are configured to hybridize to an amplification product generated from a micro RNA template using a promoter-based oligomer containing a tag sequence as described herein, wherein the detection probe oligomer comprises a target hybridizing sequence that is substantially identical to all or a portion of the target hybridizing sequence of the promoter-based oligomer, all or a portion of the tag sequence or a combination thereof. Some detection probe oligomers are configured to hybridize to an amplification product generated from a micro RNA template using a promoter-based oligomer as described herein, wherein the detection probe oligomer comprises a target hybridizing region that is substantially complementary to an RNA transcript amplification product.

The invention also includes kits containing components for performing the methods for detecting target nucleic acids described herein. Some kits contain at least one target capture oligomer for hybridizing to a target nucleic acid. Some kits for detecting the presence or abundance of two or more target nucleic acids contain two or more target capture oligomers each configured to selectively hybridize each of their respective target nucleic acids. Some kits contain at least one target capture oligomer in a 5' $X_n$ a' b' c' $Y_n$ 3' format, wherein a'b'c' is substantially complementary to all or a portion of a micro RNA and wherein X and Y are substantially homopolymeric nucleic acid sequences that are complementary one to the other. Some kits contain at lease one target capture oligomer in a 5' $X_n$ a' b' c' $Y_n$ 3' format, wherein a'b'c' is substantially complementary to all or a portion of miR-21 and wherein X and Y are substantially homopolymeric nucleic acid sequences that are complementary one to the other. Some kits contain at lease one target capture oligomer in a 5' $X_n$ a' b' c' $Y_n$ 3' format, wherein a'b'c' is substantially complementary to all or a portion of miR-34b and wherein X and Y are substantially homopolymeric nucleic acid sequences that are complementary one to the other. Some kits contain at lease one target capture oligomer in a 5' $X_n$ a' b' c' $Y_n$ 3' format, wherein a'b'c' is substantially complementary to all or a portion of miR-182 and wherein X and Y are substantially homopolymeric nucleic acid sequences that are complementary one to the other. Some kits contain at lease one target capture oligomer in a 5' $X_n$ a' b' c' $Y_n$ 3' format, wherein a'b'c' is substantially complementary to all or a portion of miR-221 and wherein X and Y are substantially homopolymeric nucleic acid sequences that are complementary one to the other. Some kits contain at lease one target capture oligomer in a 5' $X_n$ a' b' c' $Y_n$ 3' format, wherein a'b'c' is substantially complementary to all or a portion of miR-222 and wherein X and Y are substantially homopolymeric nucleic acid sequences that are complementary one to the other. Some kits contain at lease one target capture oligomer in a 5' $X_n$ a' b' c' $Y_n$ 3' format, wherein a'b'c' is substantially complementary to all or a portion of miR-802 and wherein X and Y are substantially homopolymeric nucleic acid sequences that are complementary one to the other.

Some kits contain at least one first amplification oligomer for hybridizing to a target nucleic acid. Some kits for detecting the presence or abundance of two or more target nucleic acids contain two or more first amplification oligomers each configured to selectively hybridize each of their respective target nucleic acids. Some kits contain at least one first amplification oligomer in a 5' $Z_n$ a' b' c' 3' format, wherein a' b' c' is substantially complementary to all or a portion of a micro RNA sequence and wherein Z is an extension nucleic acid sequence. Preferably, the a' b' c' region of the first amplification oligomer is substantially complementary to is the entire micro RNA sequence. Preferably, the a'b'c' region of the first amplification oligomer is substantially complementary to a portion of a micro RNA, wherein the portion is up to 20 contiguous nucleotides of the micro RNA sequence. Preferably, the a'b'c' region of the first amplification oligomer is substantially complementary to a portion of a micro RNA, wherein the portion is up to 20 contiguous nucleotides of the micro RNA sequence. Preferably, the a'b'c' region of the first amplification oligomer is substantially complementary to a portion of a micro RNA, wherein the portion is up to 15 contiguous nucleotides of the micro RNA sequence. Preferably, the a'b'c' region of the first amplification oligomer is substantially complementary to a portion of a micro RNA, wherein the portion is up to 10 contiguous nucleotides of the micro RNA sequence. Preferably, the a'b'c' region of the first amplification oligomer is substantially complementary to a portion of a micro RNA, wherein the portion is 5, 6, 7, 8, 9, 10, 11, 12, 13, 14, 15, 16, 17, 18, 19, 20, 21, 22, 23, 24, 25, 26 or 27 contiguous nucleotides of the micro RNA sequence. Preferably, the a'b'c' region of the first amplification oligomer is substantially complementary to a portion of a micro RNA, wherein the portion is the 5, 6, 7, 8, 9, 10, 11, 12, 13, 14, 15, 16, 17, 18, 19, 20, 21, 22, 23, 24, 25, 26 or 27 contiguous nucleotides at the 3' end of the micro RNA sequence. Preferably, the 5'$Z_n$ region of the first amplification primer is configured to form a hairpin structure. Preferably, the 5'$Z_n$ region of the first amplifications primer is configured to contain a target sequence or complement thereof for hybridizing a reverse primer oligomer or a detection probe oligomer or both. Some kits contain at least one first amplification oligomer in a 5' $Z_n$ a' b' c' 3' format, wherein a'b'c' is substantially complementary to all or a portion of a miR-21 sequence and wherein Z is an extension nucleic acid sequence. Some kits contain at least one first amplification oligomer in a 5' $Z_n$ a' b' c' 3' format, wherein a'b' c' is substantially complementary to all or a portion of a miR-34b sequence and wherein Z is an extension nucleic acid sequence. Some kits contain at least one first amplification oligomer in a 5' $Z_n$ a' b' c' 3' format, wherein a'b'c' is substantially complementary to all or a portion of a miR-182 sequence and wherein Z is an extension nucleic acid sequence. Some kits contain at least one first amplification oligomer in a 5' $Z_n$ a' b' c' 3' format, wherein a'b'c' is substantially complementary to all or a portion of a miR-221 sequence and wherein Z is an extension nucleic acid sequence. Some kits contain at least one first amplification oligomer in a 5' $Z_n$ a' b' c' 3' format, wherein a'b'c' is substantially complementary to all or a portion of a miR-222 sequence and wherein Z is an extension nucleic acid sequence. Some kits contain at least one first amplification oligomer in a 5' $Z_n$ a' b' c' 3' format, wherein a'b'c' is substantially complementary to all or a portion of a miR-802 sequence and wherein Z is an extension nucleic acid sequence.

Some kits contain at least one promoter-based oligomer for hybridizing to a cDNA containing the substantial complement of a target nucleic acid sequence. Some kits for detecting the presence or abundance of two or more target nucleic acids contain two or more promoter-based oligomers each configured to selectively hybridize a cDNA containing the substantial complement their respective target nucleic acid. Some kits contain at least one promoter-based oligomer in a 5' promoter a b c 3' format, wherein a b c is substantially identical to all or a portion of a micro RNA sequence and wherein the promoter is an RNA polymerase promoter sequence. Preferably, the a b c region of the promoter-based oligomer is substantially identical to the entire micro RNA sequence. Preferably, the a b c region of the promoter-based oligomer is substantially identical to a portion of a micro RNA, wherein the portion is up to 20 contiguous nucleotides of the micro RNA sequence. Preferably, the a b c region of the promoter-based oligomer is substantially identical to a portion of a micro RNA, wherein the portion is up to 20 contiguous nucleotides of the micro RNA sequence. Preferably, the a b c region of the promoter-based oligomer is substantially identical to a portion of a micro RNA, wherein the portion is up to 15 contiguous nucleotides of the micro RNA sequence. Preferably, the a b c region of the promoter-based oligomer is substantially identical to a portion of a micro RNA, wherein the portion is up to 10 contiguous nucleotides of the micro RNA sequence. Preferably, the a b c region of the promoter-based oligomer is substantially identical to a portion of a micro RNA, wherein the portion is 5, 6, 7, 8, 9, 10, 11, 12, 13, 14, 15, 16, 17, 18, 19, 20, 21, 22, 23, 24, 25, 26 or 27 contiguous nucleotides of the micro RNA sequence. Preferably, the a b c region of the promoter-based oligomer is substantially identical to a portion of a micro RNA, wherein the portion is the 5, 6, 7, 8, 9, 10, 11, 12, 13, 14, 15, 16, 17, 18, 19, 20, 21, 22, 23, 24, 25, 26 or 27 contiguous nucleotides at the 5' end of the micro RNA sequence. Some kits contain at least one promoter-based oligomer in a 5' promoter a b c 3' format, wherein a b c is substantially identical to all or a portion of a miR-21 sequence. Some kits contain at least one promoter-based oligomer in a 5' promoter a b c 3' format, wherein a b c is substantially identical to all or a portion of a miR-34b sequence. Some kits contain at least one promoter-based oligomer in a 5' promoter a b c 3' format, wherein a b c is substantially identical to all or a portion of a miR-182 sequence. Some kits contain at least one promoter-based oligomer in a 5' promoter a b c 3' format, wherein a b c is substantially identical to all or a portion of a miR-221 sequence. Some kits contain at least one promoter-based oligomer in a 5' promoter a b c 3' format, wherein a b c is substantially identical to all or a portion of a miR-222 sequence. Some kits contain at least one promoter-based oligomer in a 5' promoter a b c 3' format, wherein a b c is substantially identical to all or a portion of a miR-802 sequence. Some kits can optionally contain a tag sequence between the 5' promoter region and the 3' a b c region. Some kits can optionally contain a tag sequence between the 5' promoter region and the 3' a b c region and a secondary promoter-based oligomer configured to hybridize to the complement of the tag sequence. Some kits for detecting the presence or abundance of two or more target nucleic acids contain two or more promoter-based oligomers each configured to selectively hybridize a cDNA containing the substantial complement their respective target nucleic acids, wherein each of the two or more promoter based oligomers contain a tag sequence between their 5' promoter regions and their 3' a b c regions. Some kits for detecting the presence or abundance of two or more target nucleic acids contain two or more promoter-based oligomers each configured to selectively hybridize a cDNA containing the substantial complement their respective target nucleic acids, wherein each of the two or more promoter based oligomers contain a tag sequence between their 5' promoter regions and their 3' a b c regions and wherein each of the tag sequences in each of these two or more promoter-based oligomers are substantially identical. Some kits for detecting the presence or abundance of two or more target nucleic acids contain two or more promoter-based oligomers each configured to selectively hybridize a cDNA containing the substantial complement their respective target nucleic acids, wherein each of the two or more promoter based oligomers contain a tag sequence between their 5' promoter regions and their 3' a b c regions and wherein each of the tag sequences in each of these two or more promoter-based oligomers are substantially identical and wherein the kit further contains an additional promoter based oligomer comprising a target hybridizing sequence that is also substantially identical to the tag sequence. Some kits contain at least one promoter-based oligomer that is a promoter primer. Some kits contain at least one promoter-based oligomer that is a promoter provider.

Some kits contain at least one detection probe oligomer for hybridizing to a target nucleic acid sequence. Some kits for detecting the presence or abundance of two or more target nucleic acids contain two or more detection probe oligomers each configured to selectively hybridize each of their respective target nucleic acids. Some kits contain at least one detection probe oligomer for hybridizing to a target nucleic acid sequence, wherein the detection probe oligomer is a linear probe. Some kits contain at least one detection probe oligomer for hybridizing to a target nucleic acid sequence, wherein the detection probe oligomer is a labeled linear probe. Some kits contain at least one detection probe oligomer for hybridizing to a target nucleic acid sequence, wherein the detection probe oligomer is a dual labeled linear probe. Some kits contain at least one detection probe oligomer for hybridizing to a target nucleic acid sequence, wherein the detection probe oligomer is a hairpin probe. Some kits contain at least one detection probe oligomer for hybridizing to a target nucleic acid sequence, wherein the detection probe oligomer is a labeled hairpin probe. Some kits contain at least one detection probe oligomer for hybridizing to a target nucleic acid sequence, wherein the detection probe oligomer is a dual labeled hairpin probe. Some kits contain at least one detection probe oligomer for hybridizing to a target nucleic acid sequence, wherein the detection probe oligomer is a molecular beacon. Some kits contain at least one detection probe oligomer for hybridizing to a target nucleic acid sequence, wherein the detection probe oligomer is a molecular torch. Some kits contain at least one detection probe oligomer comprising a target hybridizing region that is substantially complementary to all or a portion of a micro RNA. Some kits contain at least one detection probe oligomer comprising a target hybridizing region that is substantially complementary to a portion of a micro RNA, wherein the portion is 5, 6, 7, 8, 9, 10, 11, 12, 13, 14, 15, 16, 17, 18, 19, 20, 21, 22, 23, 24, 25, 26 or 27 contiguous nucleotides of the micro RNA. Some kits contain at least one detection probe oligomer comprising a target hybridizing region that is substantially complementary to a portion of a micro RNA, wherein the portion is 5, 6, 7, 8, 9, 10, 11, 12, 13, 14, 15, 16, 17, 18, 19, 20, 21, 22, 23, 24, 25, 26 or 27 contiguous nucleotides at the 3' end of the micro RNA. Some kits contain at least one detection probe oligomer comprising a target hybridizing region that is substantially complementary to a portion of a micro RNA, wherein the portion is 5, 6, 7, 8, 9, 10, 11, 12, 13, 14, 15, 16, 17, 18, 19, 20, 21, 22, 23, 24, 25, 26 or 27 contiguous nucleotides at the 5' end of the micro RNA. Some kits contain at least one detection probe oligomer comprising a target hybridizing region that is substantially complementary to all or a portion of miR-21. Some kits contain at least one detection probe oligomer comprising a target hybridizing region that is substantially complementary to all or a portion of miR-34b. Some kits contain at least one detection probe oligomer comprising a target hybridizing region that is substantially complementary to all or a portion of miR-182. Some kits contain at least one detection probe oligomer comprising a target hybridizing region that is substantially complementary to all or a portion of miR-221. Some kits contain at least one detection probe oligomer comprising a target hybridizing region that is substantially complementary to all or a portion of miR-222. Some kits contain at least one detection probe oligomer comprising a target hybridizing region that is substantially complementary to all or a portion of miR-802. Some kits contain at least one detection probe oligomer for hybridizing to an amplification product generated from a micro RNA template. Some kits contain at least one detection probe oligomer for hybridizing to an amplification product generated from a micro RNA template using an amplification oligomer described herein. Some kits contain at least one detection probe oligomer for hybridizing to an amplification product generated from a micro RNA template using an amplification oligomer selected from a first amplification oligomer as described herein, a promoter-based oligomer as described herein, a reverse primer oligomer as described herein or combinations thereof. Some kits contain at least one detection probe oligomer for hybridizing to an amplification product generated from a micro RNA template using a first amplification oligomer in a 5' Z.sub.n a' b' c' 3' format as described herein, wherein the detection probe oligomer comprises a target hybridizing sequence that is substantially complementary to a portion of the extension nucleic acid sequence. Some kits contain at least one detection probe oligomer for hybridizing to an amplification product generated from a micro RNA template using a first amplification oligomer in a 5' Z.sub.n a' b' c' 3' format as described herein, wherein the detection probe oligomer comprises a target hybridizing region that is substantially identical to all or a portion of the micro RNA template. Some kits contain at least one detection probe oligomer for hybridizing to an amplification product generated from a micro RNA template using a first amplification oligomer in a 5' Z.sub.n a' b' c' 3' format as described herein, wherein the detection probe oligomer comprises a target hybridizing region that is substantially complementary to a portion of the extension nucleic acid sequence and to all or a portion of the amplification product sequence that is itself complementary to the micro RNA template. Some kits contain at least one detection probe oligomer for hybridizing to an amplification product generated from a micro RNA template using a promoter-based oligomer as described herein, wherein the detection probe oligomer comprises a target hybridizing sequence that is substantially identical to all or a portion of the target hybridizing sequence of the promoter-based oligomer. Some kits contain at least one detection probe oligomer for hybridizing to an amplification product generated from a micro RNA template using a promoter-based oligomer containing a tag sequence as described herein, wherein the detection probe oligomer comprises a target hybridizing sequence that is substantially identical to all or a portion of the target hybridizing sequence of the promoter-based oligomer, all or a portion of the tag sequence or a combination thereof. Some kits contain at least one detection probe oligomer for hybridizing to an amplification product generated from a micro RNA template using a promoter-based oligomer as described herein, wherein the detection probe oligomer comprises a target hybridizing region that is substantially complementary to an RNA transcript amplification product.

Some kits contain chemical compounds used in performing the methods herein, such as enzymes, substrates, acids or bases to adjust pH of a mixture, salts, buffers, chelating agents, denaturants, sample preparation agents, sample storage or transport medium, cellular lysing agents, total RNA isolation components and reagents, partial generalized RNA isolation components and reagents, solid supports, and other inorganic or organic compounds. Kits may include any combination of the herein mentioned components and other components not mentioned herein. Components of the kits can be packaged in combination with each other, either as a mixture or in individual containers. It will be clear to skilled artisans that the invention includes many different kit configurations.

The invention includes methods for detecting the presence or abundance of small RNA target nucleic acids described herein. The methods provide highly sensitive and selective detection of small RNA target nucleic acids from a sample. The methods provide highly sensitive and highly selective detection of biomarkers for diagnosing a condition, making a prognosis about a condition, monitoring a therapy for a condition or determining a treatment for a condition. The methods provide highly sensitive and highly selective detection of micro RNA target nucleic acids for diagnosing a condition, making a prognosis about a condition, monitoring a therapy for a condition or determining a treatment for a conditions. The methods provide highly sensitive and highly selective detection of miR-21, miR-34b, miR-182, miR-221, miR-222, miR802 or combinations thereof for diagnosing a condition, making a prognosis about a condition, monitoring a therapy for a condition or determining a treatment for a conditions. The methods provide highly sensitive and highly selective detection of biomarkers in a sample suspected to indicate a cancer, for diagnosing a cancer, making a prognosis about a cancer, monitoring a cancer therapy or determining a cancer treatment. The methods provide highly sensitive and highly selective detection of biomarkers in a sample useful for identifying prostate cancer, for diagnosing prostate cancer, making a prognosis about prostate cancer cancer, monitoring prostate cancer therapy or determining a prostate cancer treatment. The methods provide highly sensitive and highly selective detection of biomarkers present in a sample for discriminating normal tissue and/or indolent tumors from aggressive or metastatic disease. The methods provide highly sensitive and highly selective detection of biomarkers present in a sample for discriminating normal prostate tissue and/or indolent prostate cancer tumors from aggressive or metastatic prostate cancer. The methods provide highly sensitive and highly selective detection of miR-21, miR-221, miR-222 or combinations thereof present in a sample for discriminating normal prostate tissue and/or indolent prostate cancer tumors from aggressive or metastatic prostate cancer. The methods provide highly sensitive and highly selective detection of biomarkers from a plurality of different sample types for identifying sample types that are useful for diagnosing a condition, making a prognosis about a condition, monitoring a therapy for a condition or determining a treatment for a condition. The methods provide highly sensitive and highly selective detection of micro RNA target nucleic acids from a plurality of different sample types for identifying sample types that are useful for diagnosing a condition, making a prognosis about a condition, monitoring a therapy for a condition or determining a treatment for a conditions. The methods provide highly sensitive and highly selective detection of miR-21, miR-34b, miR-182, miR-221, miR-222, miR802 or combinations thereof from a plurality of different sample types for identifying sample types that are useful for diagnosing a condition, making a prognosis about a condition, monitoring a therapy for a condition or determining a treatment for a conditions. The methods provide highly sensitive and highly selective detection of biomarkers from a plurality of different sample types for identifying the presence, abundance and/or abundance of one or more biomarkers in a sample type, thereby generating a profile for the sample type that can be used for diagnosing a condition, making a prognosis about a condition, monitoring a therapy for a condition or determining a treatment for a condition. Methods herein can be uniplex reactions. Methods herein can be multiplex reactions. A plurality of uniplex reactions can be run in parallel. Methods herein can include internal controls for reaction quality and/or for quantitation. Methods herein can be uniplex reactions for the detection of one of miR-21, miR-34b, miR-182, miR-221, miR-222 or miR-802, and may optionally include an internal control. Methods herein can be multiplex reactions for the detection of one or more of miR- 21, miR-34b, miR-182, miR-221, miR-222, miR-802, and may optionally include an internal control.

Some methods herein include one or more target capture oligomers for hybridizing to a target nucleic acid. Some methods for detecting the presence or abundance of two or more target nucleic acids can use two or more target capture oligomers each configured to selectively hybridize each of their respective target nucleic acids. Some target capture oligomers are configured in a 5' $X_n$ a' b' c' $Y_n$ 3' format, wherein a'b'c' is substantially complementary to all or a portion of a micro RNA and wherein X and Y are substantially homopolymeric nucleic acid sequences that are complementary one to the other. Some target capture oligomers are configured in a 5' $X_n$ a' b' c' $Y_n$ 3' format, wherein a'b'c' is substantially complementary to all or a portion of miR-21 and wherein X and Y are substantially homopolymeric nucleic acid sequences that are complementary one to the other. Some target capture oligomers are configured in a 5' $X_n$ a' b' c' $Y_n$ 3' format, wherein a'b'c' is substantially complementary to all or a portion of miR-34b and wherein X and Y are substantially homopolymeric nucleic acid sequences that are complementary one to the other. Some target capture oligomers are configured in a 5' $X_n$ a' b' c' $Y_n$ 3' format, wherein a'b'c' is substantially complementary to all or a portion of miR-182 and wherein X and Y are substantially homopolymeric nucleic acid sequences that are complementary one to the other. Some target capture oligomers are configured in a 5' $X_n$ a' b' c' $Y_n$ 3' format, wherein a'b'c' is substantially complementary to all or a portion of miR-221 and wherein X and Y are substantially homopolymeric nucleic acid sequences that are complementary one to the other. Some target capture oligomers are configured in a 5' $X_n$ a' b' c' $Y_n$ 3' format, wherein a'b'c' is substantially complementary to all or a portion of miR-222 and wherein X and Y are substantially homopolymeric nucleic acid sequences that are complementary one to the other. Some target capture oligomers are configured in a 5' $X_n$ a' b' c' $Y_n$ 3' format, wherein a'b'c' is substantially complementary to all or a portion of miR-802 and wherein X and Y are substantially homopolymeric nucleic acid sequences that are complementary one to the other. Some methods herein include capture of a target nucleic acid using a hairpin target capture probe as described herein to isolate the target nucleic acid away from cellular debris, total RNA or size fractionated population of general RNA. The isolated target nucleic acid is optionally subjected to a wash step. The isolated target nucleic acid is released from the target capture probe and an amplification reaction is performed using at least one amplification oligomer, wherein the target capture oligomer and an amplification oligomer comprise target hybridizing sequences that compete for binding a target sequence of the target nucleic acid. Preferably, a set of conditions are applied to the reaction mixture to form the target capture oligomer to a hairpin configuration and then the amplification reaction is performed. Some methods herein include generating an amplification reaction mixture that comprises at least one target nucleic acid, at least one amplification oligomer and at least one target capture probe in a hairpin configuration.

Some methods herein include one or more first amplification oligomers for hybridizing to a target nucleic acid. Some methods for detecting the presence or abundance of two or more target nucleic acids can use two or more first amplification oligomers each configured to selectively hybridize each of their respective target nucleic acids. Some first amplification oligomers are configured in a 5' $Z_n$ a' b' c' 3' format, wherein a' b' c' is substantially complementary to all or a portion of a micro RNA sequence and wherein Z is an extension nucleic acid sequence. The a' b' c' region of the first amplification oligomer can be substantially complementary to is the entire micro RNA sequence. The a'b'c' region of the first amplification oligomer can be substantially complementary to a portion of a micro RNA, wherein the portion is up to 20 contiguous nucleotides of the micro RNA sequence. The a'b'c' region of the first amplification oligomer can be substantially complementary to a portion of a micro RNA, wherein the portion is up to 20 contiguous nucleotides of the micro RNA sequence. The a'b'c' region of the first amplification oligomer can be substantially complementary to a portion of a micro RNA, wherein the portion is up to 15 contiguous nucleotides of the micro RNA sequence. The a'b'c' region of the first amplification oligomer can be substantially complementary to a portion of a micro RNA, wherein the portion is up to 10 contiguous nucleotides of the micro RNA sequence. The a'b'c' region of the first amplification oligomer can be substantially complementary to a portion of a micro RNA, wherein the portion is 5, 6, 7, 8, 9, 10, 11, 12, 13, 14, 15, 16, 17, 18, 19, 20, 21, 22, 23, 24, 25, 26 or 27 contiguous nucleotides of the micro RNA sequence. The a'b'c' region of the first amplification oligomer can be substantially complementary to a portion of a micro RNA, wherein the portion is the 5, 6, 7, 8, 9, 10, 11, 12, 13, 14, 15, 16, 17, 18, 19, 20, 21, 22, 23, 24, 25, 26 or 27 contiguous nucleotides at the 3' end of the micro RNA sequence. Preferably, the 5'$Z_n$ region of the first amplification primer is configured to form a hairpin structure. The 5'$Z_n$ region of the first amplifications primer can be configured to contain a target sequence or complement thereof for hybridizing a reverse primer oligomer or a detection probe oligomer or both. Some first amplification oligomers are configured in a 5' $Z_n$ a' b' c' 3' format, wherein a'b'c' is substantially complementary to all or a portion of a miR-21 sequence and wherein Z is an extension nucleic acid sequence. Some first amplification oligomers are configured in a 5' $Z_n$ a' b' c' 3' format, wherein a'b'c' is substantially complementary to all or a portion of a miR-34b sequence and wherein Z is an extension nucleic acid sequence. Some first amplification oligomers are configured in a 5' $Z_n$ a' b' c' 3' format, wherein a'b'c' is substantially complementary to all or a portion of a miR-182 sequence and wherein Z is an extension nucleic acid sequence. Some first amplification oligomers are configured in a 5' $Z_n$ a' b' c' 3' format, wherein a'b'c' is substantially complementary to all or a portion of a miR-221 sequence and wherein Z is an extension nucleic acid sequence. Some first amplification oligomers are configured in a 5' $Z_n$ a' b' c' 3' format, wherein a'b'c' is substantially complementary to all or a portion of a miR-222 sequence and wherein Z is an extension nucleic acid sequence. Some first amplification oligomers are configured in a 5' $Z_n$ a' b' c' 3' format, wherein a'b'c' is substantially complementary to all or a portion of a miR-802 sequence and wherein Z is an extension nucleic acid sequence. Some methods herein include generating a cDNA strand from a target nucleic acid that is a small RNA, preferably a micro RNA, more preferably one of miR-21, miR-34b, miR-182, miR-221, miR-222 or miR-802. Some methods herein include generating a cDNA strand from a target nucleic acid that is a small RNA, preferably a micro RNA, more preferably one of miR-21, miR-34b, miR-182, miR-221, miR-222 or miR-802, wherein the cDNA strand comprises a complement of an extension nucleic acid sequence from an extender primer as described herein. Some methods include generating a reaction mixture that comprises at least one first amplification oligomer and at least one promoter based oligomer, wherein the first amplification oligomer and the promoter-based oligomer each comprise target hybridizing sequence that target overlapping sequences on a small RNA target nucleic acid and complement thereof, preferably a micro RNA target nucleic acid, more preferably one of miR-21, miR-34b, miR-182, miR-221, miR222 or miR-802. Some methods include generating a reaction mixture that comprises at least one first amplification oligomer and at least one promoter based oligomer, wherein the first amplification oligomer and the promoter-based oligomer each comprise target hybridizing sequence that target non-overlapping sequences on a small RNA target nucleic acid and complement thereof, preferably a micro RNA target nucleic acid, more preferably one of miR-21, miR-34b, miR-182, miR-221, miR222 or miR-802. Some methods include performing an amplification reaction in a reaction mixture that comprises a target capture oligomer, a first amplification oligomer, a promoter-based oligomer and a target nucleic acid wherein the first amplification oligomer and the target capture oligomer comprise target hybridizing sequences that compete for binding a target sequence of the target nucleic acid, and wherein the target capture oligomer and the promoter-based oligomer comprise target hybridizing sequences that are at least partially substantially complementary one to the other. Some methods include performing an amplification reaction in a reaction mixture that comprises a target capture oligomer, a first amplification oligomer, a promoter-based oligomer and a target nucleic acid wherein the first amplification oligomer and the target capture oligomer comprise target hybridizing sequences that compete for binding a target sequence of the target nucleic acid, and wherein the target capture oligomer and the promoter-based oligomer comprise target hybridizing sequences that are at least partially substantially complementary one to the other, and wherein the target nucleic acid in a hairpin form.

Some methods herein include at least one promoter-based oligomer for hybridizing to a cDNA containing the substantial complement of a target nucleic acid sequence. Some methods for detecting the presence or abundance of two or more target nucleic acids can use two or more promoter-based oligomers each configured to selectively hybridize a cDNA containing the substantial complement their respective target nucleic acid. Some promoter-based oligomers are configured in a 5' promoter a b c 3' format, wherein a b c is substantially identical to all or a portion of a micro RNA sequence and wherein the promoter is an RNA polymerase promoter sequence. The a b c region of the promoter-based oligomer can be substantially identical to the entire micro RNA sequence. The a b c region of the promoter-based oligomer can be substantially identical to a portion of a micro RNA, wherein the portion is up to 20 contiguous nucleotides of the micro RNA sequence. The a b c region of the promoter-based oligomer can be substantially identical to a portion of a micro RNA, wherein the portion is up to 20 contiguous nucleotides of the micro RNA sequence. The a b c region of the promoter-based oligomer can be substantially identical to a portion of a micro RNA, wherein the portion is up to 15 contiguous nucleotides of the micro RNA sequence. The a b c region of the promoter-based oligomer can be substantially identical to a portion of a micro RNA, wherein the portion is up to 10 contiguous nucleotides of the micro RNA sequence. The a b c region of the promoter-based oligomer can be substantially identical to a portion of a micro RNA, wherein the portion is 5, 6, 7, 8, 9, 10, 11, 12, 13, 14, 15, 16, 17, 18, 19, 20, 21, 22, 23, 24, 25, 26 or 27 contiguous nucleotides of the micro RNA sequence. The a b c region of the promoter-based oligomer can be substantially identical to a portion of a micro RNA, wherein the portion is the 5, 6, 7, 8, 9, 10, 11, 12, 13, 14, 15, 16, 17, 18, 19, 20, 21, 22, 23, 24, 25, 26 or 27 contiguous nucleotides at the 5' end of the micro RNA sequence. Some promoter-based oligomers are configured in a 5' promoter a b c 3' format, wherein a b c is substantially identical to all or a portion of a miR-21 sequence. Some promoter-based oligomers are configured in a 5' promoter a b c 3' format, wherein a b c is substantially identical to all or a portion of a miR-34b sequence. Some promoter-based oligomers are configured in a 5' promoter a b c 3' format, wherein a b c is substantially identical to all or a portion of a miR-182 sequence. Some promoter-based oligomers are configured in a 5' promoter a b c 3' format, wherein a b c is substantially identical to all or a portion of a miR-221 sequence. Some promoter-based oligomers are configured in a 5' promoter a b c 3' format, wherein a b c is substantially identical to all or a portion of a miR-222 sequence. Some promoter-based oligomers are configured in a 5' promoter a b c 3' format, wherein a b c is substantially identical to all or a portion of a miR-802 sequence. Some promoter-based oligomers can optionally comprise a tag sequence between the 5' promoter region and the 3' a b c region. In some methods for amplification using a universal amplification oligomer, a first promoter-based oligomer comprises a tag sequence between the 5' promoter region and the 3' a b c region and a second promoter-based oligomer is configured to hybridize to the complement of that tag sequence. In some methods for detecting the presence or abundance of two or more target nucleic acids, the composition includes two or more promoter-based oligomers each configured to selectively hybridize a cDNA containing the substantial complement their respective target nucleic acids, wherein each of the two or more promoter based oligomers comprise a tag sequence between their 5' promoter regions and their 3' a b c regions. In some methods for detecting the presence or abundance of two or more target nucleic acids, the composition includes two or more promoter-based oligomers each configured to selectively hybridize a cDNA containing the substantial complement their respective target nucleic acids, wherein each of the two or more promoter based oligomers comprise a tag sequence between their 5' promoter regions and their 3' a b c regions and wherein each of the tag sequences in each of these two or more promoter-based oligomers are substantially identical. In some methods for detecting the presence or abundance of two or more target nucleic acids, the composition includes two or more promoter-based oligomers each configured to selectively hybridize a cDNA containing the substantial complement of their respective target nucleic acids, wherein each of the two or more promoter based oligomers comprise a tag sequence between their 5' promoter regions and their 3' a b c regions and wherein each of the tag sequences in each of these two or more promoter-based oligomers are substantially identical and wherein the composition further includes an additional promoter based oligomer comprising a target hybridizing sequence that is also substantially identical to the tag sequences. Some compositions include at least one promoter-based oligomer that is a promoter primer. Some compositions include at least one promoter-based oligomer that is a promoter provider. Some methods herein include hybridizing a promoter-based oligomer to a nucleic acid sequence that is substantially complementary to all or a portion of a target nucleic acid and providing conditions for generating an RNA amplification product. Some methods herein include hybridizing a promoter-based oligomer to a nucleic acid sequence that is substantially complementary to all or a portion of a target nucleic acid in the presence of a target capture oligomer comprising a target hybridizing sequence that is substantially complementary to a target nucleic acid and providing conditions for generating an RNA amplification product from the promoter-based amplification product. Some methods herein include hybridizing a promoter-based oligomer to a nucleic acid sequence that is substantially complementary to all or a portion of a target nucleic acid in the presence of a target capture oligomer comprising a target hybridizing sequence that is substantially complementary to a target nucleic acid, wherein the target capture oligomer is in a hairpin form, and providing conditions for generating an RNA amplification product from the promoter-based amplification product. Some methods herein include hybridizing a promoter-based oligomer to a nucleic acid sequence that is substantially complementary to all or a portion of a target nucleic acid in the presence of a target capture oligomer comprising a target hybridizing sequence that is substantially complementary to at least a portion of the promoter-based oligomer target hybridizing sequence, and providing conditions for generating an RNA amplification product from the promoter-based amplification product. Some methods herein include hybridizing a promoter-based oligomer to a nucleic acid sequence that is substantially complementary to all or a portion of a target nucleic acid in the presence of a target capture oligomer comprising a target hybridizing sequence that is substantially complementary to at least a portion of the promoter-based oligomer target hybridizing sequence, wherein the target capture oligomer is in a hairpin form, and providing conditions for generating an RNA amplification product from the promoter-based amplification product. Some methods herein include hybridizing a promoter-based oligomer to a nucleic acid sequence that is substantially complementary to all or a portion of a miR-21, miR-34b, miR-182, miR-221, miR-222 or miR-802 target nucleic acid in the presence of a target capture oligomer comprising a target hybridizing sequence that is substantially complementary to at least a portion of the promoter-based oligomer target hybridizing sequence, and providing conditions for generating an RNA amplification product from the promoter-based amplification product. Some methods herein include hybridizing a promoter-based oligomer to a nucleic acid sequence that is substantially complementary to all or a portion of a miR-21, miR-34b, miR-182, miR-221, miR-222 or miR-802 target nucleic acid in the presence of a target capture oligomer comprising a target hybridizing sequence that is substantially complementary to at least a portion of the promoter-based oligomer target hybridizing sequence, wherein the target capture oligomer is in a hairpin form, and providing conditions for generating an RNA amplification product from the promoter-based amplification product. Some methods herein include generating an amplification reaction mixture that comprises at least one promoter-based oligomer and at least one target capture oligomer, wherein the promoter-based oligomer comprises a target hybridizing sequence that is substantially identical to all or a portion of a miR-21, miR-34b, miR-182, miR-221, miR-222 or miR-802 target nucleic acid sequence, and wherein the target capture oligomer comprises a target hybridizing region that is substantially complementary to all or a portion of a miR-21, miR-34b, miR-182, miR-221, miR-222 or miR-802 target nucleic acid sequence. Some methods herein include generating an amplification reaction mixture that comprises at least one promoter-based oligomer, at least one target capture oligomer and at least one first amplification oligomer, wherein the promoter-based oligomer comprises a target hybridizing sequence that is substantially identical to all or a portion of a miR-21, miR-34b, miR-182, miR-221, miR-222 or miR-802 target nucleic acid sequence, wherein the target capture oligomer comprises a target hybridizing region that is substantially complementary to all or a portion of a miR-21, miR-34b, miR-182, miR-221, miR-222 or miR-802 target nucleic acid sequence, and wherein the first amplification oligomer comprises a target hybridizing region that is substantially complementary to all or a portion of a miR-21, miR-34b, miR-182, miR-221, miR-222 or miR-802 target nucleic acid sequence. Some methods herein include performing an amplification reaction in an amplification reaction mixture comprising amplification oligomers and at least one target capture oligomer wherein the target capture oligomers are formed to a hairpin formation under a set of conditions and wherein the amplification reaction proceeds at a set of conditions configured to maintain the target capture oligomer as a hairpin.

Some methods include at least one detection probe oligomer for hybridizing to a target nucleic acid sequence. Some methods for detecting the presence or abundance of two or more target nucleic acids can use two or more detection probe oligomers each configured to selectively hybridize each of their respective target nucleic acids. Some detection probe oligomers for hybridizing to a target nucleic acid sequence are linear probes. Some detection probe oligomers are labeled linear probes. Some detection probe oligomers are dual labeled linear probes. Some detection probe oligomers are hairpin probes. Some detection probe oligomers are labeled hairpin probe. Some detection probe oligomers are dual labeled hairpin probe. Some detection probe oligomers are molecular beacons. Some detection probe oligomers are molecular torches. Some detection probe oligomers comprise a target hybridizing region that is substantially complementary to all or a portion of a micro RNA. Some detection probe oligomers comprise a target hybridizing region that is substantially complementary to a portion of a micro RNA, wherein the portion is 5, 6, 7, 8, 9, 10, 11, 12, 13, 14, 15, 16, 17, 18, 19, 20, 21, 22, 23, 24, 25, 26 or 27 contiguous nucleotides of the micro RNA. Some detection probe oligomers comprise a target hybridizing region that is substantially complementary to a portion of a micro RNA, wherein the portion is 5, 6, 7, 8, 9, 10, 11, 12, 13, 14, 15, 16, 17, 18, 19, 20, 21, 22, 23, 24, 25, 26 or 27 contiguous nucleotides at the 3' end of the micro RNA. Some detection probe oligomers comprise a target hybridizing region that is substantially complementary to a portion of a micro RNA, wherein the portion is 5, 6, 7, 8, 9, 10, 11, 12, 13, 14, 15, 16, 17, 18, 19, 20, 21, 22, 23, 24, 25, 26 or 27 contiguous nucleotides at the 5' end of the micro RNA. Some detection probe oligomers comprise a target hybridizing region that is substantially complementary to all or a portion of miR-21. Some detection probe oligomers comprise a target hybridizing region that is substantially complementary to all or a portion of miR-34b. Some detection probe oligomers comprise a target hybridizing region that is substantially complementary to all or a portion of miR-182. Some detection probe oligomers comprise a target hybridizing region that is substantially complementary to all or a portion of miR-221. Some detection probe oligomers comprise a target hybridizing region that is substantially complementary to all or a portion of miR-222. Some detection probe oligomers comprise a target hybridizing region that is substantially complementary to all or a portion of miR-802. Some methods herein include at least one detection probe oligomer for hybridizing to an amplification product. Some methods herein for detecting the presence or abundance of two or more target nucleic acids can use two or more detection probe oligomers each configured to hybridize to an amplification product generated from the two or more target nucleic acids. Some methods herein for detecting the presence or abundance of two or more target nucleic acids can use two or more detection probe oligomers each configured to selectively hybridize to an amplification product generated from the two or more target nucleic acids. Some detection probe oligomers are configured to hybridize to an amplification product generated from a micro RNA template. Some detection probe oligomers are configured to hybridize to an amplification product generated from a micro RNA template using an amplification oligomer described herein. Some detection probe oligomers are configured to hybridize to an amplification product generated from a micro RNA template using an amplification oligomer selected from a first amplification oligomer as described herein, a promoter-based oligomer as described herein, a reverse primer oligomer as described herein or combinations thereof. Some detection probe oligomers are configured to hybridize to an amplification product generated from a micro RNA template using a first amplification oligomer in a 5' $Z_n$ a' b' c' 3' format as described herein, wherein the detection probe oligomer comprises a target hybridizing sequence that is substantially complementary to a portion of the extension nucleic acid sequence. Some detection probe oligomers are configured to hybridize to an amplification product generated from a micro RNA template using a first amplification oligomer in a 5' $Z_n$ a' b' c' 3' format as described herein, wherein the detection probe oligomer comprises a target hybridizing region that is substantially identical to all or a portion of the micro RNA template. Some detection probe oligomers are configured to hybridize to an amplification product generated from a micro RNA template using a first amplification oligomer in a 5' $Z_n$ a' b' c' 3' format as described herein, wherein the detection probe oligomer comprises a target hybridizing region that is substantially complementary to a portion of the extension nucleic acid sequence and to all or a portion of the amplification product sequence that is itself complementary to the micro RNA template. Some detection probe oligomers are configured to hybridize to an amplification product generated from a micro RNA template using a promoter-based oligomer as described herein, wherein the detection probe oligomer comprises a target hybridizing sequence that is substantially identical to all or a portion of the target hybridizing sequence of the promoter-based oligomer. Some detection probe oligomers are configured to hybridize to an amplification product generated from a micro RNA template using a promoter-based oligomer containing a tag sequence as described herein, wherein the detection probe oligomer comprises a target hybridizing sequence that is substantially identical to all or a portion of the target hybridizing sequence of the promoter-based oligomer, all or a portion of the tag sequence or a combination thereof. Some detection probe oligomers are configured to hybridize to an amplification product generated from a micro RNA template using a promoter-based oligomer as described herein, wherein the detection probe oligomer comprises a target hybridizing region that is substantially complementary to an RNA transcript amplification product.

Some methods herein use chemical compounds, such as enzymes, substrates, acids or bases to adjust pH of a mixture, salts, buffers, chelating agents, denaturants, sample preparation agents, sample storage or transport medium, cellular lysing agents, total RNA isolation components and reagents, partial generalized RNA isolation components and reagents, solid supports, and other inorganic or organic compounds. Methods may include using any combination of the herein mentioned components and other components not mentioned herein. Reaction mixtures useful in the methods can be provided as part of a commercially available product. Reaction mixtures useful in the methods can be provided premixed or partially premixed as part of a commercially available product. Reaction mixtures useful in the methods can be provided as separate components as part of a commercially available product.

Aspects and embodiments of the present invention are illustrated in the Examples that follow. Methods and reagents for nucleic acid synthesis, hybridization, and detection of labels were used substantially as described herein, although those skilled in the art will appreciate that other routine methods and standard reagents may also be used to achieve equivalent results. Oligonucleotides were synthesized using standard phosphoramidite chemistry (Caruthers et al., 1987, Methods in Enzymol., 154: 287), purified using routine chromatographic methods (e.g., HPLC), and typically stored in a solution of 10 mM Tris, 1 mM EDTA (pH 7.5), at room temperature to −80.deg.C. In the target capture steps illustrated in the examples, magnetic particles were used as the capture support which were separated from the soluble phase by applying a magnetic field to the outside of the assay container, although those skilled in the art will appreciate that other means of separation may be used. The supernatant containing soluble components was removed, and the hybridization complexes bound to the particles were washed (one to three times with a washing solution of sufficient ionic strength to maintain bonds binding the captured hybrid to the magnetic particles at the washing temperature, usually about 25.deg.C.). Washing generally is performed at room temperature by suspending the particles in the washing solution, separating particles, and removing the supernatant, and repeating those steps for each wash. For the detection step, the detection probe was incubated with the released target nucleic acid in an aqueous solution containing appropriate salts and buffers at a temperature below the Tm predicted for the detection probe sequence and its target sequence, usually for 30-60 min. When an AB-labeled detection probe was used, a homogeneous detection step was performed which uses differential hydrolysis of the AE label on unbound probes compared to AE-labeled probes bound to the target (described in detail in U.S. Pat. No. 5,283,174). For example, hydrolysis was performed by adding a selection reagent that promotes hydrolysis of the AE label on unbound probes (e.g., a basic solution), followed by adding a detection reagent that catalyzes chemiluminescence from AE attached to bound probes (e.g., $H_2O_2$), and the chemiluminescent signal (referred to as relative light units or RLU) was detected on a luminometer (e.g., LEADER® 450HC+, Gen-Probe Incorporated, San Diego, Calif.).

The following examples describe some preferred embodiments and reagents used in these assays. The skilled artisan will appreciate that other reagents and conditions may be substituted for those described herein to perform the method steps. For example, the reagents and conditions for producing and detecting a signal will be selected by the skilled artisan based on the chosen detection probe label. Those skilled in the art will understand that the invention methods may be performed using any chosen target nucleic acid sequence that can hybridize to a complementary sequence, i.e., the method is not dependent on any particular probe or target sequences. One of ordinary skill in the art will be able to select the target sequence and then design and synthesize the appropriate target hybridizing sequence of any of the capture probe forms described herein, and a target-specific detection probe by using routine methods. That is, specific assays will rely on selection of a target sequence and the appropriate target hybridizing sequences contained in the capture and detection probes that include the structural characteristics described herein, and such selection can be performed by one of ordinary skill in the art using standard procedures, followed by

Example 1

Detection of a Small Target Nucleic Acid Using Different Labeled Probes

To design detection probes, a target sequence of 23 nt was selected from a sequence common to genomic sequences of human Herpesvirus 5 (Cytomegalovirus) strains (Dunn et al., 2003, Proc. Natl. Acad. Sci. USA 100(24): 14223-14228; GenBank accession nos. AC146999, AC146851, and AY315197) and complementary to portions of fluorescent protein genes (GenBank accession nos. AY 303166, AY303167, and AY237157). Oligomers of 23 nt that were completely complementary to the target sequence were synthesized in vitro as a 2'-O-methyl oligoribonucleotides that had 52% GC content. Three versions of the probes were labeled with a linker at different positions (between bases 8 and 9, 12 and 13, and 13 and 14 of the 23-mer) and an AE label attached at the linker by using methods previously described in detail (U.S. Pat. Nos. 5,185,439, 5,283,174, and 5,656,744). The labeled probes (0.1 pmol per reaction) were individually hybridized at 60.deg.C. for 1 hr to a complementary synthetic ssRNA target sequence (10 pmol per reaction) in a 30 .micro.l reaction mixture containing 15 .micro.l of a hybridization reagent (190 mM succinate, 17% (w/v) lithium lauryl sulfate (LLS), 100 mM LiOH, 3 mM EDTA, and 3 mM EGTA, at pH 5.1). Then the hybridization mixture was diluted to 500 .micro.l with the hybridization reagent and 20 .micro.l aliquots were removed for performing the detection step by adding to each detection reaction mixture 80 .micro.l of the hybridization reagent, and then 200 .micro.l of a selection reagent (600 mM boric acid, 182.5 mM NaOH, 1% (v/v) octoxynol (TRITON® X-100), at pH 8.5), and hydrolysis was performed at 50.deg.C. for varying periods of time. Then, production and detection of the signal was performed by adding 200 .micro.l of a detection reagent (1 mM nitric acid and 32 mM $H_2O_2$) followed by adding 200 .micro.l of 1.5 M NaOH and the chemiluminescent signal (RLU) was measured (for 2 sec) by using a luminometer. The same detection reaction method was performed on aliquots that contained the individual probes without the ssRNA target to measure hydrolysis of the AE label on unbound probes. From these results, the time at which half of the detectable label for each probe composition was hydrolyzed (T1/2), when the complementary target strand was present or absent, was determined. The T1/2 for all three probes without the target (i.e., unbound probes) was between 0.69 and 1.05 min, whereas when the target was present (i.e., bound probes) the T1/2 was between 25.8 and 125 min, indicating that the detection probes bound to the target and produced a detectable signal in excess of the background signal in a homogeneous reaction mixture. When probes were hybridized with the target, they exhibited different T1/2 characteristics: the probe labeled between positions 12 and 13 had the shortest T1/2 (25.8 min), the probe labeled between positions 13 and 14 had the longest T1/2 (125 min), and the probe labeled between positions 8 and 9 was an intermediate T1/2 (69 min). These results show that all three probes were capable of binding to the complementary RNA target, that labels in unbound probes could be distinguished from labels in bound probes by differential hydrolysis characteristics, and that the labeling position on the oligomer affected the rate of label hydrolysis so that optimal probes for an assay may be selected and designed using routine testing.

Example 2

Sensitivity of Detection of Single-Stranded and Double-Stranded Targets

The sensitivity of target detection was determined by using the same target and detection probe sequences as in Example 1, but comparing detection of the RNA target when it was in ssRNA or dsRNA form. The ssRNA target oligomer and detection probe oligomer labeled with AE between positions 13 and 14 were used as in Example 1. In these assays, all reactions contained 0.1 pmol of the AE-labeled probe that was hybridized to the ssRNA target present in a range of 0 to 5 fmol per hybridization reaction (100 .micro.l hybridization mixtures incubated at 60.deg.C. for 1 hr). Following hybridization, the AE label on unbound probe was hydrolyzed by adding 200 .micro.l of the selection reagent and incubating at 50.deg.C. for 10 min, and then the chemiluminescent signal from bound probe was detected substantially as described in Example 1. Results shown in Table 1, columns 1 and 2, demonstrate that a linear detectable signal was measured over the range of target amounts tested. As little as 0.005 fmol of the ssRNA target in the reaction resulted in a detectable signal over the background signal obtained when no target nucleic acid was present in the assay. "Net RLU" data (column 2) was calculated by subtracting the background RLU (560 RLU when no target was present) from the detected RLU for each test sample.

In the tests performed using the dsRNA target, the target was made by synthesizing a complementary RNA strand to the ssRNA target oligomer described above and hybridizing the two complementary RNA strands together. The dsRNA target was tested substantially as described above by using the same probe as described above synthesized as a 2'-O-methyl oligoribonucleotide and labeled with AE between positions 13 and 14. This detection probe was complementary to one of the strands in the dsRNA target. Before hybridization with the AE-labeled probe, the dsRNA target was denatured by heating it in solution (10 mM Li-succinate and 0.01% LLS, pH5.0) at 90.deg.C. for 5-7 min, followed by quickly cooling on ice. In Test 1, 50 pmol of the target dsRNA was denatured and then diluted to make the different amounts of target used in each of the 100 .micro.l hybridization reactions. In Test 2, the appropriate amounts of the target dsRNA were distributed to separate tubes in 50 .micro.l aliquots, heat denatured as described above, and then 50 .micro.l of the hybridization reagent containing the labeled probe was added to each tube make the hybridization reaction mixtures. The hybridization and detection reactions were performed substantially as described above for the ssRNA target reactions and the results for the dsRNA target are shown in Table 1, columns 3 to 5. The background signal detected when no target was present (942 RLU in Test 1, 932 RLU in Test 2) was subtracted from the detected signal when the dsRNA target was present to obtain the "Net RLU" (column 4 for Test 1, and column 5 for Test 2). The Net RLU measurements showed that the assay produced a detectable signal that was a substantially linear response over the range of target amounts tested. A positive signal was detected when as little as 0.01 fmol (Test 1) to 0.05 fmol (Test 2) of the target RNA was present in the reaction indicating the sensitivity of the detection step.

TABLE 1

Signal Measured for Hybridization Reactions Containing Different Amounts of Target

| ssRNA (fmol) | Net RLU | dsRNA (fmol) | Net RLU - Test 1 | Net RLU - Test 2 |
|---|---|---|---|---|
| 0.005 | 391 | — | — | — |
| 0.01 | 719 | 0.01 | 122 | — |
| 0.02 | 1,289 | 0.02 | 151 | — |
| 0.05 | 3,376 | 0.05 | 625 | 2,796 |
| 0.07 | 4,648 | 0.07 | 567 | — |
| 0.1 | 7,157 | 0.1 | 1,066 | 5,561 |
| 0.25 | 16,922 | 0.25 | 2,079 | — |
| 0.5 | 29,729 | 0.5 | 4,443 | 27,142 |
| 1.0 | 64,929 | 1.0 | 7,974 | — |
| 5.0 | 287,821 | 5.0 | 54,077 | 240,787 |

Example 3

Capture and Detection of a Target RNA

In these assays, a capture probe capable of forming a hairpin structure under hybridization conditions was used to capture a target nucleic acid from a sample, followed by hybridization of the target nucleic acid with a labeled detection probe and detection of a signal from bound detection probe. The capture probes used in these experiments all contain structural features that allow formation of a hairpin structure: a 5' region homopolymeric sequence, a 3' region sequence that was fully or partially complementary to the 5' region sequence, and a target hybridizing sequence flanked by the 5' and 3' region sequences. The 5' and 3' region sequences form the "stem" portion of the hairpin structure, and the target hybridizing sequence forms the "loop" portion of the hairpin structure.

Three versions of a hairpin capture probe were synthesized and assayed using routine methods to determine the Tm of the stem of the hairpin capture probe. The complementary 5' and 3' region sequences of all three probes were synthesized with deoxyribonucleotide linkages. The target hybridizing sequence of each of the hairpin probes was the 23-nt target hybridizing sequence as in Example 1, synthesized in probes 1 and 2 with 2'-O-methyl linkages and in probe 3 with deoxyribonucleotide linkages. In probes 1 and 3, the 5' region was a (dT)12 sequence and the 3' region was a (dA)12 sequence; and in probe 2, the 5' region sequence was (dT)5A(dT)6 which is partially complementary to the 3' region sequence of (dA)12. Schematically, the resulting capture probe sequences were as follows: 5' TTTTTTTTTTTT—N.sub.23—AAAAAAAAAAAA 3' (probes 1 and 3; SEQ ID NO:1), and 5' TTTTTATTTTT—N. sub.23—AAAAAAAAAAAA 3' (probe 2; SEQ ID NO:2), in which $N_{23}$ represents the target hybridizing sequence. In will readily be appreciated that these linear sequences form partially double-stranded hairpin structures by intramolecular hybridization of the 5' region to the 3' region and the target hybridizing sequence (N.sub.23) becomes the loop portion of the hairpin structure. The Tm's for the double-stranded stem portions of these hairpin probes were in a range of about 46.deg.C. to about 57.deg.C. (46.3.deg.C. for probe 2, 55.7.deg.C. for probe 3, and 56.7.deg.C. for probe 1).

Capture using these hairpin capture probes and detection of the target was performed using the dsRNA target and AE-labeled probe described in Example 2, using target amounts ranging from 0.05 to 5 fmol per reaction. To provide a sample similar to a clinical sample, the dsRNA target present in 200 .micro.l of sample transport solution (110 mM LLS, 15 mM sodium phosphate monobasic, 15 mM sodium phosphate dibasic, 1 mM EDTA, 1 mM EGTA, pH 6.7) was mixed with 200 .micro.l of urine, to make a final sample volume of 400 .micro.l. This mixture was heated to denature the dsRNA target (at 90.deg.C. for 5 min, then cooled on ice), to provide a ssRNA target strand for hybridization with the capture probes. For each of the hairpin capture probes tested individually, the denatured RNA target sample was mixed with 100 .micro.l of a target capture reagent (250 mM HEPES, 310 mM LiOH, 1.88 M LiCl, 100 mM EDTA, pH 6.4) containing 0.3 pmol of the hairpin capture probe and 50 .micro.g of magnetic particles which were the capture support (1 micron Sera-Mag™ MG-CM particles, Seradyn, Inc. Indianapolis, Ind.), to which immobilized probe oligomers of dT.sub.14 were covalently attached. The mixture was incubated at 65.deg.C. for 60 min (a temperature above the Tm of each of the capture probes) and then at room temperature for 30 min to form capture hybrids attached to the particles. Then, the particles with the attached capture hybrids were separated magnetically from the liquid sample components that were removed. The particles with attached capture hybrids were washed twice at room temperature with 500 .micro.l of the sample transport solution and then the particles with attached capture hybrids were separated from the solution which was removed. The washed particles with the attached capture hybrids were mixed with 100 .micro.l of water and heated (90.deg.C. for 5 min) to release the nucleic acid components of the capture hybrids (target and capture probe oligomers released into solution and the immobilized probe remained covalently attached to the capture support particle). For detection of the target, the solution then was mixed with an AB-labeled detection probe, as described in Example 2, in 100 .micro.l of the hybridization reagent and the mixture was incubated under hybridization conditions (55.deg.C. for 60 min) to allow the detection probe to bind to the target strands. Under these conditions, the released capture probes may reform the partially double-stranded hairpin structure by intramolecular hybridization to minimize competitive inhibition caused by the capture probes competing with the detection probes for hybridization to the target strand. The detection probe and the target hybridizing sequence of the hairpin capture probes will not hybridize to each other because they are the same sense strands. Detection of the signal from bound detection probes was performed substantially as described in Example 1. Control reactions without target were treated identically and the background signal for all reactions was in the range of 535 to 715 RLU. The experimental results of these assays are shown in Table 2, column 2, as net RLU (detected RLU minus background RLU). For each assay, the ratio of the detected signal to background RLU is shown in Table 2, column 3.

TABLE 2

Assays Performed Using a Hairpin Capture Probe and Detection Probe

| Target Amount (fmol) | Net RLU | Signal/Background Ratio |
|---|---|---|
| 0.05 | 1,248 | 3 |
| 0.1 | 2,223 | 4.4 |
| 0.15 | 3,318 | 6.6 |
| 0.2 | 5,418 | 9 |
| 0.5 | 11,156 | 22 |
| 1.0 | 24,758 | 36 |
| 2.0 | 38,351 | 55 |
| 5.0 | 98,180 | 140 |

The results of these assays show that the combination of capture of a target nucleic acid by using a hairpin capture probe and detection by using a detection probe complementary to one strand of a dsRNA target effectively detected the target present in a sample for all of the amounts of target tested.

Example 4

Assays Comparing Different Forms of Capture Probes

These assays compared the relative efficiency of capture and detection of a target sequence, using methods similar to those described in Example 3, when the target capture step was performed by using a capture probe of either a hairpin structure or linear structure. Unless otherwise stated, the reagents used in these tests were the same as disclosed in Examples 1 to 3 above. All of the assays used test samples containing 1 fmol of the ssRNA target, as described in Example 2, in 200 .micro.l of urine mixed with 200 .micro.l of sample transport solution. For the target capture step, each 400 .micro.l test sample was mixed with 100 .micro.l of target capture reagent containing different amounts (0.1, 0.5, 1.0, 2.0, 5.0, 10 and 20 pmoles) of either a partially double-stranded hairpin capture probe as described in Example 3 (SEQ ID NO:1) or a linear single-stranded capture probe of the following structure: 5' X N.sub.23 TTTAAAAAAAAAAAA 3' (SEQ ID NO:3) that has substantially the same target hybridizing sequence (N.sub.23) as in the hairpin capture probe, but includes one additional 5' nucleotide (X). In both the hairpin and linear forms of the capture probes, the target hybridizing sequences were synthesized with 2'-O-methyl linkages. In the hairpin capture probe, the target hybridizing sequence was flanked by the complementary 5' poly-dT and 3' poly-dA regions, whereas in the linear form the target hybridizing sequence was covalently linked to a 3' (dT).sub.3(dA).sub.30 sequence. The reaction mixtures were incubated at 65.deg.C. for 60 min and then at room temperature for 30 min to allow formation of capture hybrids and attachment to the capture support via the immobilized probe. The supports with attached capture hybrids were separated from the liquid sample components by applying a magnetic field and washed twice (using 0.5 ml of sample transport solution each) substantially as described in Example 3. The final wash solution was removed and the capture supports with attached capture hybrids were mixed with 100 .micro.l of water per assay, incubated at 90.deg.C. for 5 min and rapidly cooled on ice to release the capture hybrids into the nucleic acid components before hybridization of the target strand with the detection probe. Then, each test sample was mixed with 0.1 pmole of the AE-labeled detection probe of Example 2 in 100 .micro.l of hybridization reagent and incubated at 55.deg.C. for 60 min to allow hybridization of the detection probe to the target strand. Detection of the chemiluminescent signal from detection probes bound to the target strands was performed substantially as described in Example 3 (add 200 .micro.l of selection reagent, incubate at 55.deg.C. for 10 min, mix with 200 .micro.l of detection reagent and measure chemiluminescence (for 5 sec) on a luminometer). The results are shown in Table 3, as net RLU in column 2 and 3, and the relative percentage of detection obtained when the capture step had been performed by using the linear or hairpin forms of the capture probes, in columns 4 and 5. The net RLU was calculated by subtracting the background RLU from the RLU detected in positive samples (background was 762 RLU for the hairpin probe tests and 749 RLU for the linear probe tests). The relative percentage of detection was calculated by setting the highest detected net RLU at 100% (results for 0.1 pmole of hairpin capture probe) and dividing the lesser net RLU detected in the other tests by the highest net RLU (21,778).

TABLE 3

Comparison of Hairpin and Linear Capture Probes

| Capture Probe (pmole) | Net RLU Hairpin Probe | Net RLU Linear Probe | % Detection Hairpin Probe | % Detection Linear Probe |
|---|---|---|---|---|
| 0.1 | 21,778 | 15,849 | 100 | 72.8 |
| 0.5 | 19,614 | 7,286 | 90.1 | 33.5 |
| 1.0 | 18,248 | 4,172 | 83.8 | 19.2 |
| 2.0 | 17,316 | 2,578 | 79.5 | 11.8 |
| 5.0 | 11,889 | 1,137 | 54.6 | 5.2 |
| 10 | 9,778 | 722 | 44.9 | 3.3 |
| 20 | 4,519 | 458 | 20.7 | 2.1 |

These results show that the assays performed by using a linear form and a hairpin form of the capture probes specific for the same target sequence resulted in a detectable signal for all of the assays performed. The relative percentage of detection was consistently higher when the capture probe was in the hairpin form compared to the linear form. The difference in relative percentage of detection ranged from about 10-fold more when the results obtained for the two forms were compared for the highest amounts of capture probes tested (20 pmoles per reaction), to about 2.7-fold when the results obtained for the two forms were compared for the lowest amount of capture probes tested (0.1 pmole per reaction). The differences between the assays that used the hairpin and linear capture probe forms may result from more competitive inhibition when the linear capture probe was used because the released linear form may compete with the detection probe for hybridization to the target sequence during the detection phase of the assay whereas the hairpin form under the same conditions may reform the hairpin structure to limit competition between the target hybridizing sequence of the capture probe and the detection probe for binding the target.

Example 5

Assays Using a Partially Double-Stranded Capture Probe

This example describes an embodiment that uses a completely or partially double-stranded capture probe. The capture probe of this embodiment is made up of two completely or partially complementary strands of which one strand includes a target hybridizing sequence that binds to a portion of the target nucleic acid. One version of the capture probe is made up of a first capture probe strand (SEQ ID NO:4) and a second capture probe strand (SEQ ID NO:5) that are synthesized and hybridized together to make a partially double-stranded capture probe bound by hybridization of at least their complementary 3' polyA and 5' polyT sequences: 5'TTTTTTTTTTTTTTAGAGGATGGGTTTTCTAGGGG 3' (SEQ ID NO:4), 3'AAAAAAAAAAAAAAATCTCTCTCTCTCTCTCTC 5' (SEQ ID NO:5). The oligomer of SEQ ID NO:4 contains a 5' poly-T region and a 3' sequence complementary to a sequence contained in a human B19 parvovirus genome (GenBank accession no. AY386330); and the oligomer of SEQ ID NO:5 contains a 5' poly-(TC) region and a 3' poly-A region. In another version, the capture probe is completely double stranded and made up of the first capture probe strand (SEQ ID NO:4) hybridized to its complementary strand (SEQ ID NO:6): 5'TTTTTTTTTTTTTTTAGAGGATGGGTTTTCTAGGGG 3' (SEQ ID NO:4), 3'AAAAAAAAAAAAAAATCTCCTACCCAAAAGATCCCC 5' (SEQ ID NO:6).

In separate assays, about 3.5 pmole of each version of the capture probes is mixed with a 0.5 ml plasma sample containing parvovirus B19 genomic DNA (denatured and, optionally, sheared or enzymatically digested into fragments of about 100 to 1000 nt long) and an equal volume of target capture reagent containing capture support particles with attached poly(A) oligomers as the immobilized probe. That is, the immobilized poly(A) oligomers are complementary to the 5' poly-dT portion of the capture probe oligomer of SEQ ID NO:4. The mixture is incubated (60-65.deg.C., 20-60 min) to allow the capture probes to dissociate into the component oligomers (SEQ ID NO:4 and SEQ ID NO:5, or SEQ ID NO:4 and SEQ ID NO:6), to allow the target-specific portion of SEQ ID NO:4 to hybridize to the complementary sequence in the parvovirus B19 target DNA. Then, the mixture is incubated at a lower temperature (25-30.deg.C., 14-30 min) to allow the complementary homopolymeric sequences of the capture probe and the immobilized probe to hybridize, thereby attaching the target B19 DNA to the magnetic particles in a capture hybrid that includes the capture probe strands of SEQ ID NO:5 hybridized to the complementary sequence in the parvovirus B19 DNA. Particles with the attached capture hybrids are separated from the sample components by applying a magnetic force to the outside of the container and the liquid sample components, including unhybridized capture probe strands, are removed. A washing step is used in which the particles with the attached capture hybrids are suspended in an aqueous solution of sufficient ionic strength the maintain the capture hybrid attached to the capture support, then the particles are separated from the aqueous solution using magnetic force, and the washing solution with any unbound capture probe oligomers and other sample components is removed. For detection of the captured B19 DNA, the particles with the attached capture hybrids are mixed with a hybridization reagent containing detection probe oligomers of SEQ ID NO:7 (0.1-0.5 pmoles per reaction) labeled with a fluorescent label (e.g., fluorescein) and the detection probes are hybridized to a complementary sequence in the captured B19 DNA by incubating the mixture below the Tm of the detection probe but at a temperature above the melting temperature of the polA-polyT duplex, to release the B19 target nucleic acid into the solution phase (e.g., 55.deg.C. for 20-60 min). The mixture is then incubated at a lower temperature (e.g., 25-30.deg.C. for 10-30 min) to allow hybridization complexes made up of the B19 target DNA, detection probe and the poly-dT containing capture probe strand to attached to the poly (A) immobilized probes on the particles. The particles with attached complexes that contain the hybridized detection probes are separated from the solution phase as described above and the solution phase containing unbound detection probes is discarded. The particles with attached complexes are optionally washed, substantially as described above, under conditions that maintain the hybridization complexes on the particles to remove remaining unbound detection probes. Finally, the particles are mixed with a volume of liquid (e.g., 0.5 ml water) and the fluorescence of the mixture is measured using standard fluorometric procedures. A negative control sample, i.e. plasma containing no B19 particles or DNA, is treated identically as described above and the fluorescence that is measured from the negative control sample indicates background signal for the assay. For both the partially and completely double-stranded versions of the capture probe, these assays produce a detectable positive signal for test samples that contain parvovirus B19 nucleic acid that is significantly greater than the background signal that negative control samples produce. Positive signals indicate the presence of the parvovirus B19 target nucleic acid in the samples.

Example 6

Specific Capture, Amplification and Detection of miRNA Biomarkers

Materials and Methods used in the following examples. Cell lines and xenografts: LNCaP, DU145, PC-3 and VCaP prostate cancer lines were obtained from the American Type Culture Collection (Manassas, Va.). LNCaP and DU145 cell lines were cultured in RPMI Medium 1640 Custom (Invitrogen, Carlsbad, Calif.) containing 10% FBS. The PC-3 cell line was cultured in MEM with Earle's salts (Invitrogen) supplemented with 10% FBS, 2 mM L-glutamine, and 0.9 mM sodium pyruvate. VCaP cells were cultured in DMEM containing 10% FBS. Freshly frozen samples of 21 human prostate cancer severe combined immunodeficient xenografts (LuCaPs 23.12, 23.1, 23.1AI, 35, 35V, 49, 70, 77, 78, 81, 86.2, 92, 93, 96, 96AI, 105, 115, 141, 145.1, 145.2, 153) were prepared using standard methods. Characterization of several of these xenografts has been reported previously (Laitinen, Genes Chromosomes Cancer 2002, 35:66-73; Saramaki, Int J Cancer 2006, 119:1322-1329; Porkka, Cancer Res 2007, 67:6130-6135). Normal prostate tissue samples: Five adjacent-normal prostate tissues, pathologically determined to be 100% normal (OCT-embedded), were purchased from Cytomyx Inc. (Lexington, Mass.). These samples were shipped to Asuragen Services (Austin, Tex.) for subsequent RNA extraction and microRNA profiling.

RNA samples: Total RNA was extracted from cell lines using the Ambion mirVana miRNA isolation kit (Applied Biosystems Inc., Foster City, Calif.) and frozen sections of xenograft tissue using Trizol reagent (Invitrogen) according to the manufacturer's instructions. Synthetic mature miRNAs were purchased from Integrated DNA Technologies (Coralville, Iowa). The human pre-miR-802 sequence was obtained from the miRBase (Griffiths-Jones, Nucleic Acids Res 2006, 34:D140-4) of the Sanger Institute and a synthetic hairpin precursor was synthesized using PCR amplification of the 94 nt pre-miR-802 sequence from LNCaP genomic DNA cloned into pBluescript II SK (+) and expressed as an in vitro transcript.

Real-time quantitative PCR: cDNA was prepared from synthetic mature miRNAs or total RNA using specific TaqMan Assays-on-Demand reverse transcription primers and TaqMan miRNA Reverse Transcription Kit (Applied Biosystems Inc.). Absolute copy number of mature miRNAs was determined by qRT-PCR using TaqMan Assays-on-Demand primer and probe sets along with TaqMan Universal PCR master mix (Applied Biosystems Inc.) for cDNA amplification. Amplification and analysis were performed on the ABI 7000 sequence detection system. Copies per cell were determined from total nanograms of RNA using an estimated 15 picograms of total RNA per cell as described (Chen, Nucleic Acids Res 2005, 33:e179).

Real-time transcription-mediated amplification: All buffer and enzyme reagents used in the real-time TMA assays were APTIMA® reagents from Gen-Probe Incorporated (San Diego, Calif.). All reactions were run in triplicate. Amplification reactions were prepared in 96-well microtiter plates containing specifically designed T7-provider (U.S. Pat. No. 7,374,885) and 3'-extender oligonucleotides together with a common reverse primer and molecular beacon. The plates were transferred to an Eppendorf Thermomixer R™ instrument and incubated at 42.deg.C. for 5 minutes. Next, APTIMA enzyme reagent was rapidly pipetted into each well and a sealing card was applied to the plate. After a brief mixing step (1 minute at 42.deg.C.), the plate was transferred to an MJ Chromo4 instrument (Bio-Rad, Hercules, Calif.) that had been pre-heated to 42.deg.C. Fluorescence readings were taken every 20 seconds at 42.deg.C. for 60 minutes. Emergence times were compared against calibration standards to derive miRNA copy numbers. The T7 provider oligonucleotides used in these examples each contained a 3'-(reverse polarity)-dC nucleotide (5'-5'-phosphdiester linkage) to block 3'-extension (U.S. Pat. No. 7,374,885). Real-time TMA assays used the following oligonucleotides for the different miRNAs, Table 4

TABLE 4

Promoter-Based Amplification Oligomer and Extender Oligomer Combinations

| Small RNA | T7 Provider (5' → 3') | 3' Extender (5' → 3') |
|---|---|---|
| miR-21 | AATTTAATACGACTCACTATA GGGAGAUAGCUUAUCAGA | CGGTCGCAGAGATTAACTGGTACAGGGT TAAGCGTGGTCGACCGTCAACATCAGT |
| miR-34b | AATTTAATACGACTCACTATA GGGAGATAGGCAGTGTCA | CGGTCGCAGAGATTAACTGGTACAGGGT TAAGCGTGGTCGACCGCAATCAGCTAAT |
| miR-182 | AATTTAATACGACTCACTATA GGGAGATTTGGCAATGGT | CGGTCGCAGAGATTAACTGGTACAGGGT TAAGCGTGGTCGACCGAGTGTGAGTTCT |
| miR-221 | AATTTAATACGACTCACTATA GGGAGACCACAACGGTTTAGC UACAUUGUCUG | CGGTCGCAGAGATTAACTGGTACAGGGT TAAGCGTGGTCGACCGGAAACCCAGCAG |
| miR-222 | AATTTAATACGACTCACTATA GGGAGAAGCUACAUCUGG | CGGTCGCAGAGATTAACTGGTACAGGGT TAAGCGTGGTCGACCGGAGACCCAGTAG |
| miR-802 | AATTTAATACGACTCACTATA GGGAGACAGTAACAAAGA | CGGTCGCAGAGATTAACTGGTACAGGGT TAAGCGTGGTCGACCGACAAGGATGAAT |

All assays used the same reverse primer (5'-CGGUCGCA-GAGATTAACT) and molecular beacon labeled at the 5' end with FAM and at the 3' end with Dabcyl (5'-CCGA-CAAGCGUGGUCGACGUCGG). Specific target capture of miRNAs: Capture of mature miRNAs was performed using the following chimeric hairpin target capture oligonucleotides (TCO) (US Pat. Pub. No. 2006/0068417): for miR-21 (5'-TTTTTTTTTTTTUCAACAUCAGU-CUGAUAAGCUAAAAAAAAAAAAA), for miR-182 (5'-TTTTTTTTTTTTAGUGUGAGUUCUACCA-UUGCCAAAAAAAAAAAAAAA), for miR-221 (5'-TTTTTTTTTTTTGAAACCCAGCAGACAAUGUAGCUA AAAAAAAAAAA), for miR-222 (5'-TTTTTTTTTTTTAC-CCAGUAGCCAGAUGUAGCUAAAAAAAAAAAAA), and for miR-802 (5 -TTTTTTTTTTTTACAAGGAUGAAUCU-UUGUUACUGAAAAAAAAAAAA). The TCO was added with APTIMA Target Capture Reagent to RNA samples in Solution Transport Medium (Gen-Probe Inc.) and heated to 75.deg.C. for 15 minutes in a 96-well deep well heater (model IC25 with block 620-5036, Torrey Pines Scientific Inc., San Marcos, Calif.) to denature the hairpin. The reaction mixture was then cooled to room temperature over 30 minutes to anneal each specific miRNA to its designated TCO. After binding to the miRNA, the 3' polyA tail of the TCO was hybridized to the polyT tail of a polyT derivatized magnetic beads (APTIMA Target Capture Reagent). The beads were collected using a Kingfisher96 PCR tip head (Thermo Scientific, Waltham, Mass.), washed in APTIMA wash solution, and mixed with APTIMA amplification reagent containing amplification and detection oligonucleotides in a 96-well PCR plate as described above. To liberate the miRNA from the TCO, the PCR plate was incubated at 90.deg.C. for 5 minutes and then immediately cooled on ice for 5 minutes.

MicroRNA profiling: Total RNA was extracted from 22 human prostate cancer xenografts using Trizol Reagent (Invitrogen, Carlsbad, Calif.) with homogenization by Polytron. The samples were shipped to Asuragen Services for microRNA profiling. Samples for microRNA profiling studies were processed by Asuragen Services according to the company's standard operating procedures. Briefly, a custom-manufactured Affymetrix GeneChip from Ambion was designed to microRNA probes derived from Sanger mirBase 9.2 and published reports (Cummins, Proc Natl Acad Sci USA 2006, 103:3687-3692; Bentwich, Nat Genet 2005, 37:766-770; Berezikov, Cell 2005, 120:21-24; Xie, Nature 2005, 434:338-345). The array was designed with 2 staggered probes to represent each microRNA. The signal processing implemented for the Ambion miRCHIP is a multi-step process involving probe specific signal detection calls, background estimate and correction, constant variance stabilization, and either array scaling or global normalization. For each probe, an estimated background value is subtracted that is derived from the median signal of a set of G-C-matched anti-genomic controls. Arrays within a specific analysis experiment were normalized together according to the variance stabilization method (Huber, Bioinformatics 2002, 18 Suppl 1:S96-104). Detection calls were based on a Wilcoxon rank-sum test of the microRNA probe signal compared to the distribution of signals from GC-content matched anti-genomic probes. For statistical hypothesis testing, a two-sample t-Test with assumption of equal variance was applied. One-way ANOVA was used for experimental designs with more than two experimental groupings or levels of the same factor. These tests define which probes are considered to be significantly differentially expressed, or significant, based on a default p-value of 0.001 and log 2 difference>1.

TaqMan validation of microarray results for normal and xenograft for miR-21, miR-182, miR-221 and miR-222:

Absolute copy number of mature microRNAs was determined by quantitative real-time PCR (qRT-PCR) using Assays-on-Demand TaqMan primer/probe sets along with TaqMan Universal PCR master mix (Applied Biosystems Inc., Foster City, Calif.) for cDNA amplification. Amplification and analysis were performed on the ABI 7000 sequence detection system. Copies per cell were determined using an estimated 15 pg total RNA per cell as described (Chen, Nucleic Acids Res 2005, 33:e179).

Example 7

Figure 4:
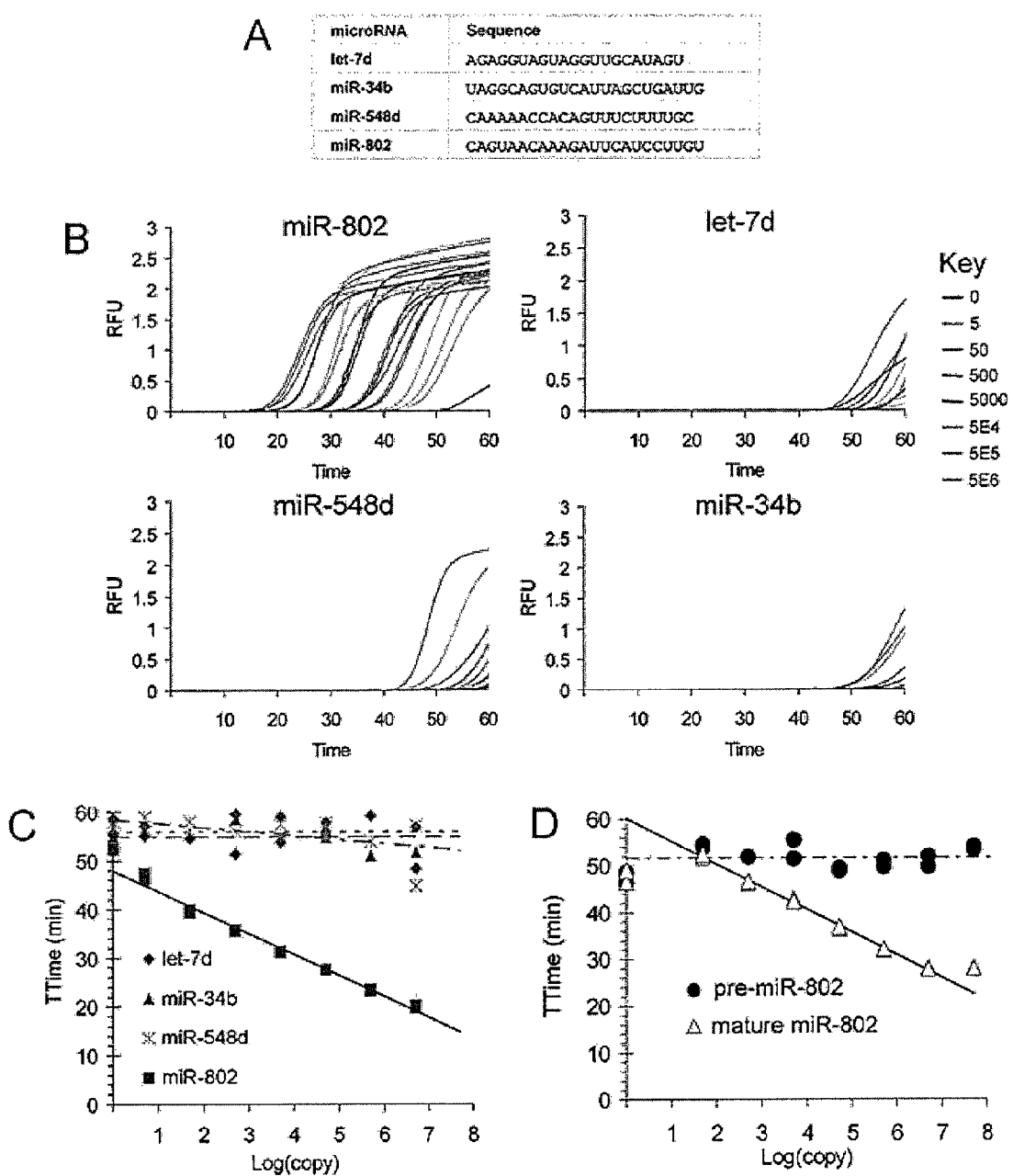
FIGS. 4a-d shows the specificity of the miRNA TMA assay. A) Sequences of mature miRNAs tested. B) Amplification curves from tests of the miR-802 assay on various input copy numbers of synthetic miRNA targets. RFU: Relative fluorescence units. C) Calibration chart for the amplification curves in B. D) Calibration chart for the miR-802 assay tested on various copy number input of mature target vs. pre-miR-802 transcript.

Real-Time TMA Assays Distinguish Mature miRNA Sequences from Pre-miRNA Sequences and from Related and Unrelated Non-Target miRNA Sequences The miR-802 resides in chromosomal region 21q22.12, which is near regions of TMPRSS2 and Ets family member chromosomal breakpoints (21q21.2-21.3) associated with aggressive forms of prostate cancer (Kumar-Sinha, Nat Rev Cancer 2008, 8:497-511; Mehra, Cancer Res 2008, 68:3584-3590). A real-time TMA assay was performed for specific detection of mature miR-802 template when compared to unrelated miRNAs let-7d, miR-34b and miR-548d and compared to the pre-miR-802 precursor (FIGS. 4A-C). Target nucleic acids were as follows: SEQ ID NO:34, SEQ ID NO:27, SEQ ID NO:29, SEQ ID NO:32, and SEQ ID NO:33, respectively. Target nucleic acids were prepared at $5\times10^7$ copies and 10-fold serial dilutions down to 5 copies was made. Negative controls were water. Amplification reactions were preformed in triplicate and include one of the target or non-target nucleic acids. Amplification and detection oligomers were SEQ IS NOS:13, 19, 20 and 21. Results are presented in table 5 and in FIG. 4.

TABLE 5

| Nucleic Acid (amount) | Average TTime (minutes) |
|---|---|
| let7d (5 copies) | 57.0 |
| let7d (50 copies) | 56.1 |
| let7d (500 copies) | 54.6 |
| let7d (5,000 copies) | 55.4 |
| let7d (50,000 copies) | 56.4 |
| let7d (5 × 10.sup.5) | 56.3 |
| let7d (5 × 10.sup.6) | 59.2 |
| let7d (5 × 10.sup.7) | 52.6 |
| mir34b (5 copies) | 55.6 |
| mir34b (50 copies) | >60 |
| mir34b (500 copies) | >60 |
| mir34b (5,000 copies) | 58.4 |
| mir34b (50,000 copies) | >60 |
| mir34b (5 × 10.sup.5) | 55.7 |
| mir34b (5 × 10.sup.6) | 50.9 |
| mir34b (5 × 10.sup.7) | 51.7 |
| mir548d (5 copies) | 57.3 |
| mir548d (50 copies) | 57.8 |
| mir548d (500 copies) | 57.1 |
| mir548d (5,000 copies) | 55.9 |
| mir548d (50,000 copies) | 56.2 |
| mir548d (5 × 10.sup.5) | 56.4 |
| mir548d (5 × 10.sup.6) | 54.0 |
| mir548d (5 × 10.sup.7) | 51.0 |
| mir802 (5 copies) | 52.3 |
| mir802 (50 copies) | 46.7 |
| mir802 (500 copies) | 39.6 |
| mir802 (5,000 copies) | 35.7 |
| mir802 (50,000 copies) | 31.1 |
| mir802 (5 × 10.sup.5) | 27.6 |

TABLE 5-continued

| Nucleic Acid (amount) | Average TTime (minutes) |
|---|---|
| mir802 (5 × 10.sup.6) | 23.4 |
| mir802 (5 × 10.sup.7) | 20.0 |

Some nonspecific amplification was observed for the let-7d and miR-34b targets after a threshold time (TTime) of 50 minutes (FIG. 4B) and in control reactions that contained no template. TTimes for miR-802 ranged from about 20 minutes to about 52 minutes, and detected as few as 5 copies per reaction showing specific and sensitive amplification and detection.

The specificity of the miR-802 assay for mature sequences was tested on mature miR-802 and pre-miR-802; a hairpin precursor in vitro transcript of the mature miR. Mature processed miRNAs have different cellular functions from their hairpin precursors, and thus it is desirable that they are differentiated by a detection system. Target nucleic acid was prepared at $5\times10^7$ copies and 10-fold serial dilutions down to 5 copies were made. Non-target nucleic acid was prepared at $5\times10^7$ copies and 10-fold serial dilutions down to 5 copies were made. Negative controls were water. Amplification reactions were preformed in triplicate and include one of the target nucleic acids and one of the non-target nucleic acids each at equal amounts. As shown in FIG. 4, the miR-802 assay showed good discrimination of the mature miR-802 template from its corresponding hairpin precursor, with differential detection being between 50 and 500 copies of each species. The amplification and detection oligomers and methods provide sensitive and specific results in the presence of unrelated non-target nucleic acids and in the presence of precursor nucleic acid molecules.

Figure 5:
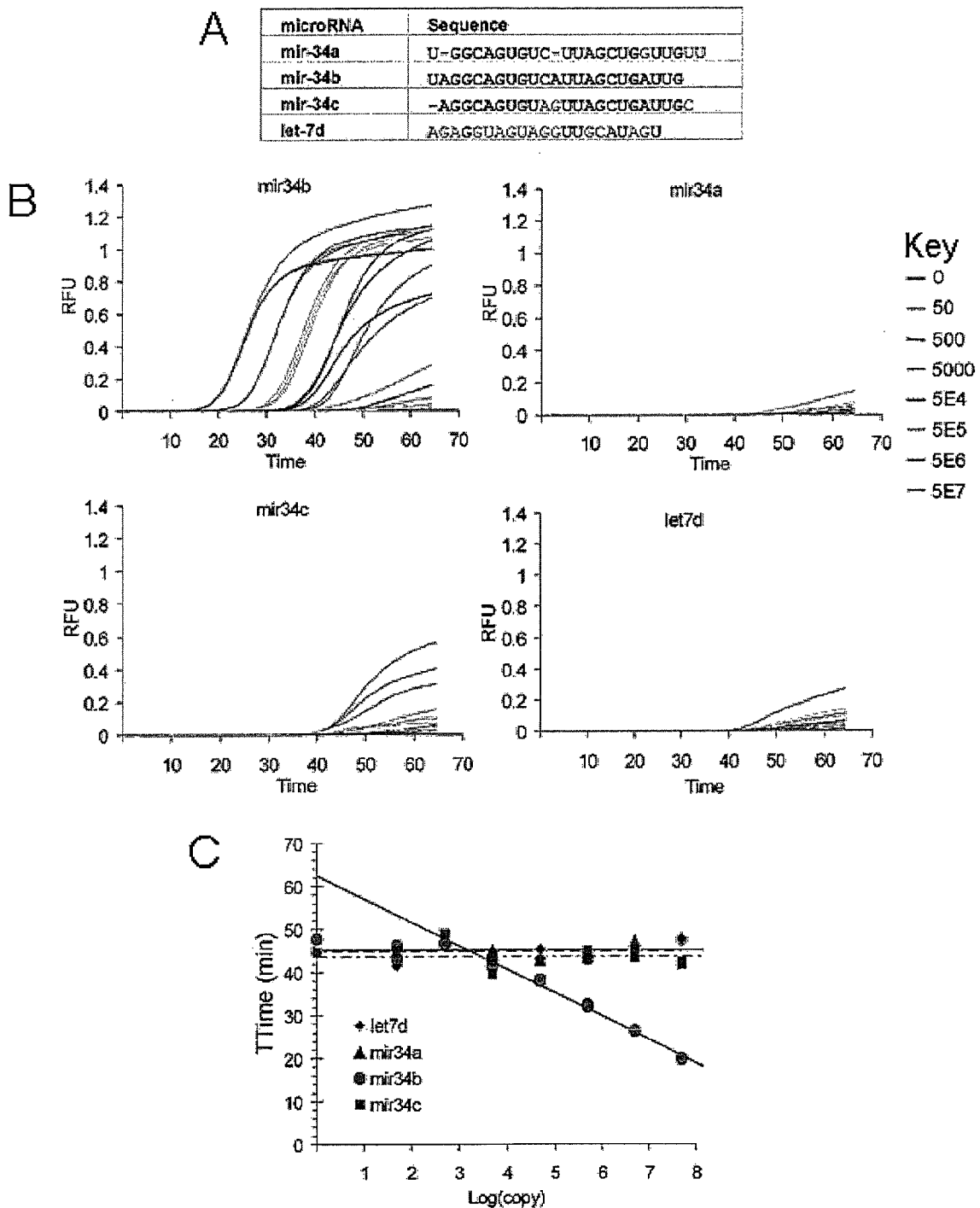
FIGS. 5a-c shows the specificity of the miR TMA assay. A) Sequences of mature miRNAs tested. B) Amplification curves from tests of the miR-34b assay on various copy number input of related miR-34 family members along with unrelated let-7d non-target nucleic acids. RFU: Relative fluorescence units. C) Calibration chart for the amplification curves in B.

Because miRNA family members can differ in sequence by one or more nucleotides, we next designed a system to demonstrate the sequence specificity of our real-time TMA assay against related non-target nucleic acids. A real-time TMA assay to specifically detect miR-34b and was tested against miR-34 family members miR-34a, miR-34c and other non-target miRNA let-7d. Target nucleic acids were as follows: SEQ ID NO:29, SEQ ID NO:35, SEQ ID NO:36 and SEQ ID NO:27, respectively. Amplification and detection oligomers were SEQ ID NOS:9, 15, 20 and 21. Target nucleic acids were prepared at $5\times10^7$ copies and 10-fold serial dilutions down to 5 copies was made. Negative controls were water. Amplification reactions were preformed in triplicate and include one of the target or non-target nucleic acids. As shown in FIG. 5 and table 6, the miR-34b assay showed template-dependent amplification at about 20 minutes with $5\times10^7$ input copies per reaction using miR-34b synthetic miRNA template compared to synthetic mature miRNA family members miR-34a and miR-34c and the unrelated miRNA let-7d. Some cross-reactivity was seen with $5\times10^7$ copies per reaction of the related species miR-34c at about 42 minutes (FIG. 5B), which is approximately the time that background signal was detected in the no template control reaction (about 45 minutes). Thus, the analytical sensitivity of this assay for the miR-34b species was less than 50,000 copies per reaction in the presence of related target nucleic acids. The amplification and detection oligomers and methods provide sensitive and specific results in the presence of related non-target nucleic acid.

TABLE 6

| Nucleic Acid (amount) | Average TTime (minutes) |
|---|---|
| let7d (5 copies) | 44.6 |
| let7d (50 copies) | 41.7 |
| let7d (500 copies) | 47.2 |
| let7d (5,000 copies) | >50 |
| let7d (50,000 copies) | 44.2 |
| let7d (5 × 10.sup5) | 44.4 |
| let7d (5 × 10.sup6) | 45.3 |
| let7d (5 × 10.sup7) | 47.5 |
| mir34a (5 copies) | >50 |
| mir34a (50 copies) | 44.9 |
| mir34a (500 copies) | >50 |
| mir34a (5,000 copies) | 45.0 |
| mir34a (50,000 copies) | 42.8 |
| mir34a (5 × 10.sup5) | 44.1 |
| mir34a (5 × 10.sup6) | 47.1 |
| mir34a (5 × 10.sup7) | >50 |
| mir34b (5 copies) | 47.7 |
| mir34b (50 copies) | 44.6 |
| mir34b (500 copies) | 46.6 |
| mir34b (5,000 copies) | 42.1 |
| mir34b (50,000 copies) | 38.0 |
| mir34b (5 × 10.sup5) | 32.1 |
| mir34b (5 × 10.sup6) | 26.3 |
| mir34b (5 × 10.sup7) | 19.9 |
| mir34c (5 copies) | 44.8 |
| mir34c (50 copies) | 44.9 |
| mir34c (500 copies) | 49.0 |
| mir34c (5,000 copies) | 41.4 |
| mir34c (50,000 copies) | >50 |
| mir34c (5 × 10.sup5) | 43.9 |
| mir34c (5 × 10.sup6) | 43.7 |
| mir34c (5 × 10.sup7) | 42.1 |

The need to discriminate between closely related family members is highly desirable for a diagnostic assay. The above data show that the current compositions and methods provide a highly selective assay with sensitivities from about 5 to about 5000 copies of target nucleic acid in the presence of unrelated target nucleic acids, related precursor nucleic acids and related mature miRs. To improve this performance in the presence of related nucleic acid molecules, the length of the 3'-extender primer was increased. In some instances, this resulted in elevated background signals, presumably due to increased sequence overlap with the T7-provider oligonucleotide (i.e. resulting in non-specific amplification). Use of a target capture oligomer to specifically hybridize and isolate target nucleic acids further improves assay sensitivity and specificity.

A particular advantage of these assays is that FFPE sections, in addition to fresh or frozen tissue, can be placed directly in STM for convenient transport and/or storage. The miRNA targets can then be specifically captured directly from the STM buffer without the need for additional RNA purification.

Example 8 miR-21, miR-182, miR-221 and miR-22 for Diagnostic Panel

Several miRNAs were prioritized based on their relative expression levels determined in our microarray assay (Example 6). Top candidates were further selected on criterion such as chromosomal location, predicted biological contexts, and published studies. In Example 6, we examined miRNA profiles of human prostate cancer xenografts to determine which miRNAs could be detected in moderate to high abundance and which were differentially expressed compared to normal prostate tissue. Based on this analysis, we concluded that miR-802 was not highly expressed in the xenografts and was not differentially expressed between normal and tumor samples. In contrast, we identified several miRNAs that showed high levels of expression and/or were differentially expressed in the xenografts. Four of these miRNAs, miR-221, miR-222, miR-21 and miR-182, were selected for detection using real-time TMA assays. Surprisingly, miR221 and miR222 showed high expression across all xenographs, but was strongly downregulated in prostate tumor tissue compared to normal tissue, (see Siva et al, Mol. Cancer (2009), 8:17). Target nucleic acids were as follows: SEQ ID NO:38 (miR-21), SEQ ID NO:41 (miR-182), SEQ ID NO:44 (miR-221) and SEQ ID NO:47 (miR-222). Amplification and detection oligomers were as follows: for miR-21, SEQ ID NOS:8, 14, 20, 21; for miR-182, 10, 16, 20, 21; for miR-221, SEQ ID NOS:11, 17, 20, 21; and for miR-222, 12, 18, 20, 21. Target nucleic acids were prepared at 5×10.sup.7 copies and 10-fold serial dilutions down to 5 copies were made. Negative controls were water. Amplification reactions were preformed in triplicate and include one of the target nucleic acids. As shown in FIG. 6A, miR-221, miR-222, miR-21 and miR-182 all showed good analytical performance. In a second assay, selectivity for miR-221 in the presence of miR-222 mir-30b (SEQ ID NO:50) and miR-802 was shown. Amplification and detection oligomers were SEQ ID NOS:11, 17, 20, 21. Target nucleic acid was prepared at 5×10.sup.7 copies and 10-fold serial dilutions down to 5 copies were made. Non-target nucleic acid was prepared at 5×10.sup.7 copies and 10-fold serial dilutions down to 5 copies were made. Negative controls were water. Amplification reactions were preformed in triplicate and include one of the target nucleic acids and one of the non-target nucleic acids each at equal amounts. Results are shown in FIG. 6B, and are analogous to our previous demonstration for the miR-802 assay. The assay showed good discrimination for the target nucleic acid, with differential detection being between 50 and 500 copies of miR-221 and the non-target nucleic acid, including miR-222. The amplification and detection oligomers and methods provide sensitive and specific results in the presence of unrelated non-target nucleic acids and in the presence of precursor nucleic acid molecules.

TMA assays for these miRNAs miR-21, miR-182, miR-221 and miR-222 showed accurate and reproducible quantitation using 10 ng of total RNA from these tissues. The TMA assay showed good specificity in the presence of related target nucleic acids. Similar results were also obtained when these miRNAs were detected directly from STM extracted clinical FFPE specimens and urine sediments (data not shown).

Example 9 miRNA Copy Number in Prostate Cancer Cell Lines and Xenografts

Figure 7:
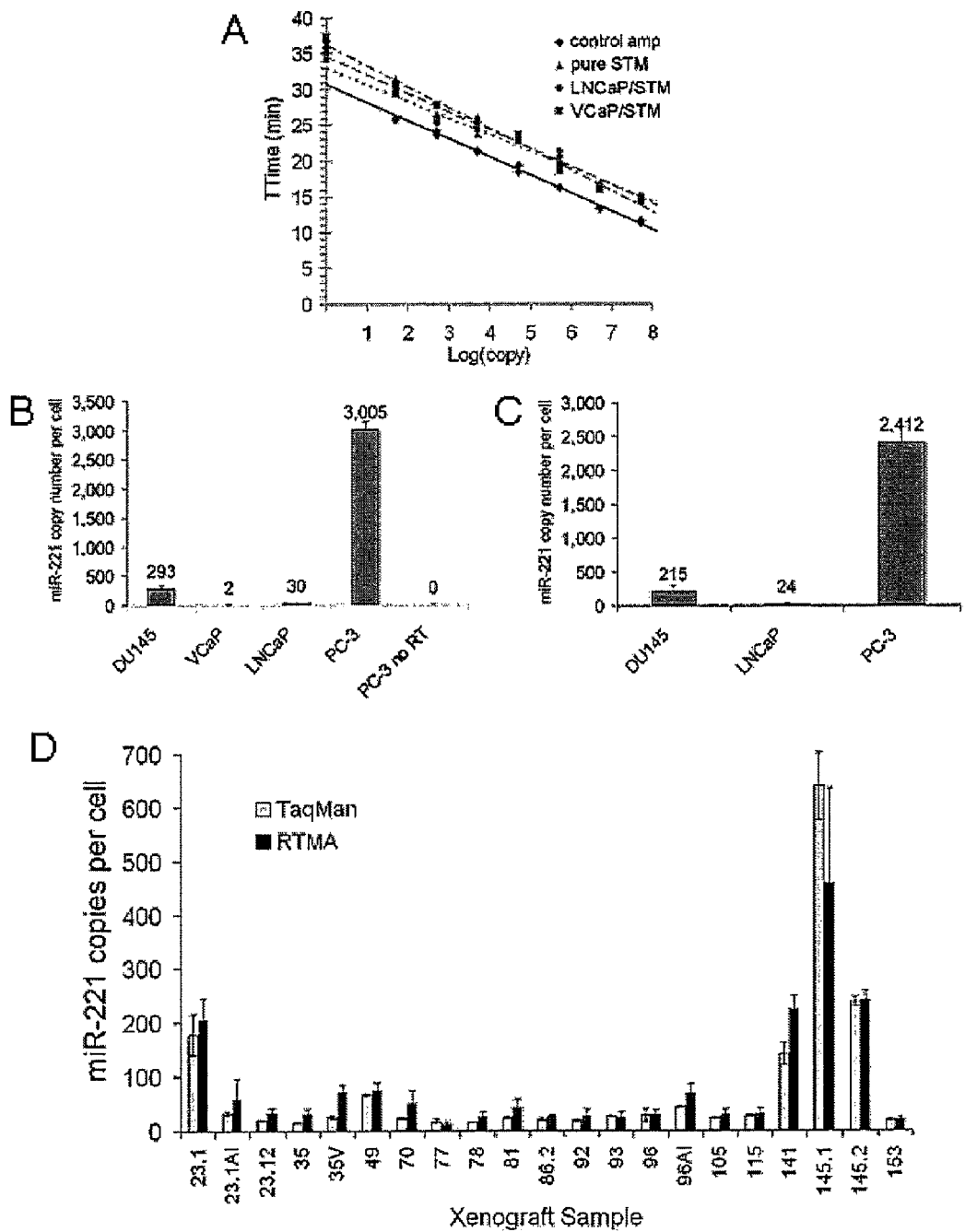
FIGS. 7a-d shows miRNA assays with target capture. A) Capture and detection of known inputs of synthetic miR-221 added directly to STM buffer or to STM containing 10 ng of total cellular RNA (derived from VCaP or LNCaP cells, as indicated). Control reactions were run with synthetic miR-221 spiked directly into amplification reagent (without target capture or total RNA). B) miR-221 copy levels determined by a commercial TaqMan RT-qPCR assay. C) miR-221 copy levels determined by a miR real-time TMA assay (with target capture). D) miR-221 copy numbers determined in prostate cancer xenografts using a commercial TaqMan RT-qPCR assay (without target capture) and a miR real-time TMA assay (with target capture). For all real-time TMA samples, 10 ng total RNA was assayed per reaction in triplicate.

To assess the efficiency of our real-time TMA assay for capturing and detecting miRNA from a complex mixture, known quantities of synthetic miR-221 were added to either Solution Transport Medium (STM) or STM containing total RNA extracted from LNCaP or VCaP cells (10 ng total RNA per reaction), both of which were shown separately to contain low or undetectable levels of endogenous miR-221. Control reactions were run with synthetic miR-221 transcripts added directly to amplification reagent (without target capture and without the addition of total RNA). Capture and amplification efficiencies for known input copy numbers of synthetic miR-221 were similar in the presence or absence of total cellular RNA (FIG. 7A, curves for "LNCaP/STM" and "VCaP/STM" compared to "pure STM"), indicating that the integrated target capture and amplification/detection compositions and methods provide highly accurate detection data, even for target nucleic acids present in an abundant and mixed population of non-target nucleic acids. Moreover, the integrated target capture and amplification/detection performed only slightly less efficiently than did the control reaction wherein the target nucleic acid was added directly into the amplification reaction mixture. (FIG. 7A, "control amp"). Thus, the integrated target capture and amplification/detection reaction is a very robust system for detecting even minute amounts of target nucleic acids in the presence of an abundance of non-target nucleic acids.

Figure 8:
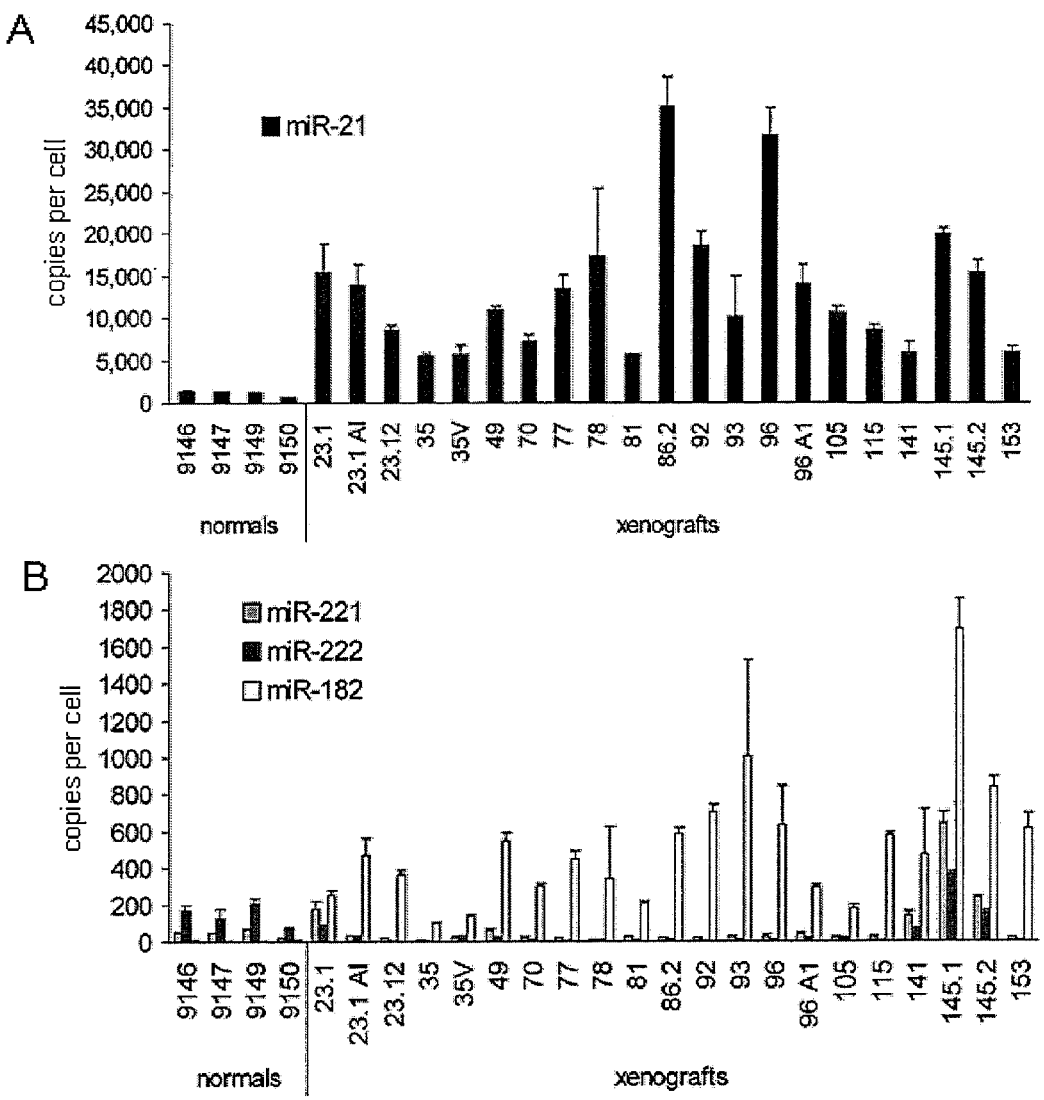
FIGS. 8a-b shows an absolute copy number determination for A) miR-21 and B) miR-221, miR-222, and miR-182. Synthetic mature microRNAs were diluted 10-fold from $1 \times 10.\text{sup}.9$ copies per reaction for construction of each standard curve. For each reverse transcription reaction, 10 ng of total RNA was used and reactions were run in triplicate according to manufacturer's instructions.

Using a commercial TaqMan qRT-PCR assay and the above TMA assay, endogenous expression levels of miR-221 were measured in the prostate cancer cell lines LNCaP, PC-3, DU145 and VCaP (FIG. 7B). We measured relatively low or undetectable levels of endogenous miR-221 in LNCaP and VCaP cells as reported above. Results from the TaqMan qRT-PCR assays showed 3005 copies of miR-221 per PC-3 cell and 293 copies per DU145 cell, while the TMA with integrated target capture showed 2414 and 215 copies. (FIGS. 7B-C) Differences in data could be due to false positive results in the commercial RT-PCR assay, which did not include a target capture step. However, additional studies should be performed to further understand the mechanism behind the high positive results for the commercial kits. These tests were also performed on total RNA isolated from prostate cancer xenograft samples (FIG. 7D). Endogenous expression levels of miR-21, miR-182, miR-221 and miR-222 were measured using a TMA assay with integrated target capture, amplification and detection. Our results for miR-21 expression in tumor xenograft samples showed about a 5- to 25-fold upregulation in these tissues compared to normal samples with copy numbers ranging from 5000 to 35,000 copies per cell (FIG. 8A). Due to its implied role in cancer and its high level of expression in prostate tumor compared to normal prostate samples, miR-21 may have value in distinguishing tumor from normal tissue. These results also showed miR-182 was highly upregulated in the majority of tumor tissues compared to normal samples (FIG. 8B). We did not observe a significant difference in miR-221 or miR-222 expression in the three matched pairs of androgen dependent and androgen independent xenograft lines (LuCaP 23.1/23.1 AI, 35135V, and 96/96AI, FIG. 8B). Expression levels for miR-221 and miR-222 in patient biopsy cores, metastatic lymph node specimens, and non-malignant prostate tissues suggest that these miRNAs could be associated with invasive prostate cancer. Based on these and other observations, miR-221 and miR-222 appear to be promising biomarker candidates for discriminating metastatic subtypes.

TABLE 7

Precursor, Mature and Minor miR Sequences Discussed herein

| SEQ ID NO | Seq 5 → 3 | MiR name | miRBase Accession Number |
|---|---|---|---|
| 27 | agagguaguagguugcauaguu | let-7d | MIMAT0000065 |
| 28 | GUGCUCGGUUUGUAGGCAGUGUCAUUAGCUGAUUGUACUGUGGUGGUUACAAUCACUAACUCCACUGCCAUCAAAACAAGGCAC | pre-miR-34b | MI0000742 |
| 29 | caaucacuaacuccacugccau | miR-34b | MIMAT0004676 |
| 30 | uaggcagugucauuagcugauug | minor miR-34b | MIMAT0000685 |
| 31 | aaaaguaauugugguuuuugcc | miR-548d-5p | MIMAT0004812 |
| 32 | caaaaccacaguuucuuuugc | miR-548d-3p | MIMAT0003323 |
| 33 | GUUCUGUUAUUUGCAGUCAGUAACAAAGAUUCAUCCUUGUGUCCAUCAUGCAACAAGGAGAAUCUUUGUCACUUAGUGUAAUUAAUAGCUGGAC | pre-miR-802 | MI0003906 |
| 34 | caguaacaaagauucauccuugu | miR-802 | MIMAT0004185 |
| 35 | uggcagugucuuagcugguugu | miR-34a | MIMAT0000255 |
| 36 | aggcaguguaguuagcugauugc | miR-34c | MIMAT0000686 |
| 37 | UGUCGGGUAGCUUAUCAGACUGAUGUUGACUGUUGAAUCUCAUGGCAACACCAGUCGAUGGGCUGUCUGACA | pre-miR-21 | MI0000077 |
| 38 | UAGCUUAUCAGACUGAUGUUGA | miR-21 | MIMAT0000076 |
| 39 | CAACACCAGUCGAUGGGCUGU | minor miR-21 | MIMAT0004494 |
| 40 | GAGCUGCUUGCCUCCCCCCGUUUUUGGCAAUGGUAGAACUCACACUGGUGAGGUAACAGGAUCCGGUGGUUCUAGACUUGCCAACUAUGGGGCGAGGACUCAGCCGGCAC | pre-miR-182 | MI0000272 |

TABLE 7-continued

Precursor, Mature and Minor miR Sequences Discussed herein

| SEQ ID NO | Seq 5 → 3 | MiR name | miRBase Accession Number |
|---|---|---|---|
| 41 | uuuggcaauggguagaacucacacu | miR-182 | MIMAT0000259 |
| 42 | agguucuagacuugccaacua | minor miR-182 | MIMAT0000260 |
| 43 | UGAACAUCCAGGUCUGGGGCAUG AACCUGGCAUACAAUGUAGAUUU CUGUGUUCGUUAGGCAACAGCUA CAUUGUCUGCUGGGUUUCAGGCU ACCUGGAAACAUGUUCUC | pre-miR-221 | MI0000298 |
| 44 | AGCUACAUUGUCUGCUGGGUUUC | miR-221 | MIMAT0000278 |
| 45 | accuggcauacaauguagauuu | minor miR-221 | MIMAT0004568 |
| 46 | GCUGCUGGAAGGUGUAGGUACCC UCAAUGGCUCAGUAGCCAGUGUA GAUCCUGUCUUUCGUAAUCAGCA GCUACAUCUGGCUACUGGGUCUC UGAUGGCAUCUUCUAGCU | pre-mir-222 | MI0000299 |
| 47 | agcuacaucuggcuacugggu | miR-222 | MIMAT0000279 |
| 48 | cucaguagccaguguagauccu | minor miR-222 | MIMAT0004569 |
| 50 | uguaaacauccuacacucagcu | miR30b | MIMAT0000420 |

---

We claim:

1. A multiplex amplification method for specifically detecting the presence of target nucleic acids in a sample comprising the steps of:

(a) providing a target capture probe for capturing a miR-221 target nucleic acid and a target capture probe for capturing a miR-182 target nucleic acid, wherein the target capture probes are each made up of an internal target hybridizing sequence flanked by a capture region and a terminal region, wherein the terminal region binds to the capture region to form a double-stranded stem portion of the hairpin structure, wherein the target hybridizing region forms a single-stranded loop portion of the hairpin structure, and wherein the target hybridizing sequence of the miR-221 target capture probe is substantially complementary to all or a portion of a miR-221 sequence and the target hybridizing sequence of the miR-182 target capture probe is substantially complementary to all or a portion of a miR-182 sequence, wherein the target capture probe that specifically hybridizes to a miR-221 target nucleic acid has a nucleotide sequence that is at least 95% identical to SEQ ID NO:24, and wherein the target capture probe that specifically hybridizes to a miR-182 target nucleic acid has a nucleotide sequence that is at least 95% identical to SEQ ID NO:23,
(b) mixing a sample suspected of containing a miR-221 target nucleic acid and a miR-182 target nucleic acid with the capture probes,
(c) specifically hybridizing the target hybridizing sequence of the capture probes to a target sequence in their respective target nucleic acids,
(d) binding the capture regions to an immobilized probe attached to a capture support by binding together members of a specific binding pair, thereby forming a capture hybrid made up of the miR-221 target nucleic acid, the capture probe and the immobilized probe attached to the capture support, and a capture hybrid made up of the miR-182 target nucleic acid, the capture probe, and the immobilized probe attached to the capture support,
(e) separating the capture hybrids from other components in the sample,
(f) releasing the miR-221 and miR-182 target nucleic acids from the capture hybrids and providing a set of conditions wherein the target capture probes are partially double-stranded hairpin structures,
(g) providing to the mixture comprising the released miR-221 and miR-182 target nucleic acids and the target capture probes a plurality of amplification oligomers, the plurality comprising
  (i) at least a first amplification oligomer and a promoter-based oligomer for specifically hybridizing to a miR-221 target nucleic acid or cDNA strand thereof, wherein the first amplification oligomer comprises a target hybridizing sequence, a portion of which is substantially identical to a portion of the target hybridizing region of the miR-221 target capture probe, and wherein the promoter-based oligomer comprises a target hybridizing sequence, a portion of which is substantially complementary to a portion of the target hybridizing region of the miR-221 target capture probe, and
  (ii) at least a first amplification oligomer and a promoter-based oligomer for hybridizing to a miR-182 target nucleic acid or cDNA strand thereof, wherein the first amplification oligomer comprises a target hybridizing sequence, a portion of which is substantially identical to a portion of the target hybridizing region of the miR-182 target capture probe, and wherein the promoter-based oligomer comprises a target hybridizing sequence, a portion of which is substantially complementary to a portion of the target hybridizing region of the miR-182 target capture probe;
(h) providing a set of conditions wherein the first amplification oligomers hybridizes to their respective target nucleic acids,
(i) performing an amplification reaction using the plurality of amplification oligomers to generate amplification products from the miR-221 and miR-182 target nucleic acids; and
(j) detecting the amplification products to indicate presence of miR-221 target nucleic acid, miR-182 target nucleic acid or both in the sample.

2. The method of claim 1, wherein binding the capture region to the immobilized probe results from hybridizing complementary sequences of the capture region and the immobilized probe.

3. The method of claim 1, wherein the capture region is a nucleotide sequence selected from the group consisting of: $dT_{(0-3)}A_{(10-30)}$.

4. The method of claim 1, wherein the capture region is $dA_{(12)}$.

5. The method of claim 1, wherein releasing the miR-221 and miR-182 target nucleic acids from the capture hybrids further releases the capture probes from the immobilized probes.

6. The method of claim 1, wherein the target capture probe that specifically hybridizes to a miR-221 target nucleic acid is SEQ ID NO:24.

7. The method of claim 1, wherein the target capture probe that specifically hybridizes to a miR-182 target nucleic acid is SEQ ID NO:23.

8. The method of claim 1, wherein the miR-221 first amplification oligomer has an extension nucleic acid sequence that is at least 95% identical to SEQ ID NO:49.

9. The method of 1, wherein the first amplification oligomer that specifically hybridizes to miR-221 is an extender primer comprising a 3' target hybridizing sequence and a 5' extension nucleic acid sequence, wherein the 3' target hybridizing sequence is substantially identical to about 9 or more contiguous nucleic acids at the 5' end of the target hybridizing sequence of the miR-221 target capture probe.

10. The method of claim 9, wherein the miR-221 target capture probe is SEQ ID NO:24.

11. The method of claim 9, wherein the miR-221 first amplification oligomer has an extension nucleic acid sequence that is at least 95% identical to SEQ ID NO:49.

12. The method of claim 1, wherein the first amplification oligomer is SEQ ID NO:17.

13. The method of 1, wherein the first amplification oligomer that specifically hybridizes to miR-182 is an extender primer comprising a 3' target hybridizing sequence and a 5' extension nucleic acid sequence, wherein the 3' target hybridizing sequence is substantially identical to about 9 or more contiguous nucleic acids at the 5' end of the target hybridizing sequence of the miR-182 target capture probe.

14. The method of claim 13, wherein the miR-182 target capture probe is SEQ ID NO:23.

15. The method of claim 13, wherein the miR-182 first amplification oligomer has an extension nucleic acid sequence that is at least 95% identical to SEQ ID NO:49.

16. The method of claim 1, wherein the first amplification oligomer is SEQ ID NO:16.

17. The method of claim 12, wherein the first amplification oligomer that specifically hybridizes to miR-182 is an extender primer comprising a 3' target hybridizing sequence and a 5' extension nucleic acid sequence, wherein the 3' target hybridizing sequence is substantially complementary to about 9 or more contiguous nucleic acids at the 3' end of SEQ ID NO:41.

18. The method of claim 1, wherein the promoter based oligomer that specifically hybridizes to a complement of the miR-221 target nucleic acid comprises a target hybridizing sequence that is substantially complementary to 9 or more contiguous nucleic acids on 3' end of the miR-221 target capture probe target hybridizing region.

19. The method of claim 1, wherein the promoter based amplification oligomer that specifically hybridizes to a complement of the miR-221 target nucleic acid is SEQ ID NO:11.

20. The method of claim 19, wherein the promoter based oligomer that specifically hybridizes to a complement of the miR-221 target nucleic acid comprises a target hybridizing sequence that is substantially complementary to 9 or more contiguous nucleic acids on 3' end of the miR-221 target capture probe target hybridizing region.

21. The method of claim 1, wherein the promoter based oligomer that specifically hybridizes to a complement of the miR-182 target nucleic acid comprises a target hybridizing sequence that is substantially complementary to 9 or more contiguous nucleic acids on 3' end of the miR-182 target capture probe target hybridizing region.

22. The method of claim 1, wherein the promoter based amplification oligomer that specifically hybridizes to a complement of the miR-182 target nucleic acid is SEQ ID NO:10.

23. The method of claim 22, wherein the promoter based oligomer that specifically hybridizes to a complement of the miR-221 target nucleic acid comprises a target hybridizing sequence that is substantially complementary to 9 or more contiguous nucleic acids on 3' end of the miR-221 target capture probe target hybridizing region.

24. The method of claim 1, further comprising a reverse primer oligomer.

25. The method of claim 1, wherein the first amplification oligomer that specifically hybridizes to miR-221 is an extender primer comprising a 3' target hybridizing sequence and a 5' extension nucleic acid sequence, and wherein at or after step (g) a reverse primer is provided.

26. The method of claim 25, wherein the reverse primer is configured to hybridize to a portion of the complement of the extension nucleic acid.

27. The method of claim 1, wherein the first amplification oligomer that specifically hybridizes to miR-182 is an extender primer comprising a 3' target hybridizing sequence and a 5' extension nucleic acid sequence, and wherein at or after step (g) a reverse primer is provided.

28. The method of claim 27, wherein the reverse primer is configured to hybridize to a portion of the complement of the extension nucleic acid.

29. The method of claim 25, wherein the first amplification oligomer that specifically hybridizes to miR-182 is an extender primer comprising a 3' target hybridizing sequence and a 5' extension nucleic acid sequence, and wherein at or after step (g) a reverse primer is provided.

30. The method of claim 29, wherein the 5' extension nucleic acid sequences for both the miR-221 extender primer and the miR-182 extender primer are substantially identical and the reverse primer is a universal primer configured to hybridize to a portion of the complement of the extension nucleic acid.

31. The method of claim 29, wherein the 5' extension nucleic acid sequences for both the miR-221 extender primer and the miR-182 extender primer comprise a complement of a reverse primer target sequence.

32. The method of claim 31, wherein the complement reverse primer target sequences on the miR-221 extender primer and the miR-182 extender primer are substantially identical, and wherein the reverse primer is a universal primer.

33. The method of claim 24, wherein the reverse primer is SEQ ID NO:20.

34. The method of claim 30, wherein the reverse primer is SEQ ID NO:20.

35. The method of claim 32, wherein the reverse primer is SEQ ID NO:20.

36. The method of claim 1, wherein the amplification reaction is performed in the presence of target capture probe and wherein the amplification reaction conditions are configured to maintain the target capture probe in a hairpin formation.

37. The method of claim 1, wherein the amplification reaction is an isothermal amplification reaction.

38. The method of claim 1, wherein amplification products are detected using a detection probe oligomer.

39. The method of claim 38, wherein the detection probe oligomer is a linear detection probe.

40. The method of claim 38, wherein the detection probe oligomer is a hairpin detection probe.

41. The method of claim 38, wherein the detection probe oligomer is labeled.

42. The method of claim 38, wherein the detection probe oligomer is dual labeled.

43. The method of claim 1, wherein the detection of the target nucleic acid is a real-time detection.

44. A method of detecting the presence of a target nucleic acid in a sample comprising the steps of:
(a) providing a target capture probe that forms under hybridizing conditions a partially double-stranded hairpin structure made up of an internal target hybridizing sequence flanked by a capture region and a terminal region, wherein the terminal region binds to the capture region to form a double-stranded stem portion of the hairpin structure, wherein the target hybridizing region forms a single-stranded loop portion of the hairpin structure, and wherein the target capture probe specifically hybridizes to a miR-221 target nucleic acid and has a nucleotide sequence that is at least 95% identical to SEQ ID NO:24,
(b) mixing a sample suspected of containing a miR-221 target nucleic acid with the capture probe,
(c) specifically hybridizing the target hybridizing sequence of the capture probe to a target sequence in the miR-221 target nucleic acid,
(d) binding the capture region to an immobilized probe attached to a capture support by binding together members of a specific binding pair, thereby forming a capture hybrid made up of the miR-221 target nucleic acid, the capture probe, and the immobilized probe attached to the capture support,
(e) separating the capture hybrid attached to the capture support from other components in the sample,
(f) releasing the miR-221 target nucleic acid from the capture hybrid,
(g) providing to the mixture comprising the released miR-221 target nucleic acid and the target capture probe at least a first amplification oligomer comprising a target hybridizing sequence, a portion of which is substantially identical to a portion of the target hybridizing region of the target capture probe;
(h) providing a set of conditions wherein the first amplification oligomer hybridizes to the miR-221 target nucleic acid and an amplification reaction takes place, and wherein the target capture probe is in a partially double stranded hairpin formation,
(i) generating a detectable amplification product in an amplification reaction wherein the first amplification oligomer generates a cDNA strand from the miR-221 target nucleic acid; and
(j) detecting the amplification product to indicate presence of miR-221 target nucleic acid in the sample.

45. A method of detecting the presence of a target nucleic acid in a sample comprising the steps of:
(a) providing a target capture probe that forms under hybridizing conditions a partially double-stranded hairpin structure made up of an internal target hybridizing sequence flanked by a capture region and a terminal region, wherein the terminal region binds to the capture region to form a double-stranded stem portion of the hairpin structure, wherein the target hybridizing region forms a single-stranded loop portion of the hairpin structure, and wherein the target capture probe specifically hybridizes to a miR-221 target nucleic acid and has a nucleotide sequence that is at least 95% identical to SEQ ID NO:24, (b) mixing a sample suspected of containing a miR-221 target nucleic acid with the capture probe, (c) specifically hybridizing the target hybridizing sequence of the capture probe to a target sequence in the miR-221 target nucleic acid, (d) binding the capture region to an immobilized probe attached to a capture support by binding together members of a specific binding pair, thereby forming a capture hybrid made up of the miR-221 target nucleic acid, the capture probe, and the immobilized probe attached to the capture support, (e) separating the capture hybrid attached to the capture support from other components in the sample, (f) releasing the miR-221 target nucleic acid from the capture hybrid and providing a set of conditions wherein the target capture probe is a partially double-stranded hairpin structure, (g) providing to the mixture comprising the released miR-221 target nucleic acid and the target capture probe a plurality of amplification oligomers, the plurality comprising at least a first amplification oligomer and a promoter-based oligomer, wherein the first amplification oligomer comprises a target hybridizing sequence, a portion of which is substantially identical to a portion of the target hybridizing region of the target capture probe, and wherein the promoter-based oligomer comprises a target hybridizing sequence, a portion of which is substantially complementary to a portion of the target hybridizing region of the target capture probe;

(h) providing a set of conditions wherein the first amplification oligomer hybridizes to the miR-221 target nucleic acid in the presence of the hairpin capture probe, (i) performing an amplification reaction using the plurality of amplification oligomers to generate amplification product from the miR-221 target nucleic acid; and (j) detecting the amplification product to indicate presence of miR-221 target nucleic acid in the sample.

\* \* \* \* \*